US008481021B2

(12) United States Patent
Sims et al.

(10) Patent No.: US 8,481,021 B2
(45) Date of Patent: Jul. 9, 2013

(54) IL-1F5 POLYPEPTIDES

(75) Inventors: John E Sims, Seattle, WA (US); Blair R Renshaw, Renton, WA (US); Christopher Gabel, Seattle, WA (US); Jennifer E. Towne, Seattle, WA (US); Randal R Ketchem, Snohomish, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/225,326

(22) Filed: Sep. 2, 2011

(65) Prior Publication Data

US 2012/0020918 A1    Jan. 26, 2012

Related U.S. Application Data

(62) Division of application No. 11/900,235, filed on Sep. 10, 2007, now Pat. No. 8,034,771.

(60) Provisional application No. 60/843,311, filed on Sep. 8, 2006.

(51) Int. Cl.
*A61K 38/19* (2006.01)
*A61K 38/16* (2006.01)
*C07K 14/54* (2006.01)

(52) U.S. Cl.
USPC ............................. 424/85.2; 514/12; 530/351

(58) Field of Classification Search
None
See application file for complete search history.

(56) References Cited

U.S. PATENT DOCUMENTS

| | | | |
|---|---|---|---|
| 4,751,180 A | 6/1988 | Cousens et al. |
| 4,816,567 A | 3/1989 | Cabilly et al. |
| 4,935,233 A | 6/1990 | Bell et al. |
| 5,011,912 A | 4/1991 | Hopp et al. |
| 5,457,035 A | 10/1995 | Baum et al. |
| 5,599,905 A | 2/1997 | Mosley et al. |
| 5,877,293 A | 3/1999 | Adair et al. |
| 5,886,152 A | 3/1999 | Nakatani et al. |
| 6,054,297 A | 4/2000 | Carter et al. |
| 6,660,843 B1 | 12/2003 | Feige et al. |
| 6,753,166 B2 | 6/2004 | Sims et al. |
| 6,838,290 B2 | 1/2005 | Sims et al. |
| 2002/0187122 A1 | 12/2002 | Sims et al. |
| 2006/0183161 A1 | 8/2006 | Nicklin et al. |

FOREIGN PATENT DOCUMENTS

| | | |
|---|---|---|
| JP | 2003523943 T | 8/2003 |
| WO | WO 93/10151 | 5/1993 |
| WO | WO 94/10308 | 5/1994 |
| WO | WO 98/42325 | 10/1998 |
| WO | 01/05974 A2 | 1/2001 |

OTHER PUBLICATIONS

Altman, et al., "Phenotypic Analysis of Antigen—Specific T Lymphocytes," Science, 1996, 274:94-96.

Ashkenazi, et al., "Protection against endotoxic shock by a tumor necrosis factor receptor immunoadhesin," Proc. Natl. Acad. Sci., 1991, 88:10535-10539.
Baron, et al., "Co-regulation of two gene activities by tetracycline via a bidirectional promoter," Nucl. Acids Res., 1995, 23(17):3605-3606.
Baum, et al. "Molecular characterization of murine and human OX40/OX40 ligand systems: identification of a human OX40 ligand . . . ," EMBO J., 1994, 13(17):3992-4001.
Blanar, et al., "Interaction Cloning: Identification of a Helix-Loop-Helix ZipperProtein that Interacts with c-Fos," Science, 1992, 256:1014-1018.
Born, et al., "Cloning of a Novel Receptor Subunit, AcPL, Required for Interleukin-18 Signaling," J. of Biol. Chem., 1998, 273(45):29445-29450.
Bowie, et al., "A Method to Identify Protein Sequences that Fold into a Known Three-Dimensional Structure," Science, 1991, 253:164-170.
Byrn, et al., "Biological properties of a CD4 immunoadhesin," Nature, 1990, 344:667-670.
Chalfie, et al., "Green Fluorescent Protein as a Marker for Gene Expression," Science, 1994, 263:802-805.
Debets, et al., "Two Novel IL-1 Family Members, IL-δ and IL-ε, Function . . . IL-1 Receptor-Related Protein 2," J. of Immunology, 2001, 167:1440-1446.
Dunn, et al., "Annotating genes with potential roles in the immune system: six new members of the IL-1 family," Trends in Immunol., 2001, 22 (10):533-536.
Dunn, et al., "High-Resolution Structure of Murine Interleukin 1 Homologue IL-1F5 Reveals Unique Loop Conformations for Receptor Binding . . . ," Biochem., 2003, 42:10938-10944.
Evans, et al., "Design of Nonpeptidal Ligands for a Peptide Receptor: Choloecystokinin Antagonists," J. Med. Chem., 1987, 30:1229-1239.
Fanslow, et al., "Structural characteristics of CD40 ligand that determine biological function," Seminars in Immunology, 1994, 6:267-278.
Fauchere, Jean-Luc, "Elements for the Rational Design of Peptide Drugs," Advances in Drug Research, 1996, 15:29-69.
Fiscella, et al., "TIP, a T-cell factor identified using high-throughput screening increases survival in a graft-versus-host disease model," Nature Biotech., 2003, 21:302-307.
Gluzman, Y., "SV40-Transformed Simian Cells Support the Replication of Early SV40 Mutants," Cell, 1981 23:175-182.
Hollenbaugh, et al., "Construction of Immunoglobulin Fusion Proteins," Current Protocols in Immunology, 1992, Suppl. 4, pp. 10.19.1-10.19.11.
Hopp, et al., "A Short Polypeptide Marker Sequence Useful for Recombinant Protein Identification and Purification," Bio/Technology, 1988, 6:1204-1210.
Hoppe, et al., "A parallel three stranded α-helical bundle at the nucleation site of collagen triple-helix formation," FEBS Letters, 1994, 344:191-195.
Humke, et al., "ICEBERG:A Novel Inhibitor of Interleukin-1β Generation," Cell, 2000, 103:99-111.
Korndörfer, et al., "Crystallographic Analysis of an 'Anticalin' with Tailored Specificity for Fluorescein Reveals...," Proteins:Struc. Func. and Bioinform., 2003, 53:121-129.

(Continued)

*Primary Examiner* — Ruixiang Li
(74) *Attorney, Agent, or Firm* — Mary Kymne Hehman; Patricia Anne Perkin

(57) ABSTRACT

The present invention provides compositions and methods relating to IL-1Rrp2 requiring proteins.

3 Claims, 2 Drawing Sheets

OTHER PUBLICATIONS

Kumar, Sanjay, "Identification and Initial Characterization of Four Novel Members of the Interleukin-1 Family," J. Biol. Chem., 2000, 275(14):10308-10314.

Landschulz, et al., "The Leucine Zipper: A Hypothetical Structure Common to a New Class of DNA Binding Proteins," Science, 1998, 240:1759-1764.

Lunde, et al., "Troybodies and Pepbodies", Biochemical Society Transations, 2002, 30:500-506.

Maniatis, et al., "Regulation of Inducible and Tissue-Specific Gene Expression," Science, 1987, 236:1237-1245.

McMahan, et al., "A novel IL-1 receptor, cloned from B cells by mammalian expression, is expressed in many cell types," EMBO J., 1991, 10(10):2821-2832.

Morrison, S.L., "Transfectomas Provide Novel Chimeric Antibodies," Science 1985, 229:1202-1207.

Ng, et al., "Differential effects of interleukin-1 β and transforming growth factor β1 on the expression of . . . ADAMTS-1 . . . ," Human Reproduction, 2006, 21(8):1990-1999.

Nicklin, et al., "A Sequence-Based Map of the Nine Genes of the Human Interleukin-1 Cluster," Genomics, 2002, 79 (5):718-725.

Paul, W.E., ed. Fundamental Immunology, 2$^{nd}$ Ed., Chapter 7, Du Pasquier, L., "Evolution of the Immune System," (Raven Press Ltd., New York, 1989), 139-165.

Rasmussen, et al., "Isolation, characterization and recombinant protein expression in Veggie-CHO: A serum-free CHO host cell line," Cytotechnology, 1998, 28:31-42.

Renshaw, et al., "Processing of Il-1 Family Members is Key to their Activity," Inflammation Research, 2007, 56(Suppl. 3):S430.

Rizo, et al., "Constrained Peptides: Models of Bioactive Peptides and Protein Substructures," Annu. Rev. Biochem., 1992, 61:387-418.

Roque, et al., "Antibodies and Genetically Engineered Related Molecules: Production and Purification," Biotechnol. Prog., 2004, 20:639-654.

Schier, et al., "Isolation of Picomolar Affinity Anti-cerbB-2 Single-chain Fv by Molecular Evolution . . . ," J.Mol. Biol., 1996, 263:551-567.

Schmitz, et al., "IL-33, an Interleukin-1 like Cytokine that Signals via the IL-1 Receptor-Related Protein ST2 & Induces T Helper Type 2-Assoc . . . ," Immunity, 2005, 23:479-490.

Sims, et al., "A new nomenclature for IL-1-family genes," Trends in Immunology, 2001, 22(10):536-537.

Smith, et al., "Four New Members Expand the Interleukin-1 Superfamily," J Biol. Chem., 2000, 275 (2):1169-1175.

Smith, et al., "Single-step purification of polypeptides expressed in *Escherichia coli* as fusions with glutathione S-transferase," Gene, 1988, 67:31-40.

Thornton, et al., "Prediction of progress at last," Nature, 1991, 354:105-106.

Towne, et al., "Interleukin IL-1F6,IL-1F8, and IL-1F9 Signal through IL-1Rrp2 and IL-1RAcP to Activate the Pathway . . . ," J. Biol. Chem., 2004, 279(14):13677-13688.

Urlaub, et al., "Isolation of Chinese hamster cell mutants deficient in dihydrofolate reductase activity," Proc. Natl. Acad. Sci., 1980, 77(7):4216-4220.

Verber, et al., "The design of metabolically-stable peptide analogs," Trends in Neurosciences, Sep. 1985, pp. 392-396.

Voss, et al., "The role of enhancers in the regulation of cell-type-specific transcriptional control," Trends Biochem. Sci. 11, Jul. 1986, 287-289.

FIG. 1

| Consensus | @XD | SEQ ID No |
|---|---|---|
| IL-1F5 | ~~~~~~~~~~~~~~MVLSGALCFRMKDSALKVLYLHNN | 44 |
| IL-1F6 | ~~~~~~~~~~~MEKALKIDTPQQGSIQDINHRVWVLQDQ | 59 |
| IL-1F8 | ~~~~~~~~~~~MNPQREAAPKSYAIRDSRQMVWVLSGN | 61 |
| IL-1F9 | MRGTPGDADGGGRAVYQSMCKPITGTINDLNQQVWTLQGQ | 63 |

FIG. 2

HuIL-1F5:

MVLSGALCFRMKDSALKVLYLHNNQLLAGGLHAGKVIKGEEISVVPNRWL
DASLSPVILGVQGGSQCLSCGVGQEPTLTLEPVNIMELYLGAKESKSFTF
YRRDMGLTSSFESAAYPGWFLCTVPEADQPVRLTQLPENGGWNAPITDFY
FQQCD (SEQ ID NO 1)

HuIL-1F6:

MEKALKIDTPQQGSIQDINHRVWVLQDQTLIAVPRKDRMSPVTIALISCR
HVETLEKDRGNPIYLGLNGLNLCLMCAKVGDQPTLQLKEKDIMDLYNQPE
PVKSFLFYHSQSGRNSTFESVAFPGWFIAVSSEGGCPLILTQELGKANTT
DFGLTMLF (SEQ ID NO 2)

HuIL-1F8:

MNPQREAAPKSYAIRDSRQMVWVLSGNSLIAAPLSRSIKPVTLHLIACRD
TEFSDKEKGNMVYLGIKGKDLCLFCAEIQGKPTLQLKEKNIMDLYVEKKA
QKPFLFFHNKEGSTSVFQSVSYPGWFIATSTTSGQPIFLTKERGITNNTN
FYLDSVE (SEQ ID NO 3)

HuIL-1F9:

MRGTPGDADGGGRAVYQSMCKPITGTINDLNQQVWTLQGQNLVAVPRS
DSVTPVTVAVITCKYPEALEQGRGDPIYLGIQNPEMCLYCEKVGEQPTLQ
LKEQKIMDLYGQPEPVKPFLFYRAKTGRTSTLESVAFPDWFIASSKRDQPII
LTSELGKSYNTAFELNIND (SEQ ID NO 4)

SEQUENCE LISTING

```
<160> NUMBER OF SEQ ID NOS: 78

<210> SEQ ID NO 1
<211> LENGTH: 155
<212> TYPE: PRT
<213> ORGANISM: Homo sapiens

<400> SEQUENCE: 1

Met Val Leu Ser Gly Ala Leu Cys Phe Arg Met Lys Asp Ser Ala Leu
1               5                   10                  15

Lys Val Leu Tyr Leu His Asn Asn Gln Leu Leu Ala Gly Gly Leu His
            20                  25                  30

Ala Gly Lys Val Ile Lys Gly Glu Glu Ile Ser Val Val Pro Asn Arg
        35                  40                  45

Trp Leu Asp Ala Ser Leu Ser Pro Val Ile Leu Gly Val Gln Gly Gly
    50                  55                  60

Ser Gln Cys Leu Ser Cys Gly Val Gly Gln Glu Pro Thr Leu Thr Leu
65                  70                  75                  80

Glu Pro Val Asn Ile Met Glu Leu Tyr Leu Gly Ala Lys Glu Ser Lys
```

```
                    85                  90                  95
Ser Phe Thr Phe Tyr Arg Arg Asp Met Gly Leu Thr Ser Ser Phe Glu
                100                 105                 110

Ser Ala Ala Tyr Pro Gly Trp Phe Leu Cys Thr Val Pro Glu Ala Asp
            115                 120                 125

Gln Pro Val Arg Leu Thr Gln Leu Pro Glu Asn Gly Gly Trp Asn Ala
        130                 135                 140

Pro Ile Thr Asp Phe Tyr Phe Gln Gln Cys Asp
145                 150                 155

<210> SEQ ID NO 2
<211> LENGTH: 158
<212> TYPE: PRT
<213> ORGANISM: Homo sapiens

<400> SEQUENCE: 2

Met Glu Lys Ala Leu Lys Ile Asp Thr Pro Gln Gln Gly Ser Ile Gln
1               5                   10                  15

Asp Ile Asn His Arg Val Trp Val Leu Gln Asp Gln Thr Leu Ile Ala
            20                  25                  30

Val Pro Arg Lys Asp Arg Met Ser Pro Val Thr Ile Ala Leu Ile Ser
        35                  40                  45

Cys Arg His Val Glu Thr Leu Glu Lys Asp Arg Gly Asn Pro Ile Tyr
    50                  55                  60

Leu Gly Leu Asn Gly Leu Asn Leu Cys Leu Met Cys Ala Lys Val Gly
65                  70                  75                  80

Asp Gln Pro Thr Leu Gln Leu Lys Glu Lys Asp Ile Met Asp Leu Tyr
                85                  90                  95

Asn Gln Pro Glu Pro Val Lys Ser Phe Leu Phe Tyr His Ser Gln Ser
                100                 105                 110

Gly Arg Asn Ser Thr Phe Glu Ser Val Ala Phe Pro Gly Trp Phe Ile
            115                 120                 125

Ala Val Ser Ser Glu Gly Gly Cys Pro Leu Ile Leu Thr Gln Glu Leu
        130                 135                 140

Gly Lys Ala Asn Thr Thr Asp Phe Gly Leu Thr Met Leu Phe
145                 150                 155

<210> SEQ ID NO 3
<211> LENGTH: 157
<212> TYPE: PRT
<213> ORGANISM: Homo sapiens

<400> SEQUENCE: 3

Met Asn Pro Gln Arg Glu Ala Ala Pro Lys Ser Tyr Ala Ile Arg Asp
1               5                   10                  15

Ser Arg Gln Met Val Trp Val Leu Ser Gly Asn Ser Leu Ile Ala Ala
            20                  25                  30

Pro Leu Ser Arg Ser Ile Lys Pro Val Thr Leu His Leu Ile Ala Cys
        35                  40                  45

Arg Asp Thr Glu Phe Ser Asp Lys Glu Lys Gly Asn Met Val Tyr Leu
    50                  55                  60

Gly Ile Lys Gly Lys Asp Leu Cys Leu Phe Cys Ala Glu Ile Gln Gly
65                  70                  75                  80

Lys Pro Thr Leu Gln Leu Lys Glu Lys Asn Ile Met Asp Leu Tyr Val
                85                  90                  95

Glu Lys Lys Ala Gln Lys Pro Phe Leu Phe Phe His Asn Lys Glu Gly
                100                 105                 110
```

```
Ser Thr Ser Val Phe Gln Ser Val Ser Tyr Pro Gly Trp Phe Ile Ala
        115                 120                 125

Thr Ser Thr Thr Ser Gly Gln Pro Ile Phe Leu Thr Lys Glu Arg Gly
130                 135                 140

Ile Thr Asn Asn Thr Asn Phe Tyr Leu Asp Ser Val Glu
145                 150                 155

<210> SEQ ID NO 4
<211> LENGTH: 169
<212> TYPE: PRT
<213> ORGANISM: Homo sapiens

<400> SEQUENCE: 4

Met Arg Gly Thr Pro Gly Asp Ala Asp Gly Gly Gly Arg Ala Val Tyr
1               5                   10                  15

Gln Ser Met Cys Lys Pro Ile Thr Gly Thr Ile Asn Asp Leu Asn Gln
            20                  25                  30

Gln Val Trp Thr Leu Gln Gly Gln Asn Leu Val Ala Val Pro Arg Ser
        35                  40                  45

Asp Ser Val Thr Pro Val Thr Val Ala Val Ile Thr Cys Lys Tyr Pro
50                  55                  60

Glu Ala Leu Glu Gln Gly Arg Gly Asp Pro Ile Tyr Leu Gly Ile Gln
65                  70                  75                  80

Asn Pro Glu Met Cys Leu Tyr Cys Glu Lys Val Gly Glu Gln Pro Thr
                85                  90                  95

Leu Gln Leu Lys Glu Gln Lys Ile Met Asp Leu Tyr Gly Gln Pro Glu
            100                 105                 110

Pro Val Lys Pro Phe Leu Phe Tyr Arg Ala Lys Thr Gly Arg Thr Ser
        115                 120                 125

Thr Leu Glu Ser Val Ala Phe Pro Asp Trp Phe Ile Ala Ser Ser Lys
130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165

<210> SEQ ID NO 5
<211> LENGTH: 8
<212> TYPE: PRT
<213> ORGANISM: Artificial
<220> FEATURE:
<223> OTHER INFORMATION: FLAG peptide

<400> SEQUENCE: 5

Asp Tyr Lys Asp Asp Asp Asp Lys
1               5

<210> SEQ ID NO 6
<211> LENGTH: 154
<212> TYPE: PRT
<213> ORGANISM: Homo sapiens

<400> SEQUENCE: 6

Val Leu Ser Gly Ala Leu Cys Phe Arg Met Lys Asp Ser Ala Leu Lys
1               5                   10                  15

Val Leu Tyr Leu His Asn Asn Gln Leu Leu Ala Gly Gly Leu His Ala
            20                  25                  30

Gly Lys Val Ile Lys Gly Glu Glu Ile Ser Val Val Pro Asn Arg Trp
        35                  40                  45
```

```
Leu Asp Ala Ser Leu Ser Pro Val Ile Leu Gly Val Gln Gly Gly Ser
         50                  55                  60

Gln Cys Leu Ser Cys Gly Val Gly Gln Glu Pro Thr Leu Thr Leu Glu
 65                  70                  75                  80

Pro Val Asn Ile Met Glu Leu Tyr Leu Gly Ala Lys Glu Ser Lys Ser
                 85                  90                  95

Phe Thr Phe Tyr Arg Arg Asp Met Gly Leu Thr Ser Ser Phe Glu Ser
                100                 105                 110

Ala Ala Tyr Pro Gly Trp Phe Leu Cys Thr Val Pro Glu Ala Asp Gln
            115                 120                 125

Pro Val Arg Leu Thr Gln Leu Pro Glu Asn Gly Gly Trp Asn Ala Pro
            130                 135                 140

Ile Thr Asp Phe Tyr Phe Gln Gln Cys Asp
145                 150
```

```
<210> SEQ ID NO 7
<211> LENGTH: 165
<212> TYPE: PRT
<213> ORGANISM: Homo sapiens
<220> FEATURE:
<221> NAME/KEY: MISC_FEATURE
<222> LOCATION: (155)..(162)
<223> OTHER INFORMATION: FLAG peptide tag
<220> FEATURE:
<221> NAME/KEY: MISC_FEATURE
<222> LOCATION: (163)..(165)
<223> OTHER INFORMATION: polyHis tag

<400> SEQUENCE: 7
```

```
Met Leu Ser Gly Ala Leu Cys Phe Arg Met Lys Asp Ser Ala Leu Lys
 1               5                  10                  15

Val Leu Tyr Leu His Asn Asn Gln Leu Leu Ala Gly Gly Leu His Ala
                 20                  25                  30

Gly Lys Val Ile Lys Gly Glu Glu Ile Ser Val Val Pro Asn Arg Trp
             35                  40                  45

Leu Asp Ala Ser Leu Ser Pro Val Ile Leu Gly Val Gln Gly Gly Ser
         50                  55                  60

Gln Cys Leu Ser Cys Gly Val Gly Gln Glu Pro Thr Leu Thr Leu Glu
 65                  70                  75                  80

Pro Val Asn Ile Met Glu Leu Tyr Leu Gly Ala Lys Glu Ser Lys Ser
                 85                  90                  95

Phe Thr Phe Tyr Arg Arg Asp Met Gly Leu Thr Ser Ser Phe Glu Ser
                100                 105                 110

Ala Ala Tyr Pro Gly Trp Phe Leu Cys Thr Val Pro Glu Ala Asp Gln
            115                 120                 125

Pro Val Arg Leu Thr Gln Leu Pro Glu Asn Gly Gly Trp Asn Ala Pro
            130                 135                 140

Ile Thr Asp Phe Tyr Phe Gln Gln Cys Asp Asp Tyr Lys Asp Asp Asp
145                 150                 155                 160

Asp Lys His His His
                165
```

```
<210> SEQ ID NO 8
<211> LENGTH: 154
<212> TYPE: PRT
<213> ORGANISM: Homo sapiens

<400> SEQUENCE: 8

Met Leu Ser Gly Ala Leu Cys Phe Arg Met Lys Asp Ser Ala Leu Lys
```

```
                1               5                  10                  15
Val Leu Tyr Leu His Asn Asn Gln Leu Leu Ala Gly Gly Leu His Ala
                    20                  25                  30

Gly Lys Val Ile Lys Gly Glu Glu Ile Ser Val Val Pro Asn Arg Trp
                    35                  40                  45

Leu Asp Ala Ser Leu Ser Pro Val Ile Leu Gly Val Gln Gly Gly Ser
            50                  55                  60

Gln Cys Leu Ser Cys Gly Val Gly Gln Glu Pro Thr Leu Thr Leu Glu
65                  70                  75                  80

Pro Val Asn Ile Met Glu Leu Tyr Leu Gly Ala Lys Glu Ser Lys Ser
                    85                  90                  95

Phe Thr Phe Tyr Arg Arg Asp Met Gly Leu Thr Ser Ser Phe Glu Ser
                    100                 105                 110

Ala Ala Tyr Pro Gly Trp Phe Leu Cys Thr Val Pro Glu Ala Asp Gln
                    115                 120                 125

Pro Val Arg Leu Thr Gln Leu Pro Glu Asn Gly Gly Trp Asn Ala Pro
                    130                 135                 140

Ile Thr Asp Phe Tyr Phe Gln Gln Cys Asp
145                 150

<210> SEQ ID NO 9
<211> LENGTH: 165
<212> TYPE: PRT
<213> ORGANISM: Homo sapiens
<220> FEATURE:
<221> NAME/KEY: MISC_FEATURE
<222> LOCATION: (155)..(162)
<223> OTHER INFORMATION: FLAG peptide tag
<220> FEATURE:
<221> NAME/KEY: MISC_FEATURE
<222> LOCATION: (163)..(165)
<223> OTHER INFORMATION: polyHis tag

<400> SEQUENCE: 9

Met Leu Ser Gly Ala Leu Cys Phe Arg Met Lys Asp Ser Ala Leu Lys
1               5                   10                  15

Val Leu Tyr Leu His Asn Asn Gln Leu Leu Ala Gly Gly Leu His Ala
                    20                  25                  30

Gly Lys Val Ile Lys Gly Glu Glu Ile Ser Val Val Pro Asn Arg Trp
                    35                  40                  45

Leu Asp Ala Ser Leu Ser Pro Val Ile Leu Gly Val Gln Gly Gly Ser
            50                  55                  60

Gln Cys Leu Ser Cys Gly Val Gly Gln Glu Pro Thr Leu Thr Leu Glu
65                  70                  75                  80

Pro Val Asn Ile Met Glu Leu Tyr Leu Gly Ala Lys Glu Ser Lys Ser
                    85                  90                  95

Phe Thr Phe Tyr Arg Arg Asp Met Gly Leu Thr Ser Ser Phe Glu Ser
                    100                 105                 110

Ala Ala Tyr Pro Gly Trp Phe Leu Cys Thr Val Pro Glu Ala Asp Gln
                    115                 120                 125

Pro Val Arg Leu Thr Gln Leu Pro Glu Asn Gly Gly Trp Asn Ala Pro
                    130                 135                 140

Ile Thr Asp Phe Tyr Phe Gln Gln Cys Asp Asp Tyr Lys Asp Asp
145                 150                 155                 160

Asp Lys His His His
                165

<210> SEQ ID NO 10
```

<211> LENGTH: 153
<212> TYPE: PRT
<213> ORGANISM: Homo sapiens

<400> SEQUENCE: 10

Lys Ile Asp Thr Pro Gln Gln Gly Ser Ile Gln Asp Ile Asn His Arg
1               5                   10                  15

Val Trp Val Leu Gln Asp Gln Thr Leu Ile Ala Val Pro Arg Lys Asp
            20                  25                  30

Arg Met Ser Pro Val Thr Ile Ala Leu Ile Ser Cys Arg His Val Glu
        35                  40                  45

Thr Leu Glu Lys Asp Arg Gly Asn Pro Ile Tyr Leu Gly Leu Asn Gly
    50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
    130                 135                 140

Thr Asp Phe Gly Leu Thr Met Leu Phe
145                 150

<210> SEQ ID NO 11
<211> LENGTH: 164
<212> TYPE: PRT
<213> ORGANISM: Homo sapiens
<220> FEATURE:
<221> NAME/KEY: MISC_FEATURE
<222> LOCATION: (154)..(161)
<223> OTHER INFORMATION: FLAG peptide tag
<220> FEATURE:
<221> NAME/KEY: MISC_FEATURE
<222> LOCATION: (162)..(164)
<223> OTHER INFORMATION: polyHis tag

<400> SEQUENCE: 11

Lys Ile Asp Thr Pro Gln Gln Gly Ser Ile Gln Asp Ile Asn His Arg
1               5                   10                  15

Val Trp Val Leu Gln Asp Gln Thr Leu Ile Ala Val Pro Arg Lys Asp
            20                  25                  30

Arg Met Ser Pro Val Thr Ile Ala Leu Ile Ser Cys Arg His Val Glu
        35                  40                  45

Thr Leu Glu Lys Asp Arg Gly Asn Pro Ile Tyr Leu Gly Leu Asn Gly
    50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
    130                 135                 140

Thr Asp Phe Gly Leu Thr Met Leu Phe Asp Tyr Lys Asp Asp Asp Asp

```
            145                 150                 155                 160
Lys His His His

<210> SEQ ID NO 12
<211> LENGTH: 153
<212> TYPE: PRT
<213> ORGANISM: Homo sapiens

<400> SEQUENCE: 12

Met Ile Asp Thr Pro Gln Gln Gly Ser Ile Gln Asp Ile Asn His Arg
1               5                   10                  15

Val Trp Val Leu Gln Asp Gln Thr Leu Ile Ala Val Pro Arg Lys Asp
            20                  25                  30

Arg Met Ser Pro Val Thr Ile Ala Leu Ile Ser Cys Arg His Val Glu
        35                  40                  45

Thr Leu Glu Lys Asp Arg Gly Asn Pro Ile Tyr Leu Gly Leu Asn Gly
    50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
    130                 135                 140

Thr Asp Phe Gly Leu Thr Met Leu Phe
145                 150

<210> SEQ ID NO 13
<211> LENGTH: 164
<212> TYPE: PRT
<213> ORGANISM: Homo sapiens
<220> FEATURE:
<221> NAME/KEY: MISC_FEATURE
<222> LOCATION: (154)..(161)
<223> OTHER INFORMATION: FLAG peptide tag
<220> FEATURE:
<221> NAME/KEY: MISC_FEATURE
<222> LOCATION: (162)..(164)
<223> OTHER INFORMATION: polyHis tag

<400> SEQUENCE: 13

Met Ile Asp Thr Pro Gln Gln Gly Ser Ile Gln Asp Ile Asn His Arg
1               5                   10                  15

Val Trp Val Leu Gln Asp Gln Thr Leu Ile Ala Val Pro Arg Lys Asp
            20                  25                  30

Arg Met Ser Pro Val Thr Ile Ala Leu Ile Ser Cys Arg His Val Glu
        35                  40                  45

Thr Leu Glu Lys Asp Arg Gly Asn Pro Ile Tyr Leu Gly Leu Asn Gly
    50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
```

```
            115                 120                 125
Gly Gly Cys Pro Leu Ile Leu Thr Gln Glu Leu Gly Lys Ala Asn Thr
        130                 135                 140

Thr Asp Phe Gly Leu Thr Met Leu Phe Asp Tyr Lys Asp Asp Asp Asp
145                 150                 155                 160

Lys His His His

<210> SEQ ID NO 14
<211> LENGTH: 153
<212> TYPE: PRT
<213> ORGANISM: Homo sapiens

<400> SEQUENCE: 14

Arg Glu Ala Ala Pro Lys Ser Tyr Ala Ile Arg Asp Ser Arg Gln Met
1               5                   10                  15

Val Trp Val Leu Ser Gly Asn Ser Leu Ile Ala Ala Pro Leu Ser Arg
            20                  25                  30

Ser Ile Lys Pro Val Thr Leu His Leu Ile Ala Cys Arg Asp Thr Glu
        35                  40                  45

Phe Ser Asp Lys Glu Lys Gly Asn Met Val Tyr Leu Gly Ile Lys Gly
    50                  55                  60

Lys Asp Leu Cys Leu Phe Cys Ala Glu Ile Gln Gly Lys Pro Thr Leu
65                  70                  75                  80

Gln Leu Lys Glu Lys Asn Ile Met Asp Leu Tyr Val Glu Lys Lys Ala
                85                  90                  95

Gln Lys Pro Phe Leu Phe His Asn Lys Glu Gly Ser Thr Ser Val
            100                 105                 110

Phe Gln Ser Val Ser Tyr Pro Gly Trp Phe Ile Ala Thr Ser Thr Thr
        115                 120                 125

Ser Gly Gln Pro Ile Phe Leu Thr Lys Glu Arg Gly Ile Thr Asn Asn
    130                 135                 140

Thr Asn Phe Tyr Leu Asp Ser Val Glu
145                 150

<210> SEQ ID NO 15
<211> LENGTH: 164
<212> TYPE: PRT
<213> ORGANISM: Homo sapiens
<220> FEATURE:
<221> NAME/KEY: MISC_FEATURE
<222> LOCATION: (154)..(161)
<223> OTHER INFORMATION: FLAG peptide tag
<220> FEATURE:
<221> NAME/KEY: MISC_FEATURE
<222> LOCATION: (162)..(164)
<223> OTHER INFORMATION: polyHis tag

<400> SEQUENCE: 15

Arg Glu Ala Ala Pro Lys Ser Tyr Ala Ile Arg Asp Ser Arg Gln Met
1               5                   10                  15

Val Trp Val Leu Ser Gly Asn Ser Leu Ile Ala Ala Pro Leu Ser Arg
            20                  25                  30

Ser Ile Lys Pro Val Thr Leu His Leu Ile Ala Cys Arg Asp Thr Glu
        35                  40                  45

Phe Ser Asp Lys Glu Lys Gly Asn Met Val Tyr Leu Gly Ile Lys Gly
    50                  55                  60

Lys Asp Leu Cys Leu Phe Cys Ala Glu Ile Gln Gly Lys Pro Thr Leu
65                  70                  75                  80

Gln Leu Lys Glu Lys Asn Ile Met Asp Leu Tyr Val Glu Lys Lys Ala
```

```
                 85                  90                  95
Gln Lys Pro Phe Leu Phe Phe His Asn Lys Glu Gly Ser Thr Ser Val
            100                 105                 110
Phe Gln Ser Val Ser Tyr Pro Gly Trp Phe Ile Ala Thr Ser Thr Thr
            115                 120                 125
Ser Gly Gln Pro Ile Phe Leu Thr Lys Glu Arg Gly Ile Thr Asn Asn
            130                 135                 140
Thr Asn Phe Tyr Leu Asp Ser Val Glu Asp Tyr Lys Asp Asp Asp Asp
145                 150                 155                 160
Lys His His His

<210> SEQ ID NO 16
<211> LENGTH: 153
<212> TYPE: PRT
<213> ORGANISM: Homo sapiens

<400> SEQUENCE: 16

Met Glu Ala Ala Pro Lys Ser Tyr Ala Ile Arg Asp Ser Arg Gln Met
1               5                   10                  15
Val Trp Val Leu Ser Gly Asn Ser Leu Ile Ala Ala Pro Leu Ser Arg
            20                  25                  30
Ser Ile Lys Pro Val Thr Leu His Leu Ile Ala Cys Arg Asp Thr Glu
        35                  40                  45
Phe Ser Asp Lys Glu Lys Gly Asn Met Val Tyr Leu Gly Ile Lys Gly
    50                  55                  60
Lys Asp Leu Cys Leu Phe Cys Ala Glu Ile Gln Gly Lys Pro Thr Leu
65                  70                  75                  80
Gln Leu Lys Glu Lys Asn Ile Met Asp Leu Tyr Val Glu Lys Lys Ala
                85                  90                  95
Gln Lys Pro Phe Leu Phe Phe His Asn Lys Glu Gly Ser Thr Ser Val
            100                 105                 110
Phe Gln Ser Val Ser Tyr Pro Gly Trp Phe Ile Ala Thr Ser Thr Thr
            115                 120                 125
Ser Gly Gln Pro Ile Phe Leu Thr Lys Glu Arg Gly Ile Thr Asn Asn
            130                 135                 140
Thr Asn Phe Tyr Leu Asp Ser Val Glu
145                 150

<210> SEQ ID NO 17
<211> LENGTH: 164
<212> TYPE: PRT
<213> ORGANISM: Homo sapiens
<220> FEATURE:
<221> NAME/KEY: MISC_FEATURE
<222> LOCATION: (154)..(161)
<223> OTHER INFORMATION: FLAG peptide tag
<220> FEATURE:
<221> NAME/KEY: MISC_FEATURE
<222> LOCATION: (162)..(164)
<223> OTHER INFORMATION: polyHis tag

<400> SEQUENCE: 17

Met Glu Ala Ala Pro Lys Ser Tyr Ala Ile Arg Asp Ser Arg Gln Met
1               5                   10                  15
Val Trp Val Leu Ser Gly Asn Ser Leu Ile Ala Ala Pro Leu Ser Arg
            20                  25                  30
Ser Ile Lys Pro Val Thr Leu His Leu Ile Ala Cys Arg Asp Thr Glu
        35                  40                  45
Phe Ser Asp Lys Glu Lys Gly Asn Met Val Tyr Leu Gly Ile Lys Gly
```

```
                50                  55                  60
Lys Asp Leu Cys Leu Phe Cys Ala Glu Ile Gln Gly Lys Pro Thr Leu
 65                  70                  75                  80

Gln Leu Lys Glu Lys Asn Ile Met Asp Leu Tyr Val Glu Lys Lys Ala
                 85                  90                  95

Gln Lys Pro Phe Leu Phe His Asn Lys Glu Gly Ser Thr Ser Val
            100                 105                 110

Phe Gln Ser Val Ser Tyr Pro Gly Trp Phe Ile Ala Thr Ser Thr Thr
            115                 120                 125

Ser Gly Gln Pro Ile Phe Leu Thr Lys Glu Arg Gly Ile Thr Asn Asn
130                 135                 140

Thr Asn Phe Tyr Leu Asp Ser Val Glu Asp Tyr Lys Asp Asp Asp Asp
145                 150                 155                 160

Lys His His His

<210> SEQ ID NO 18
<211> LENGTH: 152
<212> TYPE: PRT
<213> ORGANISM: Homo sapiens

<400> SEQUENCE: 18

Ser Met Cys Lys Pro Ile Thr Gly Thr Ile Asn Asp Leu Asn Gln Gln
 1               5                  10                  15

Val Trp Thr Leu Gln Gly Gln Asn Leu Val Ala Val Pro Arg Ser Asp
                20                  25                  30

Ser Val Thr Pro Val Thr Val Ala Val Ile Thr Cys Lys Tyr Pro Glu
            35                  40                  45

Ala Leu Glu Gln Gly Arg Gly Asp Pro Ile Tyr Leu Gly Ile Gln Asn
 50                  55                  60

Pro Glu Met Cys Leu Tyr Cys Glu Lys Val Gly Glu Gln Pro Thr Leu
 65                  70                  75                  80

Gln Leu Lys Glu Gln Lys Ile Met Asp Leu Tyr Gly Gln Pro Glu Pro
                 85                  90                  95

Val Lys Pro Phe Leu Phe Tyr Arg Ala Lys Thr Gly Thr Ser Thr
            100                 105                 110

Leu Glu Ser Val Ala Phe Pro Asp Trp Phe Ile Ala Ser Ser Lys Arg
            115                 120                 125

Asp Gln Pro Ile Ile Leu Thr Ser Glu Leu Gly Lys Ser Tyr Asn Thr
130                 135                 140

Ala Phe Glu Leu Asn Ile Asn Asp
145                 150

<210> SEQ ID NO 19
<211> LENGTH: 163
<212> TYPE: PRT
<213> ORGANISM: Homo sapiens
<220> FEATURE:
<221> NAME/KEY: MISC_FEATURE
<222> LOCATION: (153)..(160)
<223> OTHER INFORMATION: FLAG peptide tag
<220> FEATURE:
<221> NAME/KEY: MISC_FEATURE
<222> LOCATION: (161)..(163)
<223> OTHER INFORMATION: polyHis tag

<400> SEQUENCE: 19

Ser Met Cys Lys Pro Ile Thr Gly Thr Ile Asn Asp Leu Asn Gln Gln
 1               5                  10                  15

Val Trp Thr Leu Gln Gly Gln Asn Leu Val Ala Val Pro Arg Ser Asp
```

```
                    20                  25                  30
Ser Val Thr Pro Val Thr Val Ala Val Ile Thr Cys Lys Tyr Pro Glu
            35                  40                  45

Ala Leu Glu Gln Gly Arg Gly Asp Pro Ile Tyr Leu Gly Ile Gln Asn
        50                  55                  60

Pro Glu Met Cys Leu Tyr Cys Glu Lys Val Gly Glu Gln Pro Thr Leu
65                  70                  75                  80

Gln Leu Lys Glu Gln Lys Ile Met Asp Leu Tyr Gly Gln Pro Glu Pro
                85                  90                  95

Val Lys Pro Phe Leu Phe Tyr Arg Ala Lys Thr Gly Arg Thr Ser Thr
            100                 105                 110

Leu Glu Ser Val Ala Phe Pro Asp Trp Phe Ile Ala Ser Ser Lys Arg
        115                 120                 125

Asp Gln Pro Ile Ile Leu Thr Ser Glu Leu Gly Lys Ser Tyr Asn Thr
    130                 135                 140

Ala Phe Glu Leu Asn Ile Asn Asp Asp Tyr Lys Asp Asp Asp Lys
145                 150                 155                 160

His His His

<210> SEQ ID NO 20
<211> LENGTH: 152
<212> TYPE: PRT
<213> ORGANISM: Homo sapiens

<400> SEQUENCE: 20

Met Met Cys Lys Pro Ile Thr Gly Thr Ile Asn Asp Leu Asn Gln Gln
1               5                   10                  15

Val Trp Thr Leu Gln Gly Gln Asn Leu Val Ala Val Pro Arg Ser Asp
            20                  25                  30

Ser Val Thr Pro Val Thr Val Ala Val Ile Thr Cys Lys Tyr Pro Glu
        35                  40                  45

Ala Leu Glu Gln Gly Arg Gly Asp Pro Ile Tyr Leu Gly Ile Gln Asn
    50                  55                  60

Pro Glu Met Cys Leu Tyr Cys Glu Lys Val Gly Glu Gln Pro Thr Leu
65                  70                  75                  80

Gln Leu Lys Glu Gln Lys Ile Met Asp Leu Tyr Gly Gln Pro Glu Pro
                85                  90                  95

Val Lys Pro Phe Leu Phe Tyr Arg Ala Lys Thr Gly Arg Thr Ser Thr
            100                 105                 110

Leu Glu Ser Val Ala Phe Pro Asp Trp Phe Ile Ala Ser Ser Lys Arg
        115                 120                 125

Asp Gln Pro Ile Ile Leu Thr Ser Glu Leu Gly Lys Ser Tyr Asn Thr
    130                 135                 140

Ala Phe Glu Leu Asn Ile Asn Asp
145                 150

<210> SEQ ID NO 21
<211> LENGTH: 163
<212> TYPE: PRT
<213> ORGANISM: Homo sapiens
<220> FEATURE:
<221> NAME/KEY: MISC_FEATURE
<222> LOCATION: (153)..(160)
<223> OTHER INFORMATION: FLAG peptide tag
<220> FEATURE:
<221> NAME/KEY: MISC_FEATURE
<222> LOCATION: (161)..(163)
<223> OTHER INFORMATION: polyHis tag
```

<400> SEQUENCE: 21

```
Met Met Cys Lys Pro Ile Thr Gly Thr Ile Asn Asp Leu Asn Gln Gln
1               5                   10                  15

Val Trp Thr Leu Gln Gly Gln Asn Leu Val Ala Val Pro Arg Ser Asp
            20                  25                  30

Ser Val Thr Pro Val Thr Val Ala Val Ile Thr Cys Lys Tyr Pro Glu
        35                  40                  45

Ala Leu Glu Gln Gly Arg Gly Asp Pro Ile Tyr Leu Gly Ile Gln Asn
    50                  55                  60

Pro Glu Met Cys Leu Tyr Cys Glu Lys Val Gly Glu Gln Pro Thr Leu
65              70                  75                  80

Gln Leu Lys Glu Gln Lys Ile Met Asp Leu Tyr Gly Gln Pro Glu Pro
            85                  90                  95

Val Lys Pro Phe Leu Phe Tyr Arg Ala Lys Thr Gly Arg Thr Ser Thr
            100                 105                 110

Leu Glu Ser Val Ala Phe Pro Asp Trp Phe Ile Ala Ser Ser Lys Arg
            115                 120                 125

Asp Gln Pro Ile Ile Leu Thr Ser Glu Leu Gly Lys Ser Tyr Asn Thr
130                 135                 140

Ala Phe Glu Leu Asn Ile Asn Asp Asp Tyr Lys Asp Asp Asp Asp Lys
145                 150                 155                 160

His His His
```

<210> SEQ ID NO 22
<211> LENGTH: 172
<212> TYPE: PRT
<213> ORGANISM: Homo sapiens
<220> FEATURE:
<221> NAME/KEY: MISC_FEATURE
<222> LOCATION: (159)..(166)
<223> OTHER INFORMATION: FLAG peptide tag
<220> FEATURE:
<221> NAME/KEY: MISC_FEATURE
<222> LOCATION: (167)..(172)
<223> OTHER INFORMATION: polyHis tag

<400> SEQUENCE: 22

```
Met Glu Lys Ala Leu Lys Ile Asp Thr Pro Gln Gln Gly Ser Ile Gln
1               5                   10                  15

Asp Ile Asn His Arg Val Trp Val Leu Gln Asp Gln Thr Leu Ile Ala
            20                  25                  30

Val Pro Arg Lys Asp Arg Met Ser Pro Val Thr Ile Ala Leu Ile Ser
        35                  40                  45

Cys Arg His Val Glu Thr Leu Glu Lys Asp Arg Gly Asn Pro Ile Tyr
    50                  55                  60

Leu Gly Leu Asn Gly Leu Asn Leu Cys Leu Met Cys Ala Lys Val Gly
65              70                  75                  80

Asp Gln Pro Thr Leu Gln Leu Lys Glu Lys Asp Ile Met Asp Leu Tyr
            85                  90                  95

Asn Gln Pro Glu Pro Val Lys Ser Phe Leu Phe Tyr His Ser Gln Ser
            100                 105                 110

Gly Arg Asn Ser Thr Phe Glu Ser Val Ala Phe Pro Gly Trp Phe Ile
            115                 120                 125

Ala Val Ser Ser Glu Gly Gly Cys Pro Leu Ile Leu Thr Gln Glu Leu
130                 135                 140

Gly Lys Ala Asn Thr Thr Asp Phe Gly Leu Thr Met Leu Phe Asp Tyr
145                 150                 155                 160
```

```
Lys Asp Asp Asp Asp Lys His His His His His His
            165                 170
```

<210> SEQ ID NO 23
<211> LENGTH: 168
<212> TYPE: PRT
<213> ORGANISM: Homo sapiens
<220> FEATURE:
<221> NAME/KEY: MISC_FEATURE
<222> LOCATION: (155)..(162)
<223> OTHER INFORMATION: FLAG peptide tag
<220> FEATURE:
<221> NAME/KEY: MISC_FEATURE
<222> LOCATION: (163)..(168)
<223> OTHER INFORMATION: polyHis tag

<400> SEQUENCE: 23

```
Met Lys Ile Asp Thr Pro Gln Gln Gly Ser Ile Gln Asp Ile Asn His
1               5                   10                  15

Arg Val Trp Val Leu Gln Asp Gln Thr Leu Ile Ala Val Pro Arg Lys
            20                  25                  30

Asp Arg Met Ser Pro Val Thr Ile Ala Leu Ile Ser Cys Arg His Val
        35                  40                  45

Glu Thr Leu Glu Lys Asp Arg Gly Asn Pro Ile Tyr Leu Gly Leu Asn
50                  55                  60

Gly Leu Asn Leu Cys Leu Met Cys Ala Lys Val Gly Asp Gln Pro Thr
65                  70                  75                  80

Leu Gln Leu Lys Glu Lys Asp Ile Met Asp Leu Tyr Asn Gln Pro Glu
                85                  90                  95

Pro Val Lys Ser Phe Leu Phe Tyr His Ser Gln Ser Gly Arg Asn Ser
            100                 105                 110

Thr Phe Glu Ser Val Ala Phe Pro Gly Trp Phe Ile Ala Val Ser Ser
        115                 120                 125

Glu Gly Gly Cys Pro Leu Ile Leu Thr Gln Glu Leu Gly Lys Ala Asn
130                 135                 140

Thr Thr Asp Phe Gly Leu Thr Met Leu Phe Asp Tyr Lys Asp Asp Asp
145                 150                 155                 160

Asp Lys His His His His His His
            165
```

<210> SEQ ID NO 24
<211> LENGTH: 167
<212> TYPE: PRT
<213> ORGANISM: Homo sapiens
<220> FEATURE:
<221> NAME/KEY: MISC_FEATURE
<222> LOCATION: (154)..(161)
<223> OTHER INFORMATION: FLAG peptide tag
<220> FEATURE:
<221> NAME/KEY: MISC_FEATURE
<222> LOCATION: (162)..(167)
<223> OTHER INFORMATION: polyHis tag

<400> SEQUENCE: 24

```
Met Ile Asp Thr Pro Gln Gln Gly Ser Ile Gln Asp Ile Asn His Arg
1               5                   10                  15

Val Trp Val Leu Gln Asp Gln Thr Leu Ile Ala Val Pro Arg Lys Asp
            20                  25                  30

Arg Met Ser Pro Val Thr Ile Ala Leu Ile Ser Cys Arg His Val Glu
        35                  40                  45

Thr Leu Glu Lys Asp Arg Gly Asn Pro Ile Tyr Leu Gly Leu Asn Gly
50                  55                  60
```

```
Leu Asn Leu Cys Leu Met Cys Ala Lys Val Gly Asp Gln Pro Thr Leu
 65                  70                  75                  80

Gln Leu Lys Glu Lys Asp Ile Met Asp Leu Tyr Asn Gln Pro Glu Pro
                 85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
    130                 135                 140

Thr Asp Phe Gly Leu Thr Met Leu Phe Asp Tyr Lys Asp Asp Asp Asp
145                 150                 155                 160

Lys His His His His His His
                165

<210> SEQ ID NO 25
<211> LENGTH: 166
<212> TYPE: PRT
<213> ORGANISM: Homo sapiens
<220> FEATURE:
<221> NAME/KEY: MISC_FEATURE
<222> LOCATION: (153)..(160)
<223> OTHER INFORMATION: FLAG peptide tag
<220> FEATURE:
<221> NAME/KEY: MISC_FEATURE
<222> LOCATION: (161)..(166)
<223> OTHER INFORMATION: polyHis tag

<400> SEQUENCE: 25

Met Asp Thr Pro Gln Gln Gly Ser Ile Gln Asp Ile Asn His Arg Val
  1               5                  10                  15

Trp Val Leu Gln Asp Gln Thr Leu Ile Ala Val Pro Arg Lys Asp Arg
                 20                  25                  30

Met Ser Pro Val Thr Ile Ala Leu Ile Ser Cys Arg His Val Glu Thr
             35                  40                  45

Leu Glu Lys Asp Arg Gly Asn Pro Ile Tyr Leu Gly Leu Asn Gly Leu
         50                  55                  60

Asn Leu Cys Leu Met Cys Ala Lys Val Gly Asp Gln Pro Thr Leu Gln
 65                  70                  75                  80

Leu Lys Glu Lys Asp Ile Met Asp Leu Tyr Asn Gln Pro Glu Pro Val
                 85                  90                  95

Lys Ser Phe Leu Phe Tyr His Ser Gln Ser Gly Arg Asn Ser Thr Phe
            100                 105                 110

Glu Ser Val Ala Phe Pro Gly Trp Phe Ile Ala Val Ser Ser Glu Gly
        115                 120                 125

Gly Cys Pro Leu Ile Leu Thr Gln Glu Leu Gly Lys Ala Asn Thr Thr
    130                 135                 140

Asp Phe Gly Leu Thr Met Leu Phe Asp Tyr Lys Asp Asp Asp Asp Lys
145                 150                 155                 160

His His His His His His
                165

<210> SEQ ID NO 26
<211> LENGTH: 153
<212> TYPE: PRT
<213> ORGANISM: Homo sapiens

<400> SEQUENCE: 26

Lys Ile Asp Thr Pro Gln Gln Gly Ser Ile Gln Asp Ile Asn His Arg
  1               5                  10                  15
```

```
Val Trp Val Leu Gln Asp Gln Thr Leu Ile Ala Val Pro Arg Lys Asp
            20                  25                  30

Arg Met Ser Pro Val Thr Ile Ala Leu Ile Ser Cys Arg His Val Glu
            35                  40                  45

Thr Leu Glu Lys Asp Arg Gly Asn Pro Ile Tyr Leu Gly Leu Asn Gly
 50                  55                  60

Leu Asn Leu Cys Leu Met Cys Ala Lys Val Gly Asp Gln Pro Thr Leu
 65                  70                  75                  80

Gln Leu Lys Glu Lys Asp Ile Met Asp Leu Tyr Asn Gln Pro Glu Pro
            85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
            115                 120                 125

Gly Gly Cys Pro Leu Ile Leu Thr Gln Glu Leu Gly Lys Ala Asn Thr
            130                 135                 140

Thr Asp Phe Gly Leu Thr Met Leu Phe
145                 150

<210> SEQ ID NO 27
<211> LENGTH: 171
<212> TYPE: PRT
<213> ORGANISM: Homo sapiens
<220> FEATURE:
<221> NAME/KEY: MISC_FEATURE
<222> LOCATION: (158)..(165)
<223> OTHER INFORMATION: FLAG peptide tag
<220> FEATURE:
<221> NAME/KEY: MISC_FEATURE
<222> LOCATION: (166)..(171)
<223> OTHER INFORMATION: polyHis tag

<400> SEQUENCE: 27

Met Asn Pro Gln Arg Glu Ala Ala Pro Lys Ser Tyr Ala Ile Arg Asp
 1               5                  10                  15

Ser Arg Gln Met Val Trp Val Leu Ser Gly Asn Ser Leu Ile Ala Ala
            20                  25                  30

Pro Leu Ser Arg Ser Ile Lys Pro Val Thr Leu His Leu Ile Ala Cys
            35                  40                  45

Arg Asp Thr Glu Phe Ser Asp Lys Glu Lys Gly Asn Met Val Tyr Leu
 50                  55                  60

Gly Ile Lys Gly Lys Asp Leu Cys Leu Phe Cys Ala Glu Ile Gln Gly
 65                  70                  75                  80

Lys Pro Thr Leu Gln Leu Lys Glu Lys Asn Ile Met Asp Leu Tyr Val
            85                  90                  95

Glu Lys Lys Ala Gln Lys Pro Phe Leu Phe Phe His Asn Lys Glu Gly
            100                 105                 110

Ser Thr Ser Val Phe Gln Ser Val Ser Tyr Pro Gly Trp Phe Ile Ala
            115                 120                 125

Thr Ser Thr Thr Ser Gly Gln Pro Ile Phe Leu Thr Lys Glu Arg Gly
            130                 135                 140

Ile Thr Asn Asn Thr Asn Phe Tyr Leu Asp Ser Val Glu Asp Tyr Lys
145                 150                 155                 160

Asp Asp Asp Asp Lys His His His His His
            165                 170

<210> SEQ ID NO 28
<211> LENGTH: 169
```

```
<212> TYPE: PRT
<213> ORGANISM: Homo sapiens
<220> FEATURE:
<221> NAME/KEY: MISC_FEATURE
<222> LOCATION: (156)..(163)
<223> OTHER INFORMATION: FLAG peptide tag
<220> FEATURE:
<221> NAME/KEY: MISC_FEATURE
<222> LOCATION: (164)..(169)
<223> OTHER INFORMATION: polyHis tag

<400> SEQUENCE: 28
```

Met Gln Arg Glu Ala Ala Pro Lys Ser Tyr Ala Ile Arg Asp Ser Arg
1               5                   10                  15

Gln Met Val Trp Val Leu Ser Gly Asn Ser Leu Ile Ala Ala Pro Leu
            20                  25                  30

Ser Arg Ser Ile Lys Pro Val Thr Leu His Leu Ile Ala Cys Arg Asp
        35                  40                  45

Thr Glu Phe Ser Asp Lys Glu Lys Gly Asn Met Val Tyr Leu Gly Ile
50                  55                  60

Lys Gly Lys Asp Leu Cys Leu Phe Cys Ala Glu Ile Gln Gly Lys Pro
65                  70                  75                  80

Thr Leu Gln Leu Lys Glu Lys Asn Ile Met Asp Leu Tyr Val Glu Lys
                85                  90                  95

Lys Ala Gln Lys Pro Phe Leu Phe His Asn Lys Glu Gly Ser Thr
            100                 105                 110

Ser Val Phe Gln Ser Val Ser Tyr Pro Gly Trp Phe Ile Ala Thr Ser
        115                 120                 125

Thr Thr Ser Gly Gln Pro Ile Phe Leu Thr Lys Glu Arg Gly Ile Thr
130                 135                 140

Asn Asn Thr Asn Phe Tyr Leu Asp Ser Val Glu Asp Tyr Lys Asp Asp
145                 150                 155                 160

Asp Asp Lys His His His His His His
            165

```
<210> SEQ ID NO 29
<211> LENGTH: 168
<212> TYPE: PRT
<213> ORGANISM: Homo sapiens
<220> FEATURE:
<221> NAME/KEY: MISC_FEATURE
<222> LOCATION: (155)..(162)
<223> OTHER INFORMATION: FLAG peptide tag
<220> FEATURE:
<221> NAME/KEY: MISC_FEATURE
<222> LOCATION: (163)..(168)
<223> OTHER INFORMATION: polyHis tag

<400> SEQUENCE: 29
```

Met Arg Glu Ala Ala Pro Lys Ser Tyr Ala Ile Arg Asp Ser Arg Gln
1               5                   10                  15

Met Val Trp Val Leu Ser Gly Asn Ser Leu Ile Ala Ala Pro Leu Ser
            20                  25                  30

Arg Ser Ile Lys Pro Val Thr Leu His Leu Ile Ala Cys Arg Asp Thr
        35                  40                  45

Glu Phe Ser Asp Lys Glu Lys Gly Asn Met Val Tyr Leu Gly Ile Lys
50                  55                  60

Gly Lys Asp Leu Cys Leu Phe Cys Ala Glu Ile Gln Gly Lys Pro Thr
65                  70                  75                  80

Leu Gln Leu Lys Glu Lys Asn Ile Met Asp Leu Tyr Val Glu Lys Lys
                85                  90                  95

```
Ala Gln Lys Pro Phe Leu Phe His Asn Lys Glu Gly Ser Thr Ser
            100                 105                 110

Val Phe Gln Ser Val Ser Tyr Pro Gly Trp Phe Ile Ala Thr Ser Thr
            115                 120                 125

Thr Ser Gly Gln Pro Ile Phe Leu Thr Lys Glu Arg Gly Ile Thr Asn
        130                 135                 140

Asn Thr Asn Phe Tyr Leu Asp Ser Val Glu Asp Tyr Lys Asp Asp Asp
145                 150                 155                 160

Asp Lys His His His His His His
                165
```

<210> SEQ ID NO 30
<211> LENGTH: 167
<212> TYPE: PRT
<213> ORGANISM: Homo sapiens
<220> FEATURE:
<221> NAME/KEY: MISC_FEATURE
<222> LOCATION: (154)..(161)
<223> OTHER INFORMATION: FLAG peptide tag
<220> FEATURE:
<221> NAME/KEY: MISC_FEATURE
<222> LOCATION: (162)..(167)
<223> OTHER INFORMATION: polyHis tag

<400> SEQUENCE: 30

```
Met Glu Ala Ala Pro Lys Ser Tyr Ala Ile Arg Asp Ser Arg Gln Met
1               5                   10                  15

Val Trp Val Leu Ser Gly Asn Ser Leu Ile Ala Ala Pro Leu Ser Arg
            20                  25                  30

Ser Ile Lys Pro Val Thr Leu His Leu Ile Ala Cys Arg Asp Thr Glu
        35                  40                  45

Phe Ser Asp Lys Glu Lys Gly Asn Met Val Tyr Leu Gly Ile Lys Gly
    50                  55                  60

Lys Asp Leu Cys Leu Phe Cys Ala Glu Ile Gln Gly Lys Pro Thr Leu
65                  70                  75                  80

Gln Leu Lys Glu Lys Asn Ile Met Asp Leu Tyr Val Glu Lys Lys Ala
                85                  90                  95

Gln Lys Pro Phe Leu Phe His Asn Lys Glu Gly Ser Thr Ser Val
            100                 105                 110

Phe Gln Ser Val Ser Tyr Pro Gly Trp Phe Ile Ala Thr Ser Thr Thr
        115                 120                 125

Ser Gly Gln Pro Ile Phe Leu Thr Lys Glu Arg Gly Ile Thr Asn Asn
    130                 135                 140

Thr Asn Phe Tyr Leu Asp Ser Val Glu Asp Tyr Lys Asp Asp Asp Asp
145                 150                 155                 160

Lys His His His His His His
                165
```

<210> SEQ ID NO 31
<211> LENGTH: 165
<212> TYPE: PRT
<213> ORGANISM: Homo sapiens
<220> FEATURE:
<221> NAME/KEY: MISC_FEATURE
<222> LOCATION: (152)..(159)
<223> OTHER INFORMATION: FLAG peptide tag
<220> FEATURE:
<221> NAME/KEY: MISC_FEATURE
<222> LOCATION: (160)..(165)
<223> OTHER INFORMATION: polyHis tag

<400> SEQUENCE: 31

Ala Ala Pro Lys Ser Tyr Ala Ile Arg Asp Ser Arg Gln Met Val Trp
1               5                   10                  15

Val Leu Ser Gly Asn Ser Leu Ile Ala Pro Leu Ser Arg Ser Ile
            20                  25                  30

Lys Pro Val Thr Leu His Leu Ile Ala Cys Arg Asp Thr Glu Phe Ser
        35                  40                  45

Asp Lys Glu Lys Gly Asn Met Val Tyr Leu Gly Ile Lys Gly Lys Asp
    50                  55                  60

Leu Cys Leu Phe Cys Ala Glu Ile Gln Gly Lys Pro Thr Leu Gln Leu
65              70                  75                  80

Lys Glu Lys Asn Ile Met Asp Leu Tyr Val Lys Lys Ala Gln Lys
                85                  90                  95

Pro Phe Leu Phe Phe His Asn Lys Glu Gly Ser Thr Ser Val Phe Gln
            100                 105                 110

Ser Val Ser Tyr Pro Gly Trp Phe Ile Ala Thr Ser Thr Ser Gly
            115                 120                 125

Gln Pro Ile Phe Leu Thr Lys Glu Arg Gly Ile Thr Asn Asn Thr Asn
    130                 135                 140

Phe Tyr Leu Asp Ser Val Glu Asp Tyr Lys Asp Asp Asp Lys His
145                 150                 155                 160

His His His His His
            165

<210> SEQ ID NO 32
<211> LENGTH: 153
<212> TYPE: PRT
<213> ORGANISM: Homo sapiens

<400> SEQUENCE: 32

Arg Glu Ala Ala Pro Lys Ser Tyr Ala Ile Arg Asp Ser Arg Gln Met
1               5                   10                  15

Val Trp Val Leu Ser Gly Asn Ser Leu Ile Ala Ala Pro Leu Ser Arg
            20                  25                  30

Ser Ile Lys Pro Val Thr Leu His Leu Ile Ala Cys Arg Asp Thr Glu
        35                  40                  45

Phe Ser Asp Lys Glu Lys Gly Asn Met Val Tyr Leu Gly Ile Lys Gly
    50                  55                  60

Lys Asp Leu Cys Leu Phe Cys Ala Glu Ile Gln Gly Lys Pro Thr Leu
65              70                  75                  80

Gln Leu Lys Glu Lys Asn Ile Met Asp Leu Tyr Val Glu Lys Lys Ala
                85                  90                  95

Gln Lys Pro Phe Leu Phe Phe His Asn Lys Glu Gly Ser Thr Ser Val
            100                 105                 110

Phe Gln Ser Val Ser Tyr Pro Gly Trp Phe Ile Ala Thr Ser Thr Thr
            115                 120                 125

Ser Gly Gln Pro Ile Phe Leu Thr Lys Glu Arg Gly Ile Thr Asn Asn
    130                 135                 140

Thr Asn Phe Tyr Leu Asp Ser Val Glu
145                 150

<210> SEQ ID NO 33
<211> LENGTH: 183
<212> TYPE: PRT
<213> ORGANISM: Homo sapiens
<220> FEATURE:
<221> NAME/KEY: MISC_FEATURE
<222> LOCATION: (170)..(177)
<223> OTHER INFORMATION: FLAG peptide tag

```
-continued

<220> FEATURE:
<221> NAME/KEY: MISC_FEATURE
<222> LOCATION: (178)..(183)
<223> OTHER INFORMATION: polyHis tag

<400> SEQUENCE: 33

Met Arg Gly Thr Pro Gly Asp Ala Asp Gly Gly Arg Ala Val Tyr
1               5                   10                  15

Gln Ser Met Cys Lys Pro Ile Thr Gly Thr Ile Asn Asp Leu Asn Gln
            20                  25                  30

Gln Val Trp Thr Leu Gln Gly Gln Asn Leu Val Ala Val Pro Arg Ser
            35                  40                  45

Asp Ser Val Thr Pro Val Thr Val Ala Val Ile Thr Cys Lys Tyr Pro
    50                  55                  60

Glu Ala Leu Glu Gln Gly Arg Gly Asp Pro Ile Tyr Leu Gly Ile Gln
65              70                  75                  80

Asn Pro Glu Met Cys Leu Tyr Cys Glu Lys Val Gly Glu Gln Pro Thr
                85                  90                  95

Leu Gln Leu Lys Glu Gln Lys Ile Met Asp Leu Tyr Gly Gln Pro Glu
            100                 105                 110

Pro Val Lys Pro Phe Leu Phe Tyr Arg Ala Lys Thr Gly Arg Thr Ser
            115                 120                 125

Thr Leu Glu Ser Val Ala Phe Pro Asp Trp Phe Ile Ala Ser Ser Lys
    130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp Asp Tyr Lys Asp Asp Asp Asp
                165                 170                 175

Lys His His His His His His
            180

<210> SEQ ID NO 34
<211> LENGTH: 166
<212> TYPE: PRT
<213> ORGANISM: Homo sapiens
<220> FEATURE:
<221> NAME/KEY: MISC_FEATURE
<222> LOCATION: (153)..(160)
<223> OTHER INFORMATION: FLAG peptide tag
<220> FEATURE:
<221> NAME/KEY: MISC_FEATURE
<222> LOCATION: (161)..(166)
<223> OTHER INFORMATION: polyHis tag

<400> SEQUENCE: 34

Ser Met Cys Lys Pro Ile Thr Gly Thr Ile Asn Asp Leu Asn Gln Gln
1               5                   10                  15

Val Trp Thr Leu Gln Gly Gln Asn Leu Val Ala Val Pro Arg Ser Asp
            20                  25                  30

Ser Val Thr Pro Val Thr Val Ala Val Ile Thr Cys Lys Tyr Pro Glu
            35                  40                  45

Ala Leu Glu Gln Gly Arg Gly Asp Pro Ile Tyr Leu Gly Ile Gln Asn
    50                  55                  60

Pro Glu Met Cys Leu Tyr Cys Glu Lys Val Gly Glu Gln Pro Thr Leu
65              70                  75                  80

Gln Leu Lys Glu Gln Lys Ile Met Asp Leu Tyr Gly Gln Pro Glu Pro
            85                  90                  95

Val Lys Pro Phe Leu Phe Tyr Arg Ala Lys Thr Gly Arg Thr Ser Thr
            100                 105                 110
```

```
Leu Glu Ser Val Ala Phe Pro Asp Trp Phe Ile Ala Ser Ser Lys Arg
        115                 120                 125

Asp Gln Pro Ile Ile Leu Thr Ser Glu Leu Gly Lys Ser Tyr Asn Thr
    130                 135                 140

Ala Phe Glu Leu Asn Ile Asn Asp Asp Tyr Lys Asp Asp Asp Asp Lys
145                 150                 155                 160

His His His His His His
                165

<210> SEQ ID NO 35
<211> LENGTH: 166
<212> TYPE: PRT
<213> ORGANISM: Homo sapiens
<220> FEATURE:
<221> NAME/KEY: MISC_FEATURE
<222> LOCATION: (153)..(160)
<223> OTHER INFORMATION: FLAG peptide tag
<220> FEATURE:
<221> NAME/KEY: MISC_FEATURE
<222> LOCATION: (161)..(166)
<223> OTHER INFORMATION: polyHis tag

<400> SEQUENCE: 35

Met Met Cys Lys Pro Ile Thr Gly Thr Ile Asn Asp Leu Asn Gln Gln
1               5                   10                  15

Val Trp Thr Leu Gln Gly Gln Asn Leu Val Ala Val Pro Arg Ser Asp
            20                  25                  30

Ser Val Thr Pro Val Thr Val Ala Val Ile Thr Cys Lys Tyr Pro Glu
        35                  40                  45

Ala Leu Glu Gln Gly Arg Gly Asp Pro Ile Tyr Leu Gly Ile Gln Asn
50                  55                  60

Pro Glu Met Cys Leu Tyr Cys Glu Lys Val Gly Glu Gln Pro Thr Leu
65                  70                  75                  80

Gln Leu Lys Glu Gln Lys Ile Met Asp Leu Tyr Gly Gln Pro Glu Pro
                85                  90                  95

Val Lys Pro Phe Leu Phe Tyr Arg Ala Lys Thr Gly Arg Thr Ser Thr
            100                 105                 110

Leu Glu Ser Val Ala Phe Pro Asp Trp Phe Ile Ala Ser Ser Lys Arg
        115                 120                 125

Asp Gln Pro Ile Ile Leu Thr Ser Glu Leu Gly Lys Ser Tyr Asn Thr
    130                 135                 140

Ala Phe Glu Leu Asn Ile Asn Asp Asp Tyr Lys Asp Asp Asp Asp Lys
145                 150                 155                 160

His His His His His His
                165

<210> SEQ ID NO 36
<211> LENGTH: 164
<212> TYPE: PRT
<213> ORGANISM: Homo sapiens
<220> FEATURE:
<221> NAME/KEY: MISC_FEATURE
<222> LOCATION: (151)..(158)
<223> OTHER INFORMATION: FLAG peptide tag
<220> FEATURE:
<221> NAME/KEY: MISC_FEATURE
<222> LOCATION: (159)..(164)
<223> OTHER INFORMATION: polyHis tag

<400> SEQUENCE: 36

Cys Lys Pro Ile Thr Gly Thr Ile Asn Asp Leu Asn Gln Gln Val Trp
1               5                   10                  15
```

Thr Leu Gln Gly Gln Asn Leu Val Ala Val Pro Arg Ser Asp Ser Val
            20                  25                  30

Thr Pro Val Thr Val Ala Val Ile Thr Cys Lys Tyr Pro Glu Ala Leu
        35                  40                  45

Glu Gln Gly Arg Gly Asp Pro Ile Tyr Leu Gly Ile Gln Asn Pro Glu
 50                  55                  60

Met Cys Leu Tyr Cys Glu Lys Val Gly Glu Gln Pro Thr Leu Gln Leu
 65                  70                  75                  80

Lys Glu Gln Lys Ile Met Asp Leu Tyr Gly Gln Pro Glu Pro Val Lys
                 85                  90                  95

Pro Phe Leu Phe Tyr Arg Ala Lys Thr Gly Arg Thr Ser Thr Leu Glu
            100                 105                 110

Ser Val Ala Phe Pro Asp Trp Phe Ile Ala Ser Ser Lys Arg Asp Gln
        115                 120                 125

Pro Ile Ile Leu Thr Ser Glu Leu Gly Lys Ser Tyr Asn Thr Ala Phe
130                 135                 140

Glu Leu Asn Ile Asn Asp Asp Tyr Lys Asp Asp Asp Lys His His
145                 150                 155                 160

His His His His

<210> SEQ ID NO 37
<211> LENGTH: 152
<212> TYPE: PRT
<213> ORGANISM: Homo sapiens

<400> SEQUENCE: 37

Ser Met Cys Lys Pro Ile Thr Gly Thr Ile Asn Asp Leu Asn Gln Gln
1               5                   10                  15

Val Trp Thr Leu Gln Gly Gln Asn Leu Val Ala Val Pro Arg Ser Asp
            20                  25                  30

Ser Val Thr Pro Val Thr Val Ala Val Ile Thr Cys Lys Tyr Pro Glu
        35                  40                  45

Ala Leu Glu Gln Gly Arg Gly Asp Pro Ile Tyr Leu Gly Ile Gln Asn
 50                  55                  60

Pro Glu Met Cys Leu Tyr Cys Glu Lys Val Gly Glu Gln Pro Thr Leu
 65                  70                  75                  80

Gln Leu Lys Glu Gln Lys Ile Met Asp Leu Tyr Gly Gln Pro Glu Pro
                 85                  90                  95

Val Lys Pro Phe Leu Phe Tyr Arg Ala Lys Thr Gly Arg Thr Ser Thr
            100                 105                 110

Leu Glu Ser Val Ala Phe Pro Asp Trp Phe Ile Ala Ser Ser Lys Arg
        115                 120                 125

Asp Gln Pro Ile Ile Leu Thr Ser Glu Leu Gly Lys Ser Tyr Asn Thr
130                 135                 140

Ala Phe Glu Leu Asn Ile Asn Asp
145                 150

<210> SEQ ID NO 38
<211> LENGTH: 169
<212> TYPE: PRT
<213> ORGANISM: Homo sapiens
<220> FEATURE:
<221> NAME/KEY: MISC_FEATURE
<222> LOCATION: (156)..(163)
<223> OTHER INFORMATION: FLAG peptide tag
<220> FEATURE:
<221> NAME/KEY: MISC_FEATURE
<222> LOCATION: (164)..(169)
<223> OTHER INFORMATION: polyHis tag

<400> SEQUENCE: 38

```
Met Val Leu Ser Gly Ala Leu Cys Phe Arg Met Lys Asp Ser Ala Leu
1               5                   10                  15
Lys Val Leu Tyr Leu His Asn Asn Gln Leu Leu Ala Gly Gly Leu His
            20                  25                  30
Ala Gly Lys Val Ile Lys Gly Glu Glu Ile Ser Val Val Pro Asn Arg
        35                  40                  45
Trp Leu Asp Ala Ser Leu Ser Pro Val Ile Leu Gly Val Gln Gly Gly
    50                  55                  60
Ser Gln Cys Leu Ser Cys Gly Val Gly Gln Glu Pro Thr Leu Thr Leu
65                  70                  75                  80
Glu Pro Val Asn Ile Met Glu Leu Tyr Leu Gly Ala Lys Glu Ser Lys
                85                  90                  95
Ser Phe Thr Phe Tyr Arg Arg Asp Met Gly Leu Thr Ser Ser Phe Glu
            100                 105                 110
Ser Ala Ala Tyr Pro Gly Trp Phe Leu Cys Thr Val Pro Glu Ala Asp
        115                 120                 125
Gln Pro Val Arg Leu Thr Gln Leu Pro Glu Asn Gly Gly Trp Asn Ala
    130                 135                 140
Pro Ile Thr Asp Phe Tyr Phe Gln Gln Cys Asp Asp Tyr Lys Asp Asp
145                 150                 155                 160
Asp Asp Lys His His His His His His
                165
```

<210> SEQ ID NO 39
<211> LENGTH: 168
<212> TYPE: PRT
<213> ORGANISM: Homo sapiens
<220> FEATURE:
<221> NAME/KEY: MISC_FEATURE
<222> LOCATION: (155)..(162)
<223> OTHER INFORMATION: FLAG peptide tag
<220> FEATURE:
<221> NAME/KEY: MISC_FEATURE
<222> LOCATION: (163)..(168)
<223> OTHER INFORMATION: polyHis tag

<400> SEQUENCE: 39

```
Val Leu Ser Gly Ala Leu Cys Phe Arg Met Lys Asp Ser Ala Leu Lys
1               5                   10                  15
Val Leu Tyr Leu His Asn Asn Gln Leu Leu Ala Gly Gly Leu His Ala
            20                  25                  30
Gly Lys Val Ile Lys Gly Glu Glu Ile Ser Val Val Pro Asn Arg Trp
        35                  40                  45
Leu Asp Ala Ser Leu Ser Pro Val Ile Leu Gly Val Gln Gly Gly Ser
    50                  55                  60
Gln Cys Leu Ser Cys Gly Val Gly Gln Glu Pro Thr Leu Thr Leu Glu
65                  70                  75                  80
Pro Val Asn Ile Met Glu Leu Tyr Leu Gly Ala Lys Glu Ser Lys Ser
                85                  90                  95
Phe Thr Phe Tyr Arg Arg Asp Met Gly Leu Thr Ser Ser Phe Glu Ser
            100                 105                 110
Ala Ala Tyr Pro Gly Trp Phe Leu Cys Thr Val Pro Glu Ala Asp Gln
        115                 120                 125
Pro Val Arg Leu Thr Gln Leu Pro Glu Asn Gly Gly Trp Asn Ala Pro
    130                 135                 140
Ile Thr Asp Phe Tyr Phe Gln Gln Cys Asp Asp Tyr Lys Asp Asp Asp
```

```
                145                 150                 155                 160
Asp Lys His His His His His His
                165

<210> SEQ ID NO 40
<211> LENGTH: 168
<212> TYPE: PRT
<213> ORGANISM: Homo sapiens
<220> FEATURE:
<221> NAME/KEY: MISC_FEATURE
<222> LOCATION: (155)..(162)
<223> OTHER INFORMATION: FLAG peptide tag
<220> FEATURE:
<221> NAME/KEY: MISC_FEATURE
<222> LOCATION: (163)..(168)
<223> OTHER INFORMATION: polyHis tag

<400> SEQUENCE: 40

Met Leu Ser Gly Ala Leu Cys Phe Arg Met Lys Asp Ser Ala Leu Lys
1               5                   10                  15

Val Leu Tyr Leu His Asn Asn Gln Leu Leu Ala Gly Gly Leu His Ala
            20                  25                  30

Gly Lys Val Ile Lys Gly Glu Glu Ile Ser Val Val Pro Asn Arg Trp
        35                  40                  45

Leu Asp Ala Ser Leu Ser Pro Val Ile Leu Gly Val Gln Gly Gly Ser
    50                  55                  60

Gln Cys Leu Ser Cys Gly Val Gly Gln Glu Pro Thr Leu Thr Leu Glu
65                  70                  75                  80

Pro Val Asn Ile Met Glu Leu Tyr Leu Gly Ala Lys Glu Ser Lys Ser
                85                  90                  95

Phe Thr Phe Tyr Arg Arg Asp Met Gly Leu Thr Ser Ser Phe Glu Ser
            100                 105                 110

Ala Ala Tyr Pro Gly Trp Phe Leu Cys Thr Val Pro Glu Ala Asp Gln
        115                 120                 125

Pro Val Arg Leu Thr Gln Leu Pro Glu Asn Gly Gly Trp Asn Ala Pro
    130                 135                 140

Ile Thr Asp Phe Tyr Phe Gln Gln Cys Asp Asp Tyr Lys Asp Asp Asp
145                 150                 155                 160

Asp Lys His His His His His His
                165

<210> SEQ ID NO 41
<211> LENGTH: 166
<212> TYPE: PRT
<213> ORGANISM: Homo sapiens
<220> FEATURE:
<221> NAME/KEY: MISC_FEATURE
<222> LOCATION: (153)..(160)
<223> OTHER INFORMATION: FLAG peptide tag
<220> FEATURE:
<221> NAME/KEY: MISC_FEATURE
<222> LOCATION: (161)..(166)
<223> OTHER INFORMATION: polyHis tag

<400> SEQUENCE: 41

Ser Gly Ala Leu Cys Phe Arg Met Lys Asp Ser Ala Leu Lys Val Leu
1               5                   10                  15

Tyr Leu His Asn Asn Gln Leu Leu Ala Gly Gly Leu His Ala Gly Lys
            20                  25                  30

Val Ile Lys Gly Glu Glu Ile Ser Val Val Pro Asn Arg Trp Leu Asp
        35                  40                  45

Ala Ser Leu Ser Pro Val Ile Leu Gly Val Gln Gly Gly Ser Gln Cys
```

-continued

```
                50                  55                  60
Leu Ser Cys Gly Val Gly Gln Glu Pro Thr Leu Thr Leu Glu Pro Val
 65                  70                  75                  80

Asn Ile Met Glu Leu Tyr Leu Gly Ala Lys Glu Ser Lys Ser Phe Thr
                 85                  90                  95

Phe Tyr Arg Arg Asp Met Gly Leu Thr Ser Ser Phe Glu Ser Ala Ala
            100                 105                 110

Tyr Pro Gly Trp Phe Leu Cys Thr Val Pro Glu Ala Asp Gln Pro Val
        115                 120                 125

Arg Leu Thr Gln Leu Pro Glu Asn Gly Gly Trp Asn Ala Pro Ile Thr
    130                 135                 140

Asp Phe Tyr Phe Gln Gln Cys Asp Asp Tyr Lys Asp Asp Asp Asp Lys
145                 150                 155                 160

His His His His His His
                165

<210> SEQ ID NO 42
<211> LENGTH: 165
<212> TYPE: PRT
<213> ORGANISM: Homo sapiens
<220> FEATURE:
<221> NAME/KEY: MISC_FEATURE
<222> LOCATION: (152)..(159)
<223> OTHER INFORMATION: FLAG peptide tag
<220> FEATURE:
<221> NAME/KEY: MISC_FEATURE
<222> LOCATION: (160)..(165)
<223> OTHER INFORMATION: polyHis tag

<400> SEQUENCE: 42

Gly Ala Leu Cys Phe Arg Met Lys Asp Ser Ala Leu Lys Val Leu Tyr
 1               5                  10                  15

Leu His Asn Asn Gln Leu Leu Ala Gly Gly Leu His Ala Gly Lys Val
                 20                  25                  30

Ile Lys Gly Glu Glu Ile Ser Val Val Pro Asn Arg Trp Leu Asp Ala
             35                  40                  45

Ser Leu Ser Pro Val Ile Leu Gly Val Gln Gly Gly Ser Gln Cys Leu
        50                  55                  60

Ser Cys Gly Val Gly Gln Glu Pro Thr Leu Thr Leu Glu Pro Val Asn
 65                  70                  75                  80

Ile Met Glu Leu Tyr Leu Gly Ala Lys Glu Ser Lys Ser Phe Thr Phe
                 85                  90                  95

Tyr Arg Arg Asp Met Gly Leu Thr Ser Ser Phe Glu Ser Ala Ala Tyr
            100                 105                 110

Pro Gly Trp Phe Leu Cys Thr Val Pro Glu Ala Asp Gln Pro Val Arg
        115                 120                 125

Leu Thr Gln Leu Pro Glu Asn Gly Gly Trp Asn Ala Pro Ile Thr Asp
    130                 135                 140

Phe Tyr Phe Gln Gln Cys Asp Asp Tyr Lys Asp Asp Asp Asp Lys His
145                 150                 155                 160

His His His His His
                165

<210> SEQ ID NO 43
<211> LENGTH: 154
<212> TYPE: PRT
<213> ORGANISM: Homo sapiens

<400> SEQUENCE: 43
```

Val Leu Ser Gly Ala Leu Cys Phe Arg Met Lys Asp Ser Ala Leu Lys
1               5                   10                  15

Val Leu Tyr Leu His Asn Asn Gln Leu Leu Ala Gly Gly Leu His Ala
            20                  25                  30

Gly Lys Val Ile Lys Gly Glu Glu Ile Ser Val Val Pro Asn Arg Trp
            35                  40                  45

Leu Asp Ala Ser Leu Ser Pro Val Ile Leu Gly Val Gln Gly Gly Ser
        50                  55                  60

Gln Cys Leu Ser Cys Gly Val Gly Gln Glu Pro Thr Leu Thr Leu Glu
65                  70                  75                  80

Pro Val Asn Ile Met Glu Leu Tyr Leu Gly Ala Lys Glu Ser Lys Ser
                85                  90                  95

Phe Thr Phe Tyr Arg Arg Asp Met Gly Leu Thr Ser Ser Phe Glu Ser
                100                 105                 110

Ala Ala Tyr Pro Gly Trp Phe Leu Cys Thr Val Pro Glu Ala Asp Gln
            115                 120                 125

Pro Val Arg Leu Thr Gln Leu Pro Glu Asn Gly Gly Trp Asn Ala Pro
        130                 135                 140

Ile Thr Asp Phe Tyr Phe Gln Gln Cys Asp
145                 150

<210> SEQ ID NO 44
<211> LENGTH: 24
<212> TYPE: PRT
<213> ORGANISM: Homo sapiens

<400> SEQUENCE: 44

Met Val Leu Ser Gly Ala Leu Cys Phe Arg Met Lys Asp Ser Ala Leu
1               5                   10                  15

Lys Val Leu Tyr Leu His Asn Asn
            20

<210> SEQ ID NO 45
<211> LENGTH: 23
<212> TYPE: PRT
<213> ORGANISM: Homo sapiens

<400> SEQUENCE: 45

Val Leu Ser Gly Ala Leu Cys Phe Arg Met Lys Asp Ser Ala Leu Lys
1               5                   10                  15

Val Leu Tyr Leu His Asn Asn
            20

<210> SEQ ID NO 46
<211> LENGTH: 23
<212> TYPE: PRT
<213> ORGANISM: Homo sapiens

<400> SEQUENCE: 46

Met Leu Ser Gly Ala Leu Cys Phe Arg Met Lys Asp Ser Ala Leu Lys
1               5                   10                  15

Val Leu Tyr Leu His Asn Asn
            20

<210> SEQ ID NO 47
<211> LENGTH: 21
<212> TYPE: PRT
<213> ORGANISM: Homo sapiens

<400> SEQUENCE: 47

Ser Gly Ala Leu Cys Phe Arg Met Lys Asp Ser Ala Leu Lys Val Leu
1               5                   10                  15

Tyr Leu His Asn Asn
            20

<210> SEQ ID NO 48
<211> LENGTH: 20
<212> TYPE: PRT
<213> ORGANISM: Homo sapiens

<400> SEQUENCE: 48

Gly Ala Leu Cys Phe Arg Met Lys Asp Ser Ala Leu Lys Val Leu Tyr
1               5                   10                  15

Leu His Asn Asn
            20

<210> SEQ ID NO 49
<211> LENGTH: 24
<212> TYPE: PRT
<213> ORGANISM: Homo sapiens

<400> SEQUENCE: 49

Met Lys Ile Asp Thr Pro Gln Arg Gly Ser Ile Gln Asp Ile Asn His
1               5                   10                  15

Arg Val Trp Val Leu Gln Asp Gln
            20

<210> SEQ ID NO 50
<211> LENGTH: 23
<212> TYPE: PRT
<213> ORGANISM: Homo sapiens

<400> SEQUENCE: 50

Met Ile Asp Thr Pro Gln Arg Gly Ser Ile Gln Asp Ile Asn His Arg
1               5                   10                  15

Val Trp Val Leu Gln Asp Gln
            20

<210> SEQ ID NO 51
<211> LENGTH: 22
<212> TYPE: PRT
<213> ORGANISM: Homo sapiens

<400> SEQUENCE: 51

Met Asp Thr Pro Gln Arg Gly Ser Ile Gln Asp Ile Asn His Arg Val
1               5                   10                  15

Trp Val Leu Gln Asp Gln
            20

<210> SEQ ID NO 52
<211> LENGTH: 25
<212> TYPE: PRT
<213> ORGANISM: Homo sapiens

<400> SEQUENCE: 52

Met Gln Arg Glu Ala Ala Pro Lys Ser Tyr Ala Ile Arg Asp Ser Arg
1               5                   10                  15

Gln Met Val Trp Val Leu Ser Gly Asn
            20                  25

<210> SEQ ID NO 53
<211> LENGTH: 24
<212> TYPE: PRT

<213> ORGANISM: Homo sapiens

<400> SEQUENCE: 53

Met Arg Glu Ala Ala Pro Lys Ser Tyr Ala Ile Arg Asp Ser Arg Gln
1               5                   10                  15

Met Val Trp Val Leu Ser Gly Asn
            20

<210> SEQ ID NO 54
<211> LENGTH: 23
<212> TYPE: PRT
<213> ORGANISM: Homo sapiens

<400> SEQUENCE: 54

Met Glu Ala Ala Pro Lys Ser Tyr Ala Ile Arg Asp Ser Arg Gln Met
1               5                   10                  15

Val Trp Val Leu Ser Gly Asn
            20

<210> SEQ ID NO 55
<211> LENGTH: 21
<212> TYPE: PRT
<213> ORGANISM: Homo sapiens

<400> SEQUENCE: 55

Ala Ala Pro Lys Ser Tyr Ala Ile Arg Asp Ser Arg Gln Met Val Trp
1               5                   10                  15

Val Leu Ser Gly Asn
            20

<210> SEQ ID NO 56
<211> LENGTH: 23
<212> TYPE: PRT
<213> ORGANISM: Homo sapiens

<400> SEQUENCE: 56

Ser Met Cys Lys Pro Ile Thr Gly Thr Ile Asn Asp Leu Asn Gln Gln
1               5                   10                  15

Val Trp Thr Leu Gln Gly Gln
            20

<210> SEQ ID NO 57
<211> LENGTH: 23
<212> TYPE: PRT
<213> ORGANISM: Homo sapiens

<400> SEQUENCE: 57

Met Met Cys Lys Pro Ile Thr Gly Thr Ile Asn Asp Leu Asn Gln Gln
1               5                   10                  15

Val Trp Thr Leu Gln Gly Gln
            20

<210> SEQ ID NO 58
<211> LENGTH: 21
<212> TYPE: PRT
<213> ORGANISM: Homo sapiens

<400> SEQUENCE: 58

Cys Lys Pro Ile Thr Gly Thr Ile Asn Asp Leu Asn Gln Gln Val Trp
1               5                   10                  15

Thr Leu Gln Gly Gln
            20

<210> SEQ ID NO 59
<211> LENGTH: 28
<212> TYPE: PRT
<213> ORGANISM: Homo sapiens

<400> SEQUENCE: 59

Met Glu Lys Ala Leu Lys Ile Asp Thr Pro Gln Gln Gly Ser Ile Gln
1               5                   10                  15

Asp Ile Asn His Arg Val Trp Val Leu Gln Asp Gln
            20                  25

<210> SEQ ID NO 60
<211> LENGTH: 23
<212> TYPE: PRT
<213> ORGANISM: Homo sapiens

<400> SEQUENCE: 60

Lys Ile Asp Thr Pro Gln Gln Gly Ser Ile Gln Asp Ile Asn His Arg
1               5                   10                  15

Val Trp Val Leu Gln Asp Gln
            20

<210> SEQ ID NO 61
<211> LENGTH: 27
<212> TYPE: PRT
<213> ORGANISM: Homo sapiens

<400> SEQUENCE: 61

Met Asn Pro Gln Arg Glu Ala Ala Pro Lys Ser Tyr Ala Ile Arg Asp
1               5                   10                  15

Ser Arg Gln Met Val Trp Val Leu Ser Gly Asn
            20                  25

<210> SEQ ID NO 62
<211> LENGTH: 23
<212> TYPE: PRT
<213> ORGANISM: Homo sapiens

<400> SEQUENCE: 62

Arg Glu Ala Ala Pro Lys Ser Tyr Ala Ile Arg Asp Ser Arg Gln Met
1               5                   10                  15

Val Trp Val Leu Ser Gly Asn
            20

<210> SEQ ID NO 63
<211> LENGTH: 40
<212> TYPE: PRT
<213> ORGANISM: Homo sapiens

<400> SEQUENCE: 63

Met Arg Gly Thr Pro Gly Asp Ala Asp Gly Gly Gly Arg Ala Val Tyr
1               5                   10                  15

Gln Ser Met Cys Lys Pro Ile Thr Gly Thr Ile Asn Asp Leu Asn Gln
            20                  25                  30

Gln Val Trp Thr Leu Gln Gly Gln
        35                  40

<210> SEQ ID NO 64

<400> SEQUENCE: 64

000

```
<210> SEQ ID NO 65
<211> LENGTH: 153
<212> TYPE: PRT
<213> ORGANISM: Homo sapiens

<400> SEQUENCE: 65

Lys Ile Asp Thr Pro Gln Arg Gly Ser Ile Gln Asp Ile Asn His Arg
1               5                   10                  15

Val Trp Val Leu Gln Asp Gln Thr Leu Ile Ala Val Pro Arg Lys Asp
            20                  25                  30

Arg Met Ser Pro Val Thr Ile Ala Leu Ile Ser Cys Arg His Val Glu
        35                  40                  45

Thr Leu Glu Lys Asp Arg Gly Asn Pro Ile Tyr Leu Gly Leu Asn Gly
    50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
    130                 135                 140

Thr Asp Phe Gly Leu Thr Met Leu Phe
145                 150

<210> SEQ ID NO 66
<211> LENGTH: 164
<212> TYPE: PRT
<213> ORGANISM: Homo sapiens
<220> FEATURE:
<221> NAME/KEY: MISC_FEATURE
<222> LOCATION: (154)..(161)
<223> OTHER INFORMATION: FLAG peptide tag
<220> FEATURE:
<221> NAME/KEY: MISC_FEATURE
<222> LOCATION: (162)..(164)
<223> OTHER INFORMATION: polyHis tag

<400> SEQUENCE: 66

Lys Ile Asp Thr Pro Gln Arg Gly Ser Ile Gln Asp Ile Asn His Arg
1               5                   10                  15

Val Trp Val Leu Gln Asp Gln Thr Leu Ile Ala Val Pro Arg Lys Asp
            20                  25                  30

Arg Met Ser Pro Val Thr Ile Ala Leu Ile Ser Cys Arg His Val Glu
        35                  40                  45

Thr Leu Glu Lys Asp Arg Gly Asn Pro Ile Tyr Leu Gly Leu Asn Gly
    50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
    130                 135                 140
```

```
Thr Asp Phe Gly Leu Thr Met Leu Phe Asp Tyr Lys Asp Asp Asp
145                 150                 155                 160

Lys His His His

<210> SEQ ID NO 67
<211> LENGTH: 153
<212> TYPE: PRT
<213> ORGANISM: Homo sapiens

<400> SEQUENCE: 67

Met Ile Asp Thr Pro Gln Arg Gly Ser Ile Gln Asp Ile Asn His Arg
1               5                   10                  15

Val Trp Val Leu Gln Asp Gln Thr Leu Ile Ala Val Pro Arg Lys Asp
                20                  25                  30

Arg Met Ser Pro Val Thr Ile Ala Leu Ile Ser Cys Arg His Val Glu
            35                  40                  45

Thr Leu Glu Lys Asp Arg Gly Asn Pro Ile Tyr Leu Gly Leu Asn Gly
        50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
130                 135                 140

Thr Asp Phe Gly Leu Thr Met Leu Phe
145                 150

<210> SEQ ID NO 68
<211> LENGTH: 164
<212> TYPE: PRT
<213> ORGANISM: Homo sapiens
<220> FEATURE:
<221> NAME/KEY: MISC_FEATURE
<222> LOCATION: (154)..(161)
<223> OTHER INFORMATION: FLAG peptide tag
<220> FEATURE:
<221> NAME/KEY: MISC_FEATURE
<222> LOCATION: (162)..(164)
<223> OTHER INFORMATION: polyHis tag

<400> SEQUENCE: 68

Met Ile Asp Thr Pro Gln Arg Gly Ser Ile Gln Asp Ile Asn His Arg
1               5                   10                  15

Val Trp Val Leu Gln Asp Gln Thr Leu Ile Ala Val Pro Arg Lys Asp
                20                  25                  30

Arg Met Ser Pro Val Thr Ile Ala Leu Ile Ser Cys Arg His Val Glu
            35                  40                  45

Thr Leu Glu Lys Asp Arg Gly Asn Pro Ile Tyr Leu Gly Leu Asn Gly
        50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110
```

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
130                 135                 140

Thr Asp Phe Gly Leu Thr Met Leu Phe Asp Tyr Lys Asp Asp Asp Asp
145                 150                 155                 160

Lys His His His

<210> SEQ ID NO 69
<211> LENGTH: 465
<212> TYPE: DNA
<213> ORGANISM: Homo sapiens

<400> SEQUENCE: 69

| gtcctgagtg gggcgctgtg cttccgaatg aaggactcgg cattgaaggt gctttatctg | 60 |
| cataataacc agcttctagc tggagggctg catgcaggga aggtcattaa aggtgaagag | 120 |
| atcagcgtgg tccccaatcg gtggctggat gccagcctgt cccccgtcat cctgggtgtc | 180 |
| cagggtggaa gccagtgcct gtcatgtggg gtggggcagg agccgactct aacactagag | 240 |
| ccagtgaaca tcatggagct ctatcttggt gccaaggaat ccaagagctt caccttctac | 300 |
| cggcgggaca tggggctcac ctccagcttc gagtcggctg cctacccggg ctggttcctg | 360 |
| tgcacggtgc ctgaagccga tcagcctgtc agactcaccc agcttcccga gaatggtggc | 420 |
| tggaatgccc ccatcacaga cttctacttc agcagtgtg actaa | 465 |

<210> SEQ ID NO 70
<211> LENGTH: 531
<212> TYPE: DNA
<213> ORGANISM: Homo sapiens

<400> SEQUENCE: 70

| atgctgagtg gggcgctgtg cttccgaatg aaggactcgg cattgaaggt gctttatctg | 60 |
| cataataacc agcttctagc tggagggctg catgcaggga aggtcattaa aggtgaagag | 120 |
| atcagcgtgg tccccaatcg gtggctggat gccagcctgt cccccgtcat cctgggtgtc | 180 |
| cagggtggaa gccagtgcct gtcatgtggg gtggggcagg agccgactct aacactagag | 240 |
| ccagtgaaca tcatggagct ctatcttggt gccaaggaat ccaagagctt caccttctac | 300 |
| cggcgggaca tggggctcac ctccagcttc gagtcggctg cctacccggg ctggttcctg | 360 |
| tgcacggtgc ctgaagccga tcagcctgtc agactcaccc agcttcccga gaatggtggc | 420 |
| tggaatgccc ccatcacaga cttctacttc agcagtgtg acagatctgg cagttctgac | 480 |
| tacaaggacg acgacgacaa gggcagttct caccatcacc atcaccacta g | 531 |

<210> SEQ ID NO 71
<211> LENGTH: 462
<212> TYPE: DNA
<213> ORGANISM: Homo sapiens

<400> SEQUENCE: 71

| aaaattgaca cacctcagcg ggggagcatt caggatatca atcatcgggt gtgggttctt | 60 |
| caggaccaga cgctcatagc agtcccgagg aaggaccgta tgtctccagt cactattgcc | 120 |
| ttaatctcat gccgacatgt ggagacccttt gagaaagaca gagggaaccc catctacctg | 180 |
| ggcctgaatg gactcaatct ctgcctgatg tgtgctaaag tcgggacca gcccacactg | 240 |
| cagctgaagg aaaaggatat aatggatttg tacaaccaac ccgagcctgt gaagtccttt | 300 |

| | |
|---|---|
| ctcttctacc acagccagag tggcaggaac tccaccttcg agtctgtggc tttccctggc | 360 |
| tggttcatcg ctgtcagctc tgaaggaggc tgtcctctca tccttaccca agaactgggg | 420 |
| aaagccaaca ctactgactt tgggttaact atgctgtttt aa | 462 |

<210> SEQ ID NO 72
<211> LENGTH: 528
<212> TYPE: DNA
<213> ORGANISM: Homo sapiens
<400> SEQUENCE: 72

| | |
|---|---|
| atgattgaca caccctcagcg gggagcatt caggatatca atcatcgggt gtgggttctt | 60 |
| caggaccaga cgctcatagc agtcccgagg aaggaccgta tgtctccagt cactattgcc | 120 |
| ttaatctcat gccgacatgt ggagacccctt gagaaagaca gagggaaccc catctacctg | 180 |
| ggcctgaatg gactcaatct ctgcctgatg tgtgctaaag tcggggacca gcccacactg | 240 |
| cagctgaagg aaaaggatat aatggatttg tacaaccaac ccgagcctgt gaagtccttt | 300 |
| ctcttctacc acagccagag tggcaggaac tccaccttcg agtctgtggc tttccctggc | 360 |
| tggttcatcg ctgtcagctc tgaaggaggc tgtcctctca tccttaccca agaactgggg | 420 |
| aaagccaaca ctactgactt tgggttaact atgctgttta gatctggcag ttctgactac | 480 |
| aaggacgacg acgacaaggg cagttctcac catcaccatc accactag | 528 |

<210> SEQ ID NO 73
<211> LENGTH: 462
<212> TYPE: DNA
<213> ORGANISM: Homo sapiens
<400> SEQUENCE: 73

| | |
|---|---|
| cgcgaggcag cacccaaatc ctatgctatt cgtgattctc acagatggt gtgggtcctg | 60 |
| agtggaaatt ctttaatagc agctcctctt agccgcagca ttaagcctgt cactcttcat | 120 |
| ttaatagcct gtagagacac agaattcagt gacaaggaaa agggtaatat ggtttacctg | 180 |
| ggaatcaagg gaaagatct ctgtctcttc tgtgcagaaa ttcagggcaa gcctactttg | 240 |
| cagcttaagg aaaaaaatat catggacctg tatgtgagaa agaaagcaca gaagcccttt | 300 |
| ctcttttttcc acaataaaga aggctccact tctgtctttc agtcagtctc ttaccctggc | 360 |
| tggttcatag ccacctccac cacatcagga cagcccatct ttctcaccaa ggagagaggc | 420 |
| ataactaata acactaactt ctacttagat tctgtggaat aa | 462 |

<210> SEQ ID NO 74
<211> LENGTH: 528
<212> TYPE: DNA
<213> ORGANISM: Homo sapiens
<400> SEQUENCE: 74

| | |
|---|---|
| atggaggcag cacccaaatc ctatgctatt cgtgattctc acagatggt gtgggtcctg | 60 |
| agtggaaatt ctttaatagc agctcctctt agccgcagca ttaagcctgt cactcttcat | 120 |
| ttaatagcct gtagagacac agaattcagt gacaaggaaa agggtaatat ggtttacctg | 180 |
| ggaatcaagg gaaagatct ctgtctcttc tgtgcagaaa ttcagggcaa gcctactttg | 240 |
| cagcttaagg aaaaaaatat catggacctg tatgtgagaa agaaagcaca gaagcccttt | 300 |
| ctcttttttcc acaataaaga aggctccact tctgtctttc agtcagtctc ttaccctggc | 360 |
| tggttcatag ccacctccac cacatcagga cagcccatct ttctcaccaa ggagagaggc | 420 |
| ataactaata acactaactt ctacttagat tctgtggaag gatctggcag ttctgactac | 480 |

| aaggacgacg acgacaaggg cagttctcac catcaccatc accactag | 528 |

<210> SEQ ID NO 75
<211> LENGTH: 459
<212> TYPE: DNA
<213> ORGANISM: Homo sapiens
<400> SEQUENCE: 75

| tcaatgtgta aacctattac tgggactatt aatgatttga atcagcaagt gtggacccett | 60 |
| cagggtcaga accttgtggc agttccacga agtgacagtg tgaccccagt cactgttgct | 120 |
| gttatcacat gcaagtatcc agaggctctt gagcaaggca gagggatcc catttatttg | 180 |
| ggaatccaga atccagaaat gtgtttgtat tgtgagaagg ttggagaaca gcccacattg | 240 |
| cagctaaaag agcagaagat catggatctg tatggccaac ccgagcccgt gaaacccttc | 300 |
| cttttctacc gtgccaagac tggtaggacc tccaccctg agtctgtggc cttccccggac | 360 |
| tggttcattg cctcctccaa gagagaccag cccatcattc tgacttcaga acttgggaag | 420 |
| tcatacaaca ctgcctttga attaaatata aatgactaa | 459 |

<210> SEQ ID NO 76
<211> LENGTH: 528
<212> TYPE: DNA
<213> ORGANISM: Homo sapiens
<400> SEQUENCE: 76

| atgtcaatgt gtaaacctat tactgggact attaatgatt tgaatcagca agtgtggacc | 60 |
| cttcagggtc agaaccttgt ggcagttcca cgaagtgaca gtgtgacccc agtcactgtt | 120 |
| gctgttatca catgcaagta tccagaggct cttgagcaag gcagagggga tcccatttat | 180 |
| ttgggaatcc agaatccaga aatgtgtttg tattgtgaga aggttggaga acagcccaca | 240 |
| ttgcagctaa aagagcagaa gatcatggat ctgtatggcc aacccgagcc cgtgaaaccc | 300 |
| ttcctttct accgtgccaa gactggtagg acctccaccc ttgagtctgt ggccttcccg | 360 |
| gactggttca ttgcctcctc caagagagac cagcccatca ttctgacttc agaacttggg | 420 |
| aagtcataca cactgccttt gaattaaat ataaatgaca gatctggcag ttctgactac | 480 |
| aaggacgacg acgacaaggg cagttctcac catcaccatc accactag | 528 |

<210> SEQ ID NO 77
<211> LENGTH: 525
<212> TYPE: DNA
<213> ORGANISM: Homo sapiens
<400> SEQUENCE: 77

| atgatgtgta aacctattac tgggactatt aatgatttga atcagcaagt gtggacccett | 60 |
| cagggtcaga accttgtggc agttccacga agtgacagtg tgaccccagt cactgttgct | 120 |
| gttatcacat gcaagtatcc agaggctctt gagcaaggca gagggatcc catttatttg | 180 |
| ggaatccaga atccagaaat gtgtttgtat tgtgagaagg ttggagaaca gcccacattg | 240 |
| cagctaaaag agcagaagat catggatctg tatggccaac ccgagcccgt gaaacccttc | 300 |
| cttttctacc gtgccaagac tggtaggacc tccaccctg agtctgtggc cttccccggac | 360 |
| tggttcattg cctcctccaa gagagaccag cccatcattc tgacttcaga acttgggaag | 420 |
| tcatacaaca ctgcctttga attaaatata aatgacagat ctggcagttc tgactacaag | 480 |
| gacgacgacg acaagggcag ttctcaccat caccatcacc actag | 525 |

<210> SEQ ID NO 78

```
<211> LENGTH: 819
<212> TYPE: DNA
<213> ORGANISM: Homo sapiens
<220> FEATURE:
<221> NAME/KEY: misc_feature
<222> LOCATION: (1)..(357)
<223> OTHER INFORMATION: SUMO tag

<400> SEQUENCE: 78
atgggcagca gccatcatca tcatcatcac ggcagcggcc tggtgccgcg cggcagcgct      60
agcatgtcgg actcagaagt caatcaagaa gctaagccag aggtcaagcc agaagtcaag     120
cctgagactc acatcaattt aaaggtgtcc gatggatctt cagagatctt cttcaagatc     180
aaaaagacca ctcctttaag aaggctgatg gaagcgttcg ctaaaagaca gggtaaggaa     240
atggactcct taagattctt gtacgacggt attagaattc aagctgatca gaccccctgaa    300 gatttggaca tggaggataa cgatattatt gaggctcaca gagaacagat tggtggtaaa     360
attgacacac ctcagcgggg gagcattcag gatatcaatc atcgggtgtg ggttcttcag     420
gaccagacgc tcatagcagt cccgaggaag gaccgtatgt ctccagtcac tattgcctta     480
atctcatgcc gacatgtgga gacccttgag aaagacagag ggaaccccat ctacctgggc     540
ctgaatggac tcaatctctg cctgatgtgt gctaaagtcg gggaccagcc cacactgcag     600
ctgaaggaaa aggatataat ggatttgtac aaccaacccg agcctgtgaa gtcctttctc     660
ttctaccaca gccagagtgg caggaactcc accttcgagt ctgtggcttt ccctggctgg     720
ttcatcgctg tcagctctga aggaggctgt cctctcatcc ttacccaaga actggggaaa     780
gccaacacta ctgactttgg gttaactatg ctgttttaa                            819
```

IL-1F5 POLYPEPTIDES

This application claims the benefit of U.S. Non-provisional patent application Ser. No. 11/900,235, filed Sep. 10, 2007, which claims the benefit of U.S. Provisional Application No. 60/843,311, filed Sep. 8, 2006, both of which are hereby incorporated by reference in their entirety.

The present application is being filed along with a Sequence Listing in electronic format. The Sequence Listing is provided as a file entitled A-1129.txt, created Oct. 12, 2011, which is 84 KB in size. The information in the electronic format of the Sequence Listing is incorporated herein by reference in its entirety.

Throughout this application various publications are referenced within parentheses or brackets. The disclosures of these publications in their entireties are hereby incorporated by reference in this application in order to more fully describe the state of the art to which this invention pertains.

FIELD OF THE INVENTION

This application provides nucleic acids, polypeptides, compositions, assays, and methods relating to variants of IL-1 Family members that signal through IL-1Rrp2.

BACKGROUND OF THE INVENTION

The IL-1 family includes several cytokines whose primary function is to mediate immune and inflammatory responses. The earliest members discovered were IL-1 alpha, IL-1 beta, IL-1 receptor antagonist (IL-1ra), and IL-18 (previously known as IGIF and sometimes IL-1 gamma). Following the discovery of additional proteins with homology to these IL-1 family members, a nomenclature system was adopted in which IL-1 alpha is referred to as IL-1F1, IL-1 beta as IL-1F2, IL-1ra as IL-1F3 and IL-18 as IL-1F4. Seven additional cytokines have been classified as IL-1 family members based on amino acid sequence similarity, identity of gene structure, and predicted or known three-dimensional structure (Sims, J. E. et al., *Trends Immunol* 22:537, 2001; Dunn, E., et al., *Trends Immunol* 22:533, 2001; Dunn, E. F., et al., *Biochemistry* 42:10938, 2003; Schmitz et al. *Immunity* 23:479-490, 2005).

IL-1 alpha, IL-1 beta and IL-1ra (IL-1F1-3, respectively) bind to receptors that are members of the immunoglobulin superfamily, the 80 kDa type I receptor (IL-1RI) and a 68 kDa type II receptor (IL-1RII), as well as a soluble proteolytic fragment of IL-1RII (sIL-1RII). Binding of IL-1 (alpha or beta) to the type I IL-1 receptor (IL-1R) results in recruitment of the IL-1R homolog, IL-1R accessory protein (IL-1RAcP or AcP), which does not directly bind the ligands but is required for signal transduction (Sims et al. *Trends Immunol* 22; 537, 2001); binding of IL-1ra does not. Signaling by IL-18 is very similar, although IL-18 utilizes a different receptor complex (Born, T. L., et al., *J Biol Chem* 273:29445, 1998). IL-1F5, F6, F8 and F9 make use of the IL-1R-related protein 2 (IL-1Rrp2), with F6, F8 and F9 agonizing this receptor pathway, and IL-1F5 antagonizing it (Debets, R., et al., *J Immunol* 167:1440, 2001; Towne et al. 2004 *J Biol Chem* 279(14): 13677)

Several members of the IL-1 family (IL-1 alpha, IL-1 beta, IL-18, IL-1F7 and IL-33) are synthesized as precursor molecules that are proteolytically cleaved, by caspase-1 in the case of IL-1 beta and IL-18, and by an unidentified protease or proteases for IL-33, IL-1 alpha and IL-1F7. IL-1ra is activated by signal peptidase cleavage of a short peptide from the n-terminus. However, little is known about what, if any, processing occurs with the remaining family members.

BRIEF DESCRIPTION OF THE DRAWINGS

FIG. 1 provides an alignment of the N-terminal portions of wild type IL-1F5, F6, F8 and F9. There is a (Met or Ile)-Xaa-Asp sequence present in each of F5, F6, F8 and F9, marked by underlining of the Met/Ile and the Asp residues. There is a similar "aliphatic amino acid-X-Aspartate or other polar amino acid" motif present in all IL-1 family members, and this can be used to align IL-1 family sequences. The consensus motif is indicated by @XD where @ may be an aliphatic amino acid such as Met or Ile and X is any one amino acid D is Asp. In FIG. 1, the sequences are lined up using the Met/Ile-Xaa-Asp motif (Met 11 in F5, Ile15 in F6, Ile14 in F8, and Ile27 in F9 respectively), so that the natural N-termini (with initiating methionines) lie at different distances upstream of the aliphatic amino acid, @, of the motif.

FIG. 2 is the full length wild type amino acid sequences of IL-1F5, IL-1F6, IL-1F8 and IL-1F9.

SUMMARY OF THE INVENTION

In one aspect, the present invention provides an isolated IL-1F5 polypeptide that antagonizes signal transduction/activation through IL-1Rrp2, where the IL-1F5 polypeptide contains the sequence Met-Lys-Asp, which matches the consensus @XD depicted in FIG. 1, and wherein the polypeptide comprises nine amino acids on the N-terminal side of the above-referenced methionine. In one embodiment the IL-1F5 polypeptide is a human IL-1F5 polypeptide. In one embodiment, the IL-1F5 polypeptide of the invention comprises an amino acid sequence having a methionine at position ten of the amino acid sequence, position ten being relative to the N-terminal amino acid at position one of the amino acid sequence. In one embodiment, the IL-1F5 polypeptide of the invention comprises an amino acid sequence having a methionine at position ten of the amino acid sequence, position ten being relative to the N-terminal amino acid at position one of the amino acid sequence and an amino acid selected from the group consisting of valine and methionine at the N-terminal amino acid at position one. In one embodiment, the IL-1F5 polypeptide of the invention comprises an amino acid sequence having a methionine at position ten of the amino acid sequence, position ten being relative to the N-terminal amino acid at position one of the amino acid sequence and a leucine at position two of its amino acid sequence. In a particular embodiment the IL-1F5 polypeptide of the invention, comprises an amino acid sequence having a methionine at position ten of the amino acid sequence, position ten being relative to the N-terminal amino acid at position one of the amino acid sequence and an amino acid selected from the group consisting of valine and methionine at the N-terminal amino acid at position one and a leucine at position two.

In particular embodiments, the IL-1F5 polypeptide of the invention comprises at least 90%, at least 95%, at least 98% or at least 99% identity to SEQ ID NO 1 and a methionine at position ten of the amino acid sequence of the IL-1F5 polypeptide of the invention, position ten being relative to the N-terminal amino acid a position one. In some embodiments, the isolated IL-1F5 polypeptide of the invention antagonizes signal transduction/activation through IL-1Rrp2 more than the IL-1F5 polypeptide having the amino acid sequence of SEQ ID NO 1. In some embodiments, the isolated IL-1F5 polypeptide of the invention antagonizes signal transduction/activation through IL-1Rrp2 more than about 5 fold, 10 fold, 100 fold, 1,000 fold the level of antagonization of signal transduction/activation of the IL-1F5 polypeptide having the amino acid sequence of SEQ ID NO 1. The level of signal transduction/activation antagonization is measured according to the method described in Example 2A.

In a particular embodiment, the isolated IL-1F5 polypeptide of the invention has a methionine at position ten of its amino acid sequence relative to the N-terminal amino acid at position one and comprises an amino acid sequence selected from the group consisting of:

```
                                                        (SEQ ID NO 6)
VLSGALCFRMKDSALKVLYLHNNQLLAGGLHAGKVIKGEEISVVPNRWLDASLSPVILG

VQGGSQCLSCGVGQEPTLTLEPVNIMELYLGAKESKSFTFYRRDMGLTSSFESAAYPGW

FLCTVPEADQPVRLTQLPENGGWNAPITDFYFQQCD,
                                                        (SEQ ID NO 7)
MLSGALCFRMKDSALKVLYLHNNQLLAGGLHAGKVIKGEEISVVPNRWLDASLSPVILG

VQGGSQCLSCGVGQEPTLTLEPVNIMELYLGAKESKSFTFYRRDMGLTSSFESAAYPGW

FLCTVPEADQPVRLTQLPENGGWNAPITDFYFQQCDDYKDDDDKHHH,
                                                        (SEQ ID NO 8)
MLSGALCFRMKDSALKVLYLHNNQLLAGGLHAGKVIKGEEISVVPNRWLDASLSPVILG

VQGGSQCLSCGVGQEPTLTLEPVNIMELYLGAKESKSFTFYRRDMGLTSSFESAAYPGW

FLCTVPEADQPVRLTQLPENGGWNAPITDFYFQQCD
and
                                                        (SEQ ID NO 9)
MLSGALCFRMKDSALKVLYLHNNQLLAGGLHAGKVIKGEEISVVPNRWLDASLSPVILG

VQGGSQCLSCGVGQEPTLTLEPVNIMELYLGAKESKSFTFYRRDMGLTSSFESAAYPGW

FLCTVPEADQPVRLTQLPENGGWNAPITDFYFQQCDDYKDDDDKHHH.
```

In another embodiment, a nucleic acid sequence encoding the isolated IL-1F5 polypeptide of the invention is provided. In another aspect of the invention, a recombinant vector that directs expression of a nucleic acid encoding an isolated IL-1F5 polypeptide of the invention is provided. In a particular embodiment, the vector of the invention comprises a nucleic acid sequence selected from the group consisting of:

In another aspect, a host cell transfected or transduced with a recombinant vector that directs expression of a nucleic acid encoding an IL-1F5 polypeptide of the invention is provided. In another aspect, a method of producing an isolated IL-1F5 polypeptide of the invention comprising culturing the host cell transfected or transduced with a recombinant vector that directs expression of an IL-1F5 polypeptide of the invention,

```
                                                        (SEQ ID NO 69)
GTCCTGAGTGGGGCGCTGTGCTTCCGAATGAAGGACTCGGCATTGAAGGTGCTTTAT

CTGCATAATAACCAGCTTCTAGCTGGAGGGCTGCATGCAGGGAAGGTCATTAAAGGT

GAAGAGATCAGCGTGGTCCCCAATCGGTGGCTGGATGCCAGCCTGTCCCCCGTCATC

CTGGGTGTCCAGGGTGGAAGCCAGTGCCTGTCATGTGGGGTGGGGCAGGAGCCGAC

TCTAACACTAGAGCCAGTGAACATCATGGAGCTCTATCTTGGTGCCAAGGAATCCAA

GAGCTTCACCTTCTACCGGCGGGACATGGGGCTCACCTCCAGCTTCGAGTCGGCTGC

CTACCCGGGCTGGTTCCTGTGCACGGTGCCTGAAGCCGATCAGCCTGTCAGACTCAC

CCAGCTTCCCGAGAATGGTGGCTGGAATGCCCCCATCACAGACTTCTACTTCCAGCA

GTGTGACTAA
and
                                                        (SEQ ID NO 70)
ATGCTGAGTGGGGCGCTGTGCTTCCGAATGAAGGACTCGGCATTGAAGGTGCTTTAT

CTGCATAATAACCAGCTTCTAGCTGGAGGGCTGCATGCAGGGAAGGTCATTAAAGGT

GAAGAGATCAGCGTGGTCCCCAATCGGTGGCTGGATGCCAGCCTGTCCCCCGTCATC

CTGGGTGTCCAGGGTGGAAGCCAGTGCCTGTCATGTGGGGTGGGGCAGGAGCCGAC

TCTAACACTAGAGCCAGTGAACATCATGGAGCTCTATCTTGGTGCCAAGGAATCCAA

GAGCTTCACCTTCTACCGGCGGGACATGGGGCTCACCTCCAGCTTCGAGTCGGCTGC

CTACCCGGGCTGGTTCCTGTGCACGGTGCCTGAAGCCGATCAGCCTGTCAGACTCAC

CCAGCTTCCCGAGAATGGTGGCTGGAATGCCCCCATCACAGACTTCTACTTCCAGCA

GTGTGACAGATCTGGCAGTTCTGACTACAAGGACGACGACGACAAGGGCAGTTCTC

ACCATCACCATCACCACTAG.
``` under conditions promoting expression and isolating the expressed IL-1F5 polypeptide is provided.

An antibody or a fragment thereof that specifically binds an IL-1F5 polypeptide and prevents IL-1F5 antagonism of signal transduction through IL-1Rrp2 is provided. In particular embodiments, an antibody that binds an IL-1F5 polypeptide comprising an amino acid sequence selected from the group consisting of: SEQ ID NO 6, SEQ ID NO 7, SEQ ID NO 8, and SEQ ID NO 9 is provided. In some embodiments, the IL-1F5 antibody of the invention, is a monoclonal antibody, particularly a chimeric antibody, a humanized antibody or a fully human antibody. The invention provides a composition, particularly a pharmaceutical composition, comprising the IL-1F5 antibody of the invention and a physiologically acceptable diluent, excipient or carrier. A method of stimulating the immune system of an immunosuppressed subject, comprising administering the anti-IL-1F5 antibody of the invention to an immunosuppressed subject in an amount sufficient to stimulate the patient's immune system is provided.

In another aspect, a composition, particularly a pharmaceutical composition, comprising an IL-1F5 polypeptide of the invention and a physiologically acceptable diluent, excipient or carrier is provided. In another embodiment, the invention provides a method of treating an inflammatory or autoimmune condition in a subject wherein the inflammatory or autoimmune condition is mediated by IL-1Rrp2, comprising administering to the subjecting an amount of the IL-1F5 polypeptide of the invention sufficient to reduce at least one symptom of the inflammatory or autoimmune condition in the subject. In one embodiment, the condition to be treated is an inflammatory condition of the skin, lungs or airways mediated by IL-1Rrp2. In a particular embodiment, the condition to be treated is selected from the group consisting of psoriasis, seborrheic dermatitis, atopic dermatitis, including chronic atopic dermatitis, allergic contact dermatitis, lichen simplex chronicus, pityriasis rubra pilaris, nummular dermatitis, asthma, allergic rhinitis, gastro-esophageal reflux disease, arthritic conditions including, rheumatoid arthritis, psoriatic arthritis, and osteoarthritis. In particular embodiments of the above methods, the subject is human.

In one aspect, the present invention provides an isolated IL-1F6 polypeptide that agonizes signal transduction/activation through IL-1Rrp2, where the IL-1F6 polypeptide contains the sequence Ile-Gln-Asp, which matches the consensus @XD described in FIG. 1, and wherein the polypeptide comprises nine amino acids on the N-terminal side of the above-referenced isoleucine. In one embodiment the IL-1F6 polypeptide is a human IL-1F6 polypeptide. In one embodiment, the IL-1F6 polypeptide of the invention comprises an amino acid sequence having an isoleucine at position ten of its amino acid sequence, position ten being relative to the N-terminal amino acid at position one. In one embodiment, the IL-1F6 polypeptide of the invention comprises an amino acid sequence having an isoleucine at position ten of its amino acid sequence, position ten being relative to the N-terminal amino acid at position one and an amino acid selected from the group consisting of lysine and methionine at the N-terminal amino acid at position one. In one embodiment, the IL-1F6 polypeptide of the invention comprises an amino acid sequence having an isoleucine at position ten of its amino acid sequence, position ten being relative to the N-terminal amino acid at position one, and an isoleucine at position two of its amino acid sequence. In a particular embodiment the IL-1F6 polypeptide of the invention, comprises an amino acid sequence having a isoleucine at position ten of the amino acid sequence, position ten being relative to the N-terminal amino acid at position one, and an amino acid selected from the group consisting of lysine and methionine at the N-terminal amino acid at position and an isoleucine at position two.

In particular embodiments, the isolated IL-1F6 polypeptide comprises at least 90%, at least 95%, at least 97% or at least 98% identity to SEQ ID NO 2 or to SEQ ID NO 2 except that there is an arginine at amino acid position 12 rather than a glutamine and an isoleucine at position ten, position ten being relative to the N-terminal amino acid at position one of the IL-1F6 amino acid sequence of the invention. In some embodiments, the isolated IL-1F6 polypeptide of the invention agonizes signal transduction/activation through IL-1Rrp2 more than the IL-1F6 polypeptide having the N-terminal amino acid sequence of SEQ ID NO 2. In some embodiments, the isolated IL-1F6 polypeptide of the invention agonizes signal transduction/activation through IL-1Rrp2 more than about 5 fold, 10 fold, 100 fold, 200 fold, 1,000 fold, 2,000 fold, 10,000 fold, 50,000 fold the level of agonization of signal transduction/activation of the IL-1F6 polypeptide having the amino acid sequence of SEQ ID NO 2. The level of signal transduction/activation agonization is measured according to the method described in Example 2B.

In another aspect, the invention provides an isolated IL-1F6 polypeptide that agonizes signal transduction/activation through IL-1Rrp2, wherein the IL-1F6 polypeptide comprises an amino acid sequence having a isoleucine at position ten of its amino acid sequence, position ten being relative to the N-terminal amino acid at position one and an amino acid sequence selected from the group consisting of:

```
                                               (SEQ ID NO 10)
KIDTPQQGSIQDINHRVWVLQDQTLIAVPRKDRMSPVTIALISCRHVETLEKDRGNPIYLG

LNGLNLCLMCAKVGDQPTLQLKEKDIMDLYNQPEPVKSFLFYHSQSGRNSTFESVAFPG

WFIAVSSEGGCPLILTQELGKANTTDFGLTMLF, (SEQ ID NO 11)
KIDTPQQGSIQDINHRVWVLQDQTLIAVPRKDRMSPVTIALISCRHVETLEKDRGNPIYLG

LNGLNLCLMCAKVGDQPTLQLKEKDIMDLYNQPEPVKSFLFYHSQSGRNSTFESVAFPG

WFIAVSSEGGCPLILTQELGKANTTDFGLTMLFDYKDDDDKHHH, (SEQ ID NO 12)
MIDTPQQGSIQDINHRVWVLQDQTLIAVPRKDRMSPVTIALISCRHVETLEKDRGNPIYL

GLNGLNLCLMCAKVGDQPTLQLKEKDIMDLYNQPEPVKSFLFYHSQSGRNSTFESVAFP

GWFIAVSSEGGCPLILTQELGKANTTDFGLTMLF,
```

-continued (SEQ ID NO 13)
MIDTPQQGSIQDINHRVWVLQDQTLIAVPRKDRMSPVTIALISCRHVETLEKDRGNPIYL

GLNGLNLCLMCAKVGDQPTLQLKEKDIMDLYNQPEPVKSFLFYHSQSGRNSTFESVAFP

GWFIAVSSEGGCPLILTQELGKANTTDFGLTMLFDYKDDDDKHHH, (SEQ ID NO 65)
KIDTPQRGSIQDINHRVWVLQDQTLIAVPRKDRMSPVTIALISCRHVETLEKDRGNPIYLG

LNGLNLCLMCAKVGDQPTLQLKEKDIMDLYNQPEPVKSFLFYHSQSGRNSTFESVAFPG

WFIAVSSEGGCPLILTQELGKANTTDFGLTMLF, (SEQ ID NO 66)
KIDTPQRGSIQDINHRVWVLQDQTLIAVPRKDRMSPVTIALISCRHVETLEKDRGNPIYLG

LNGLNLCLMCAKVGDQPTLQLKEKDIMDLYNQPEPVKSFLFYHSQSGRNSTFESVAFPG

WFIAVSSEGGCPLILTQELGKANTTDFGLTMLFDYKDDDDKHHH, (SEQ ID NO 67)
MIDTPQRGSIQDINHRVWVLQDQTLIAVPRKDRMSPVTIALISCRHVETLEKDRGNPIYLG

LNGLNLCLMCAKVGDQPTLQLKEKDIMDLYNQPEPVKSFLFYHSQSGRNSTFESVAFPG

WFIAVSSEGGCPLILTQELGKANTTDFGLTMLF
and (SEQ ID NO 68)
MIDTPQRGSIQDINHRVWVLQDQTLIAVPRKDRMSPVTIALISCRHVETLEKDRGNPIYLG

LNGLNLCLMCAKVGDQPTLQLKEKDIMDLYNQPEPVKSFLFYHSQSGRNSTFESVAFPG

WFIAVSSEGGCPLILTQELGKANTTDFGLTMLFDYKDDDDKHHH.

In another embodiment, a nucleic acid sequence encoding the isolated IL-1F6 polypeptide of the invention is provided. In another aspect of the invention, a recombinant vector that directs expression of a nucleic acid encoding an isolated IL-1F6 polypeptide of the invention is provided. In a particular embodiment, the vector of the invention comprises a nucleic acid sequence selected from the group consisting of:

(SEQ ID NO 71)
AAAATTGACACACCTCAGCGGGGAGCATTCAGGATATCAATCATCGGGTGTGGGTT

CTTCAGGACCAGACGCTCATAGCAGTCCCGAGGAAGGACCGTATGTCTCCAGTCACT

ATTGCCTTAATCTCATGCCGACATGTGGAGACCCTTGAGAAAGACAGAGGGAACCCC

ATCTACCTGGGCCTGAATGGACTCAATCTCTGCCTGATGTGTGCTAAAGTCGGGGAC

CAGCCCACACTGCAGCTGAAGGAAAAGGATATAATGGATTTGTACAACCAACCCGA

GCCTGTGAAGTCCTTTCTCTTCTACCACAGCCAGAGTGGCAGGAACTCCACCTTCGA

GTCTGTGGCTTTCCCTGGCTGGTTCATCGCTGTCAGCTCTGAAGGAGGCTGTCCTCTC

ATCCTTACCCAAGAACTGGGGAAAGCCAACACTACTGACTTTGGGTTAACTATGCTG

TTTTAA
and (SEQ ID NO 72)
ATGATTGACACACCTCAGCGGGGAGCATTCAGGATATCAATCATCGGGTGTGGGTT

CTTCAGGACCAGACGCTCATAGCAGTCCCGAGGAAGGACCGTATGTCTCCAGTCACT

ATTGCCTTAATCTCATGCCGACATGTGGAGACCCTTGAGAAAGACAGAGGGAACCCC

ATCTACCTGGGCCTGAATGGACTCAATCTCTGCCTGATGTGTGCTAAAGTCGGGGAC

CAGCCCACACTGCAGCTGAAGGAAAAGGATATAATGGATTTGTACAACCAACCCGA

GCCTGTGAAGTCCTTTCTCTTCTACCACAGCCAGAGTGGCAGGAACTCCACCTTCGA

GTCTGTGGCTTTCCCTGGCTGGTTCATCGCTGTCAGCTCTGAAGGAGGCTGTCCTCTC

ATCCTTACCCAAGAACTGGGGAAAGCCAACACTACTGACTTTGGGTTAACTATGCTG

```
-continued
TTTAGATCTGGCAGTTCTGACTACAAGGACGACGACGACAAGGGCAGTTCTCACCAT

CACCATCACCACTAG.
```

In another aspect, a host cell transfected or transduced with a recombinant vector that directs expression of a nucleic acid encoding an IL-1F6 polypeptide of the invention is provided. In anther aspect, a method of producing an isolated IL-1F6 polypeptide of the invention comprising culturing the host cell transfected or transduced with a recombinant vector that directs expression of an IL-1F6 polypeptide of the invention, under conditions promoting expression and isolating the expressed IL-1F6 polypeptide is provided.

In another aspect, a composition, particularly a pharmaceutical composition, comprising an IL-1F6 polypeptide of the invention and a physiologically acceptable diluent, excipient or carrier is provided. A method of stimulating the immune system of an immunosuppresed subject, comprising administering the IL-1F6 polypeptide according of the invention to an immunosuppressed subject in an amount sufficient to stimulate the subject's immune system is provided.

An antibody that specifically binds IL-1F6, where IL-1F6 may be a full length IL-1F6 or a truncant of full length IL-1F6, and prevents proteolytic cleavage thereof, particularly proteolytic cleavage to a more active form where activity is relative to that of the full length IL-1F6, is provided. An antibody that binds an IL-1F6 polypeptide of the invention, and prevents signal transduction/activation through IL-1FRrp2 is also provided. In some embodiments, an antibody binding an IL-1F6 polypeptide selected from the group consisting of: SEQ ID NO 10, SEQ ID NO 11, SEQ ID NO 12, SEQ ID NO 13, SEQ ID NO 65, SEQ ID NO 66, SEQ ID NO 67 and SEQ ID NO 68 is provided. In some embodiments, the IL-1F6 antibody of the invention, is a monoclonal antibody, particularly a chimeric antibody, a humanized antibody or a fully human antibody. The invention provides a composition, particularly a pharmaceutical composition, comprising the IL-1F6 antibody of the invention and a physiologically acceptable diluent, excipient or carrier.

The invention also provides, a method of treating an inflammatory or autoimmune condition mediated by IL-1Rrp2, comprising administering the IL-1F6 antibody of the invention to a subject in an amount sufficient to ameliorate at least one symptom mediated by IL-1Rrp2 of the condition. In one embodiment, the condition to be treated is an inflammatory condition of the skin, lungs or airways mediated by IL-1Rrp2. In a particular embodiment, the condition to be treated is selected from the group consisting of psoriasis, seborrheic dermatitis, atopic dermatitis, including chronic atopic dermatitis, allergic contact dermatitis, lichen simplex chronicus, pityriasis rubra pilaris, nummular dermatitis, asthma, allergic rhinitis, gastro-esophageal reflux disease, arthritic conditions including, rheumatoid arthritis, psoriatic arthritis, and osteoarthritis. In particular embodiments, the subject to be treated in the above methods is a human.

In one aspect, the present invention provides an isolated IL-1F8 polypeptide that agonizes signal transduction/activation through IL-1Rrp2, where the IL-1F8 polypeptide contains the sequence Ile-Arg-Asp, which matches the consensus @XD described in FIG. 1, and wherein the polypeptide comprises nine amino acids on the N-terminal side of the above-referenced isoleucine. In one embodiment the IL-1F8 polypeptide is a human IL-1F8 polypeptide. In one embodiment, the IL-1F8 polypeptide of the invention comprises an amino acid sequence having an isoleucine at position ten of its amino acid sequence, position ten being relative to the N-terminal amino acid at position one. In one embodiment, the IL-1F8 polypeptide of the invention comprises an amino acid sequence having an isoleucine at position ten of its amino acid sequence, position ten being relative to the N-terminal amino acid at position one and an amino acid selected from the group consisting of arginine and methionine at the N-terminal amino acid at position one. In one embodiment, the IL-1F8 polypeptide of the invention comprises an amino acid sequence having an isoleucine at position ten of its amino acid sequence, position ten being relative to the N-terminal amino acid at position one, and a glutamic acid at position two of its amino acid sequence. In a particular embodiment the IL-1F8 polypeptide of the invention, comprises an amino acid sequence having a isoleucine at position ten of the amino acid sequence, position ten being relative to the N-terminal amino acid at position one, and an amino acid selected from the group consisting of arginine and methionine at the N-terminal amino acid at position and an glutamic acid at position two.

In particular embodiments, the isolated IL-1F8 polypeptide comprises at least 90%, at least 95%, or at least 98% identity to SEQ ID NO 3 and an isoleucine at position ten, position ten being relative to the N-terminal amino acid at position one of the IL-1F8 amino acid sequence of the invention. In some embodiments, the isolated IL-1F8 polypeptide of the invention agonizes signal transduction/activation through IL-1Rrp2 more than the IL-1F8 polypeptide having the amino acid sequence of SEQ ID NO 3. In some embodiments, the isolated IL-1F8 polypeptide of the invention agonizes signal transduction/activation through IL-1Rrp2 more than about 5 fold, 10 fold, 100 fold, 200 fold, 1,000 fold, 3,000 fold, 5,000 fold, 10,000 fold, 50,000 fold the level of agonization of signal transduction/activation of the IL-1F8 polypeptide having the amino acid sequence of SEQ ID NO 3. The level of signal transduction/activation agonization is measured according to the method described in Example 2B.

In another aspect, the invention provides an isolated IL-1F8 polypeptide that agonizes signal transduction/activation through IL-1Rrp2, wherein the IL-1F8 polypeptide comprises an amino acid sequence having a isoleucine at position ten of its amino acid sequence, position ten being relative to the N-terminal amino acid at position one and an amino acid sequence selected from the group consisting of:

```
                                                        (SEQ ID NO 14)
REAAPKSYAIRDSRQMVWVLSGNSLIAAPLSRSIKPVTLHLIACRDTEFSDKEKGNMVYL

GIKGKDLCLFCAEIQGKPTLQLKEKNIMDLYVEKKAQKPFLFFHNKEGSTSVFQSVSYPG

WFIATSTTSGQPIFLTKERGITNNTNFYLDSVE,
```

-continued (SEQ ID NO 15)
REAAPKSYAIRDSRQMVWVLSGNSLIAAPLSRSIKPVTLHLIACRDTEFSDKEKGNMVYL

GIKGKDLCLFCAEIQGKPTLQLKEKNIMDLYVEKKAQKPFLFFHNKEGSTSVFQSVSYPG

WFIATSTTSGQPIFLTKERGITNNTNFYLDSVEDYKDDDDKHHH;

(SEQ ID NO 16)
MEAAPKSYAIRDSRQMVWVLSGNSLIAAPLSRSIKPVTLHLIACRDTEFSDKEKGNMVY

LGIKGKDLCLFCAEIQGKPTLQLKEKNIMDLYVEKKAQKPFLFFHNKEGSTSVFQSVSYP

GWFIATSTTSGQPIFLTKERGITNNTNFYLDSVE
and (SEQ ID NO 17)
MEAAPKSYAIRDSRQMVWVLSGNSLIAAPLSRSIKPVTLHLIACRDTEFSDKEKGNMVY

LGIKGKDLCLFCAEIQGKPTLQLKEKNIMDLYVEKKAQKPFLFFHNKEGSTSVFQSVSYP

GWFIATSTTSGQPIFLTKERGITNNTNFYLDSVEDYKDDDDKHHH.

In another embodiment, a nucleic acid sequence encoding the isolated IL-1F8 polypeptide of the invention is provided. In another aspect of the invention, a recombinant vector that directs expression of a nucleic acid encoding an isolated IL-1F8 polypeptide of the invention is provided. In a particular embodiment, the vector of the invention comprises a nucleic acid sequence selected from the group consisting of:

(SEQ ID NO 73)
CGCGAGGCAGCACCCAAATCCTATGCTATTCGTGATTCTCGACAGATGGTGTGGGTC

CTGAGTGGAAATTCTTTAATAGCAGCTCCTCTTAGCCGCAGCATTAAGCCTGTCACTC

TTCATTTAATAGCCTGTAGAGACACAGAATTCAGTGACAAGGAAAAGGGTAATATG

GTTTACCTGGGAATCAAGGGAAAAGATCTCTGTCTCTTCTGTGCAGAAATTCAGGGC

AAGCCTACTTTGCAGCTTAAGGAAAAAAATATCATGGACCTGTATGTGGAGAAGAA

AGCACAGAAGCCCTTTCTCTTTTTCCACAATAAAGAAGGCTCCACTTCTGTCTTTCAG

TCAGTCTCTTACCCTGGCTGGTTCATAGCCACCTCCACCACATCAGGACAGCCCATCT

TTCTCACCAAGGAGAGAGGCATAACTAATAACACTAACTTCTACTTAGATTCTGTGG

AATAA
and (SEQ ID NO 74)
ATGGAGGCAGCACCCAAATCCTATGCTATTCGTGATTCTCGACAGATGGTGTGGGTC

CTGAGTGGAAATTCTTTAATAGCAGCTCCTCTTAGCCGCAGCATTAAGCCTGTCACTC

TTCATTTAATAGCCTGTAGAGACACAGAATTCAGTGACAAGGAAAAGGGTAATATG

GTTTACCTGGGAATCAAGGGAAAAGATCTCTGTCTCTTCTGTGCAGAAATTCAGGGC

AAGCCTACTTTGCAGCTTAAGGAAAAAAATATCATGGACCTGTATGTGGAGAAGAA

AGCACAGAAGCCCTTTCTCTTTTTCCACAATAAAGAAGGCTCCACTTCTGTCTTTCAG

TCAGTCTCTTACCCTGGCTGGTTCATAGCCACCTCCACCACATCAGGACAGCCCATCT

TTCTCACCAAGGAGAGAGGCATAACTAATAACACTAACTTCTACTTAGATTCTGTGG

AAGGATCTGGCAGTTCTGACTACAAGGACGACGACGACAAGGGCAGTTCTCACCAT

CACCATCACCACTAG.

polypeptide of the invention comprising culturing the host cell transfected or transduced with a recombinant vector that directs expression of an IL-1F8 polypeptide of the invention, under conditions promoting expression and isolating the expressed IL-1F8 polypeptide is provided.

In another aspect, a composition, particularly a pharmaceutical composition, comprising an IL-1F8 polypeptide of the invention and a physiologically acceptable diluent, excipient or carrier is provided. A method of stimulating the immune system of an immunosuppressed subject, comprising administering the IL-1F8 polypeptide according of the invention to an immunosuppressed subject in an amount sufficient to In another aspect, a host cell transfected or transduced with a recombinant vector that directs expression of a nucleic acid encoding an IL-1F8 polypeptide of the invention is provided. In another aspect, a method of producing an isolated IL-1F8 stimulate the subject's immune system is provided. In particular embodiments of the above methods, the subject is a human.

An antibody that specifically binds IL-1F8, where IL-1F8 may be a full length IL-1F8 or a truncant of full length IL-1F8, and prevents proteolytic cleavage thereof, particularly proteolytic cleavage to a more active form where activity is relative to that of the full length IL-1F8, is provided. An antibody that binds an IL-1F8 polypeptide of the invention, and prevents signal transduction/activation through IL-1FRrp2 is also provided. In some embodiments, an antibody binding an IL-1F8 polypeptide selected from the group consisting of: SEQ ID NO 14, SEQ ID NO 15, SEQ ID NO 16 and SEQ ID NO 17, is provided. In some embodiments, the IL-1F8 antibody of the invention, is a monoclonal antibody, particularly a chimeric antibody, a humanized antibody or a fully human antibody. The invention provides a composition, particularly a pharmaceutical composition, comprising the IL-1F8 antibody of the invention and a physiologically acceptable diluent, excipient or carrier.

The invention also provides, a method of treating an inflammatory or autoimmune condition mediated by IL-1Rrp2, comprising administering the IL-1F8 antibody of the invention to a subject in an amount sufficient to ameliorate at least one symptom mediated by IL-1Rrp2 of the condition. In one embodiment, the condition to be treated is an inflammatory condition of the skin, lungs or airways mediated by IL-1Rrp2. In a particular embodiment, the condition to be treated is selected from the group consisting of psoriasis, seborrheic dermatitis, atopic dermatitis, including chronic atopic dermatitis, allergic contact dermatitis, lichen simplex chronicus, pityriasis rubra pilaris, nummular dermatitis, asthma, allergic rhinitis, gastro-esophageal reflux disease, arthritic conditions including, rheumatoid arthritis, psoriatic arthritis, and osteoarthritis.

In one aspect, the present invention provides an isolated IL-1F9 polypeptide that agonizes signal transduction/activation through IL-1Rrp2, where the IL-1F9 polypeptide comprises the consensus sequence @XD described in FIG. 1, where the IL-1F9 polypeptide contains the sequence Ile-Asn-Asp, which matches the consensus @XD, and wherein the polypeptide comprises nine amino acids on the N-terminal side of the above-referenced isoleucine. In one embodiment the IL-1F9 polypeptide is a human IL-1F9 polypeptide. In one embodiment, the IL-1F9 polypeptide of the invention comprises an amino acid sequence having an isoleucine at position ten of its amino acid sequence, position ten being relative to the N-terminal amino acid at position one. In one embodiment, the IL-1F9 polypeptide of the invention comprises an amino acid sequence having an isoleucine at position ten of its amino acid sequence, position ten being relative to the N-terminal amino acid at position one and an amino acid selected from the group consisting of serine and methionine at the N-terminal amino acid at position one. In one embodiment, the IL-1F9 polypeptide of the invention comprises an amino acid sequence having an isoleucine at position ten of its amino acid sequence, position ten being relative to the N-terminal amino acid at position one, and a methionine at position two of its amino acid sequence. In a particular embodiment the IL-1F9 polypeptide of the invention, comprises an amino acid sequence having a isoleucine at position ten of the amino acid sequence, position ten being relative to the N-terminal amino acid at position one, and an amino acid selected from the group consisting of serine and methionine at the N-terminal amino acid at position and an glutamic acid at position two.

In particular embodiments, the isolated IL-1F9 polypeptide comprises at least 85% or at least 89% identity to SEQ ID NO 4 and an isoleucine at position ten, position ten being relative to the N-terminal amino acid at position one of the IL-1F9 amino acid sequence of the invention. In some embodiments, the isolated IL-1F9 polypeptide of the invention agonizes signal transduction/activation through IL-1Rrp2 more than the IL-1F9 polypeptide having the amino acid sequence of SEQ ID NO 4. In some embodiments, the isolated IL-1F9 polypeptide of the invention agonizes signal transduction/activation through IL-1Rrp2 more than about 5 fold, 10 fold, 50 fold, 100 fold, 600 fold, 1,000 fold, 3,000 fold, 5,000 fold, 10,000 fold or 50,000 fold the level of agonization of signal transduction/activation of the IL-1F9 polypeptide having the amino acid sequence of SEQ ID NO 4. The level of signal transduction/activation agonization is measured according to the method described in Example 2B.

In another aspect, the invention provides an isolated IL-1F9 polypeptide that agonizes signal transduction/activation through IL-1Rrp2, wherein the IL-1F9 polypeptide comprises an amino acid sequence having a isoleucine at position ten of its amino acid sequence, position ten being relative to the N-terminal amino acid at position one and an amino acid sequence selected from the group consisting of:

```
                                                        (SEQ ID NO 18)
SMCKPITGTINDLNQQVWTLQGQNLVAVPRSDSVTPVTVAVITCKYPEALEQGRGDPIY

LGIQNPEMCLYCEKVGEQPTLQLKEQKIMDLYGQPEPVKPFLFYRAKTGRTSTLESVAFP

DWFIASSKRDQPIILTSELGKSYNTAFELNIND,
```

```
                                                        (SEQ ID NO 19)
SMCKPITGTINDLNQQVWTLQGQNLVAVPRSDSVTPVTVAVITCKYPEALEQGRGDPIY

LGIQNPEMCLYCEKVGEQPTLQLKEQKIMDLYGQPEPVKPFLFYRAKTGRTSTLESVAFP

DWFIASSKRDQPIILTSELGKSYNTAFELNINDDYKDDDDKHHH,
```

```
                                                        (SEQ ID NO 20)
MMCKPITGTINDLNQQVWTLQGQNLVAVPRSDSVTPVTVAVITCKYPEALEQGRGDPIY

LGIQNPEMCLYCEKVGEQPTLQLKEQKIMDLYGQPEPVKPFLFYRAKTGRTSTLESVAFP

DWFIASSKRDQPIILTSELGKSYNTAFELNIND
and
```

```
                                                        (SEQ ID NO 21)
MMCKPITGTINDLNQQVWTLQGQNLVAVPRSDSVTPVTVAVITCKYPEALEQGRGDPIY
```

LGIQNPEMCLYCEKVGEQPTLQLKEQKIMDLYGQPEPVKPFLFYRAKTGRTSTLESVAFP

DWFIASSKRDQPIILTSELGKSYNTAFELNINDDYKDDDDKHHH.

In another embodiment, a nucleic acid sequence encoding the isolated IL-1F9 polypeptide of the invention is provided. In another aspect of the invention, a recombinant vector that directs expression of a nucleic acid encoding an isolated IL-1F9 polypeptide of the invention is provided. In a particular embodiment, the vector comprises a nucleic acid sequence selected from the group consisting of:

(SEQ ID NO 75)
TCAATGTGTAAACCTATTACTGGGACTATTAATGATTTGAATCAGCAAGTGTGGACC

CTTCAGGGTCAGAACCTTGTGGCAGTTCCACGAAGTGACAGTGTGACCCCAGTCACT

GTTGCTGTTATCACATGCAAGTATCCAGAGGCTCTTGAGCAAGGCAGAGGGGATCCC

ATTTATTTGGGAATCCAGAATCCAGAAATGTGTTTGTATTGTGAGAAGGTTGGAGAA

CAGCCCACATTGCAGCTAAAAGAGCAGAAGATCATGGATCTGTATGGCCAACCCGA

GCCCGTGAAACCCTTCCTTTTCTACCGTGCCAAGACTGGTAGGACCTCCACCCTTGA

GTCTGTGGCCTTCCCGGACTGGTTCATTGCCTCCTCCAAGAGAGACCAGCCCATCATT

CTGACTTCAGAACTTGGGAAGTCATACAACACTGCCTTTGAATTAAATATAAATGAC

TAA, (SEQ ID NO 76)
ATGTCAATGTGTAAACCTATTACTGGGACTATTAATGATTTGAATCAGCAAGTGTGG

ACCCTTCAGGGTCAGAACCTTGTGGCAGTTCCACGAAGTGACAGTGTGACCCCAGTC

ACTGTTGCTGTTATCACATGCAAGTATCCAGAGGCTCTTGAGCAAGGCAGAGGGGAT

CCCATTTATTTGGGAATCCAGAATCCAGAAATGTGTTTGTATTGTGAGAAGGTTGGA

GAACAGCCCACATTGCAGCTAAAAGAGCAGAAGATCATGGATCTGTATGGCCAACC

CGAGCCCGTGAAACCCTTCCTTTTCTACCGTGCCAAGACTGGTAGGACCTCCACCCTT

GAGTCTGTGGCCTTCCCGGACTGGTTCATTGCCTCCTCCAAGAGAGACCAGCCCATC

ATTCTGACTTCAGAACTTGGGAAGTCATACAACACTGCCTTTGAATTAAATATAAAT

GACAGATCTGGCAGTTCTGACTACAAGGACGACGACGACAAGGGCAGTTCTCACCA

TCACCATCACCACTAG
and (SEQ ID NO 77)
ATGATGTGTAAACCTATTACTGGGACTATTAATGATTTGAATCAGCAAGTGTGGACC

CTTCAGGGTCAGAACCTTGTGGCAGTTCCACGAAGTGACAGTGTGACCCCAGTCACT

GTTGCTGTTATCACATGCAAGTATCCAGAGGCTCTTGAGCAAGGCAGAGGGGATCCC

ATTTATTTGGGAATCCAGAATCCAGAAATGTGTTTGTATTGTGAGAAGGTTGGAGAA

CAGCCCACATTGCAGCTAAAAGAGCAGAAGATCATGGATCTGTATGGCCAACCCGA

GCCCGTGAAACCCTTCCTTTTCTACCGTGCCAAGACTGGTAGGACCTCCACCCTTGA

GTCTGTGGCCTTCCCGGACTGGTTCATTGCCTCCTCCAAGAGAGACCAGCCCATCATT

CTGACTTCAGAACTTGGGAAGTCATACAACACTGCCTTTGAATTAAATATAAATGAC

AGATCTGGCAGTTCTGACTACAAGGACGACGACGACAAGGGCAGTTCTCACCATCA

CCATCACCACTAG.

In another aspect, a host cell transfected or transduced with a recombinant vector that directs expression of a nucleic acid encoding an IL-1F9 polypeptide of the invention is provided. In another aspect, a method of producing an isolated IL-1F9 polypeptide of the invention comprising culturing the host cell transfected or transduced with a recombinant vector that directs expression of an IL-1F9 polypeptide of the invention, under conditions promoting expression and isolating the expressed IL-1F9 polypeptide is provided.

In another aspect, a composition, particularly a pharmaceutical composition, comprising an IL-1F9 polypeptide of the invention and a physiologically acceptable diluent, excipient or carrier is provided. A method of stimulating the immune system of an immunosuppresed subject, comprising administering the IL-1F9 polypeptide according of the invention to an immunosuppresed subject in an amount sufficient to stimulate the subject's immune system is provided.

An antibody that specifically binds IL-1F9, where IL-1F9 may be a full length IL-1F9 or a truncant of full length IL-1F9, and prevents proteolytic cleavage thereof, particularly proteolytic cleavage to a more active form where activity is relative to that of the full length IL-1F9, is provided. An antibody that binds an IL-1F9 polypeptide of the invention, and prevents signal transduction/activation through IL-1FRrp2 is also provided. In some embodiments, an antibody binding an IL-1F9 polypeptide selected from the group consisting of: SEQ ID NO 18, SEQ ID NO 19, SEQ ID NO 20 and SEQ ID NO 21, is provided. In some embodiments, the IL-1F9 antibody of the invention, is a monoclonal antibody, particularly a chimeric antibody, a humanized antibody or a fully human antibody. The invention provides a composition, particularly a pharmaceutical composition, comprising the IL-1F9 antibody of the invention and a physiologically acceptable diluent, excipient or carrier.

The invention also provides, a method of treating an inflammatory or autoimmune condition mediated by IL-1Rrp2, comprising administering the IL-1F9 antibody of the invention to a subject in an amount sufficient to ameliorate at least one symptom mediated by IL-1Rrp2 of the condition. In one embodiment, the condition to be treated is an inflammatory condition of the skin, lungs or airways mediated by IL-1Rrp2. In a particular embodiment, the condition to be treated is selected from the group consisting of psoriasis, seborrheic dermatitis, atopic dermatitis, including chronic atopic dermatitis, allergic contact dermatitis, lichen simplex chronicus, pityriasis rubra pilaris, nummular dermatitis, asthma, allergic rhinitis, gastro-esophageal reflux disease, arthritic conditions including, rheumatoid arthritis, psoriatic arthritis, and osteoarthritis. In particular embodiments of the above methods, the subject is a human.

In another aspect, the invention provides a method of identifying a protease that cleaves an IL-1 family member comprising contacting a source of the protease with the IL-1 family member under conditions promoting proteolytic cleavage of the IL-1 family member, and determining if the IL-1 family member has been proteolytically cleaved. The invention further provides a method of identifying an inhibitor of a protease that cleaves an IL-1 family member comprising contacting the protease with the IL-1 family member in the presence, and absence, of a molecule that is a potential inhibitor, under conditions promoting proteolytic cleavage of the IL-1 family member, and determining if the IL-1 family member has been proteolytically cleaved, wherein if the IL-1 family member is not cleaved or is cleaved to a lesser degree in the presence of the molecule, the molecule is an inhibitor.

DETAILED DESCRIPTION

The present invention provides compositions, kits, and methods relating to members of the IL-1 family that require IL-1Rrp2 for signaling or inhibit signaling by competing with IL-1 family members that require IL-1Rrp2 for signaling (hereinafter "IL-1Rrp2 requiring polypeptides", for example, IL-1F5, F6, F8 and F9). Also provided are nucleic acids, and derivatives and fragments thereof, encoding such IL-1 family members. The invention further provides antigen binding proteins that bind to these IL-1 family members. The provided methods include, for example, methods of identifying and/or isolating a protease that cleaves such an IL-1 family member, methods of making, identifying, or isolating molecules that modulate the interaction between an IL-1Rrp2-requiring IL-1 family member and a protease, methods of identifying other IL-1 family members that interact with IL-1 Rrp2 and methods of identifying other IL-1R family members that interact with IL-1F5, F6, F8 and/or F9.

The invention also provides IL-1 Rrp2 requiring polypeptides that have reproducibly high levels of biological activity as a result of the conformation of the amino terminal portion of the polypeptide. As shown in FIG. 1, there is a (Met or Ile)-Xaa-Asp sequence present in each of the IL-1 family members known to require IL-1Rrp2 for signaling (IL-1 F5, F6, F8 and F9), which is marked by underlining of the Met/Ile and the Asp residues. An IL-1Rrp2 requiring polypeptide having an N-terminus nine residues upstream of the Met/Ile is highly active, whereas an IL-1Rrp2 requiring polypeptide extending further upstream is poorly active. IL-1Rrp2 requiring polypeptides that have an N-terminus at eight or seven residues upstream of the Met/Ile are poorly active or inactive. Moreover, the exact amino acid present at N-terminus of the IL-1Rrp2 requiring polypeptides does not appear to be important. Several polypeptides were prepared, some of which had an N-terminal Met initially, which N-terminal Met was cleaved off by an intracellular methionyl aminopeptidase for some polypeptides; for others (those with bulky residues C-terminal to the Met) the aminopeptidase was not able to remove the methionine and for other polypeptides were prepared without an N-terminal Met as described in Example 1 below.

Polynucleotide and polypeptide sequences described herein are indicated using standard one- or three-letter abbreviations. Unless otherwise indicated, each polypeptide sequence has an amino terminus at the left and a carboxy terminus at the right; each single-stranded nucleic acid sequence, and the top strand of each double-stranded nucleic acid sequence, has a 5' terminus at the left and a 3' terminus at the right. A particular polypeptide or polynucleotide sequence also can be described by explaining how it differs from a reference sequence.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "IL-1Rrp2 inhibitor" and "L-1Rrp2 antagonist" are used interchangeably. Each is a molecule that detectably inhibits at least one function of IL-1Rrp2. Conversely, an "IL-1Rrp2 agonist" is a molecule that detectably increases at least one function of IL-1Rrp2. The inhibition caused by an IL-1Rrp2 inhibitor need not be complete so long as it is detectable using an assay. Any assay of a function of IL-1Rrp2 can be used, examples of which are provided herein. Examples of functions of IL-1Rrp2 that can be inhibited by an IL-1Rrp2 inhibitor, or caused or increased by an IL-1Rrp2 agonist, include activation of NFkB signaling pathways; activation of MAP kinases (Erk, JNK, p38) and their signaling pathways; induction of cytokines; induction of chemokines; recruitment of neutrophils; enhancement of skin thickness (e.g., induction of acanthosis and/or hyperkeratosis resembling that found in psoriatic skin), downstream signaling, and so on. Examples of types of IL-1Rrp2 inhibitors and IL-1Rrp2 agonists include, but are not limited to, IL-1Rrp2 requiring polypeptides such as certain IL-1 family members (e.g., IL-1F6, F8 and F9, which are IL-1Rrp2 agonists, and IL-1F5, which is an IL-1Rrp2 antagonist), antibodies, antibody fragments, and antibody derivatives (for example, an antibody that binds an IL-1Rrp2 agonist and prevents proteolytic cleavage thereof).

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence or a tag protein).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts. A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

The present invention also provides non-peptide analogs of IL-IL-1Rrp2-requiring polypeptides. Non-peptide analogs are commonly used in the pharmaceutical industry as drugs with properties analogous to those of the template peptide. These types of non-peptide compound are termed "peptide mimetics" or "peptidomimetics," see, for example, Fauchere, J. Adv. Drug Res. 15:29 (1986); Veber and Freidinger TINS p. 392 (1985); and Evans et al., J. Med. Chem. 30:1229 (1987), which are incorporated herein by reference. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference), for example, by adding internal cysteine residues capable of forming intramolecular disulfide bridges which cyclize the peptide.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with one or more grafted complementarity determining regions (CDRs) or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest*, 5th Ed., US Dept. of Health and Human Services, PHS, NIH, NIH Publication no. 91-3242, 1991.

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies often consist of less than about 10% antibody having specific binding activity for the particular antigen. The percentage of antigen-specific antibody can be increased by using multiple purification steps. Antibodies that are enriched by affinity purification using the antigen are often referred to as "monospecific."

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and CDR fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886, 152 and 5,877,293.

The term "chimeric antibody" refers to an antibody that contains one or more regions from one antibody and one or more regions from one or more other antibodies. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind an IL-1 family member). See, e.g., U.S. Pat. No. 4,816,567 and Morrison, 1985, Science 229:1202-07.

A "neutralizing antibody" or "an inhibitory antibody" is an antibody that inhibits the proteolytic activation of an IL-1 family member when an excess of the anti-IL-1 family member antibody reduces the amount of activation by at least about 20% using an assay such as those described herein in the Examples. In various embodiments, the antibody reduces the amount of amount of proteolytic activation of an IL-1 family member by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., a human IL-1 family member) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma.

Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

IL-1Rrp2 Requiring IL-1 Family Members

In one aspect, the present invention provides proteins (e.g., IL-1 family members, derivative, muteins and variants thereof) that require IL-1Rrp2 for signaling, e.g., human IL-1 F5, F6, F8 and F9. The IL-1 family members in accordance with the present invention include proteins that inhibit a biological activity of IL-1Rrp2, as well as proteins that stimulate a biological activity of IL-1Rrp2. Examples of such biological activities include activation of multiple kinase pathways, including ERK, p38MAPK, JNK, and IKK. In the skin, IL-1Rrp2 signaling can lead to an acanthotic, hyperkeratotic epidermis that resembles psoriatic skin, and in the lung it causes the recruitment of neutrophils.

Different IL-1 family members may utilize different domains of IL-1Rrp2 for signaling, or act by different mechanisms of action. Examples include but are not limited to proteins that cause signal transduction via IL-1Rrp2, and proteins that inhibit signal transduction. The site of action may be, for example, intracellular (e.g., by interfering with an intracellular signaling cascade) or extracellular. An antagonistic protein need not completely inhibit IL-1Rrp2 activity to find use in the present invention; rather, antagonistic proteins that reduce a particular activity of IL-1Rrp2 are contemplated for use as well. Discussions herein of particular mechanisms of action for antagonistic proteins in treating particular diseases are illustrative only, and the methods presented herein are not bound thereby.

Other derivatives of the IL-1 family members within the scope of this invention include covalent or aggregative conjugates of the proteins, or fragments thereof, with other proteins or polypeptides, such as by expression of recombinant fusion proteins comprising heterologous polypeptides fused to the N-terminus or C-terminus of an IL-1Rrp2 requiring protein. For example, the conjugated peptide may be a heterologous signal (or leader) polypeptide, e.g., the yeast alpha-factor leader, or a peptide such as an epitope tag. IL-1Rrp2 requiring protein-containing fusion proteins can comprise peptides added to facilitate purification or identification of IL-1Rrp2 requiring polypeptides (e.g., poly-His). An IL-1Rrp2 requiring polypeptides also can be linked to the FLAG® peptide (DYKDDDDK; SEQ ID NO:5), described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Additional, useful tag proteins include green fluorescent protein (GFP; Chalfie et al., *Science* 263:802, 1994), an N-terminal peptide that contains recognition sites for a monoclonal antibody, a specific endopeptidase, and a site-specific protein kinase (PKA; Blanar and Rutter, *Science* 256:1014, 1992), birA (Altman et al., *Science* 274:94, 1996) and glutathione S transferase (GST: Smith and Johnson, *Gene* 67:31, 1988).

Oligomers that contain one or more IL-1Rrp2 requiring proteins may be employed as agonists or antagonists. Oligomers may be in the form of covalently-linked or non-covalently-linked dimers, trimers, or higher oligomers. Oligomers comprising two or more IL-1Rrp2 requiring proteins are contemplated for use, with one example being a homodimer. Other oligomers include heterodimers, homotrimers, heterotrimers, homotetramers, heterotetramers, etc.

One embodiment is directed to oligomers comprising multiple IL-1Rrp2 requiring proteins joined via covalent or non-covalent interactions between peptide moieties fused to the IL-1Rrp2 requiring proteins. Such peptides may be peptide linkers (spacers), or peptides that have the property of promoting oligomerization. Leucine zippers and certain polypeptides derived from antibodies are among the peptides that can promote oligomerization of IL-1Rrp2 requiring proteins attached thereto, as described in more detail below.

In particular embodiments, the oligomers comprise from two to four IL-1Rrp2 requiring proteins. The IL-1Rrp2 requiring proteins of the oligomer may be in any form, such as any of the forms described above, e.g., variants or fragments. Preferably, the oligomers comprise IL-1Rrp2 requiring proteins that have activity (i.e., IL-1Rrp2 agonistic or antagonistic activity).

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins," in *Current Protocols in Immunology*, Suppl. 4, pages 10.19.1-10.19.11.

One embodiment of the present invention is directed to a dimer comprising two fusion proteins created by fusing an IL-1Rrp2 requiring polypeptides or fragment thereof to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed there from) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, an IL-1Rrp2 requiring polypeptide or fragment thereof may be substituted for the variable portion of an antibody heavy and/or light chain.

Alternatively, the oligomer is a fusion protein comprising multiple IL-1Rrp2 requiring proteins, with or without peptide linkers (spacer peptides). Among the suitable peptide linkers are those described in U.S. Pat. Nos. 4,751,180 and 4,935,233.

Another method for preparing oligomeric IL-1Rrp2 requiring proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an IL-1Rrp2 requiring protein, fragment or derivative fused to a leucine zipper peptide is expressed in suitable host cells, and the soluble oligomeric IL-1Rrp2 requiring polypeptides fragments or derivatives that form are recovered from the culture supernatant.

Antigen Binding Proteins

The present invention also provides antigen binding proteins that bind an IL-1Rrp2 requiring polypeptides (for example, an IL-1Rrp2 agonist or antagonist). Numerous types of antigen binding proteins and methods of making them are known in the art. In one aspect, the present invention provides antigen binding proteins that interfere with the proteolytic activation of an IL-1Rrp2 requiring polypeptides. Such antigen binding proteins can be made against an IL-1 family member such as IL-1F6, F8 or F9 (or F5), or a fragment, variant or derivative thereof, and screened in conventional assays for the ability to interfere with proteolytic activation of the IL-1Rrp2 requiring protein.

In another aspect, the present invention includes an antigen binding protein that demonstrates species selectivity, and an antigen binding protein that has one or more of the following characteristics: binds to both human and murine IL-1Rrp2 requiring protein, inhibits the proteolytic activation of human IL-1Rrp2 requiring protein, inhibits the proteolytic activation of murine IL-1Rrp2 requiring protein, binds to or near the proteolytic cleavage site of IL-1Rrp2 requiring protein, causes relatively little down-regulation of cell-surface expressed IL-1Rrp2.

Fragments of antigen binding proteins are also included. Antigen-binding fragments of antigen binding proteins of the invention may be produced by conventional techniques. Examples of such fragments include, but are not limited to, Fab and $F(ab')_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans.

Also included are human or partially human antibodies prepared in non-human animals (for example, mice in which one or more endogenous immunoglobulin genes have been inactivated and replaced with human immunoglobulin). Antibodies produced in the animal incorporate human immunoglobulin polypeptide chains encoded by the human genetic material introduced into the animal.

In another aspect, the present invention provides monoclonal antibodies that bind to IL-1Rrp2 requiring protein(s). Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas.

Monoclonal antibodies secreted by a hybridoma cell line can be purified using any technique known in the art. Hybridomas or mAbs may be further screened to identify mAbs with particular properties, such as the ability to block an IL-1Rrp2 induced activity. Examples of such screens are provided in the examples below.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to IL-1Rrp2 requiring proteins.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

In one aspect, the present invention provides antigen-binding fragments of an anti-IL-1Rrp2 requiring polypeptides antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

In another aspect, the present invention provides an antigen binding protein that binds at or near the protease cleavage site of human IL-1 F6, F8 or F9, or IL-1 F5. Antigen binding proteins that bind to the protease cleavage site can be made using any technique known in the art. For example, such antigen binding proteins can be isolated using the full-length an IL-1Rrp2 requiring protein, or a smaller fragment thereof comprising or consisting of the protease cleavage site (examples of which are provided herein). Antigen binding proteins so isolated can be screened to determine their binding specificity using any method known in the art (examples of which are provided herein). Such antigen binding proteins that function as IL-1Rrp2 antagonists may be employed in treating any IL-1Rrp2-induced condition, including but not limited to inflammatory conditions.

The present invention further provides multi-specific antigen binding proteins, for example, bispecific antigen binding protein, e.g., antigen binding protein that bind to two different epitopes of an IL-1Rrp2 requiring protein, or to an epitope of one IL-1Rrp2 requiring polypeptide and an epitope of another IL-1Rrp2 requiring protein, via two different antigen binding sites or regions. Numerous methods of preparing bispecific antibodies are known in the art.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired Peptibodies An additional class of compounds useful in the practice of the methods of the present invention are compounds sometimes referred to as peptibodies. Such compounds are biologically active peptides having an increased in vivo half-life and reduced immunogenicity profile. This is accomplished by fusion of the peptide(s) with a vehicle, as described in U.S. Pat. No. 6,660,843 (the disclosure of which is incorporated by reference herein). Briefly, pharmacologically active compounds are prepared selecting at least one peptide that modulates the activity of a protein of interest, e.g., in this case selecting a peptide that antagonizes the activity of an IL-1Rrp2 requiring polypeptide (e.g., IL-1F6, F8, F9, or IL-1F5), as in a peptide that inhibits proteolytic cleavage of an IL-1Rrp2 agonist; and preparing a fusion protein of the selected peptide and multimerizing vehicle One such vehicle is an Fc domain. The peptides screened as described above are expressed in a phage display library. The vehicle and the peptide may be linked through the N- or C-terminus of the peptide or the vehicle, as described further in U.S. Pat. No. 6,660,843. Derivatives of the above compounds are also encompassed by this invention.

Antagonistic molecules useful in the processes of this invention may be prepared by standard synthetic methods, recombinant DNA techniques, or any other methods of preparing peptides and fusion proteins. Compounds of this invention that encompass non-peptide portions may be synthesized by standard organic chemistry reactions, in addition to standard peptide chemistry reactions when applicable.

Peptibodies may be used to prepare derivative and other forms thereof, substantially as described for antibodies.

Nucleic Acids

In one aspect, the present invention provides isolated nucleic acid molecules. The nucleic acids comprise, for example, polynucleotides that encode all or part of an IL-1Rrp2 requiring polypeptide, for example, IL-1 F5, F6, F8 or F9, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, antisense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Changes can be introduced by mutation into a nucleic acid, thereby leading to changes in the amino acid sequence of a polypeptide (e.g., an IL-1Rrp2 requiring polypeptides) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property (e.g., binding to IL-1Rrp2 or blocking the proteolytic activation of an IL-1 family member such as IL-1 F5, F6, F8 or F9).

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, E. coli) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Expression of Recombinant Proteins or Polypeptides

Any expression system known in the art can be used to make the recombinant polypeptides of the invention (i.e., recombinant IL-1Rrp2 polypeptides, recombinant antigen binding proteins, peptibodies and the like). In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10:2821. Appropriate cloning and expression vectors for use with bacterial, fungal, yeast, and mammalian cellular hosts are described by Pouwels et al. (*Cloning Vectors: A Laboratory Manual*, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., in the case of an antigen binding protein, over a matrix having all or a portion of the antigen (e.g., an IL-1Rrp2 requiring polypeptides or portion thereof) bound thereto, or in the case of an IL-1Rrp2 requiring protein, over a matrix having all or a portion of IL-1Rrp2, or an antigen binding protein that binds the IL-1Rrp2 requiring protein bound thereto. Polypeptides or proteins contemplated for use herein include substantially homogeneous recombinant mammalian IL-1Rrp2 requiring polypeptides, and/or antibodies thereto, substantially free of contaminating endogenous materials.

The proteins may be prepared, and screened for desired properties, by any of a number of known techniques. Certain of the techniques involve isolating a nucleic acid encoding a polypeptide chain (or portion thereof) of an IL-1Rrp2 requiring polypeptides of interest (e.g., IL-1F6, F8 or F (or IL-1F5), and manipulating the nucleic acid through recombinant DNA technology. Nucleic acids encoding antigen binding proteins that bind an IL-1Rrp2 requiring polypeptides can be similarly manipulated. The nucleic acid may be fused to another nucleic acid of interest, or altered (e.g., by mutagenesis or other conventional techniques) to add, delete, or substitute one or more amino acid residues, for example.

Protease Isolation and Assay

The IL-1Rrp2 requiring proteins described herein will also be useful in identifying and/or isolating a protease or proteases that cleave the IL-1Rrp-2 requiring proteins to yield the bioactive form thereof. Useful methods are described, for example, in the *Handbook Of Proteolytic Enzymes, Second Edition*, edited by A. Barrett, N. Rawlings and J. Woessner (Academic Press, 2004). In general, methods for identifying the protease(s) might include (a) testing known proteases for their ability to generate biologically active material; (b) screening cell supernatants, membranes, or lysates for their ability to generate biologically active material; and (c) using the full-length (uncleaved) IL-1Rrp2 requiring protein as an affinity reagent to purify the protease(s).

For example, known proteases can be tested for the ability to cleave an IL-1 Rrp2 requiring protein into bioactive form by contacting a known protease with the IL-1 Rrp2 requiring protein under conditions promoting protease activity, than determining what effect, if any, the protease had upon the biological activity of the IL-1Rrp2 requiring polypeptides (for example, activity as an agonist or an antagonist as described herein). Cells that express a protease (or proteases) that cleave IL-1Rrp2 requiring proteins, either intracellularly, as a soluble polypeptide or as a cell-surface associated protein, can be identified in a similar manner. It may further be possible to use an IL-1Rrp2 requiring protein to select a cell population enriched for protease expression by using a panning or cell sorting technique, many of which are known in the art. When a cellular source of the protease has been identified, the IL-1Rrp2 requiring protein(s) can be used in an effort to isolate the protease.

Specific screening methods are known in the art and along with integrated robotic systems and collections of chemical compounds/natural products are extensively incorporated in high throughput screening so that large numbers of test compounds can be tested for activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence.

One such assay is based on fluorescence resonance energy transfer (FRET; for example, HTRF®, Packard Instrument Company, Meriden, Conn.; LANCE™, PerkinElmer Life-Sciences, Wallac Oy., Turku, Finland) between two fluorescent labels, an energy donating long-lived chelate label and a short-lived organic acceptor. The energy transfer occurs when the two labels are brought in close proximity via the molecular interaction between an IL-1Rrp2 polypeptide and a protease that cleaves it.

Indications

In one aspect, the present invention provides methods of treating a subject. The method can, for example, have a generally salubrious effect on the subject, e.g., it can increase the subject's expected longevity. Alternatively, the method can, for example, treat, prevent, relieve, or ameliorate ("treat") a disease, disorder, condition, or illness ("a condition"). Among the conditions to be treated in accordance with the present invention are conditions characterized by inappropriate expression or activity of IL-1Rrp2 and/or agonists or antagonists thereof (e.g., IL-1F6, F8 and/or F9 for the former, IL-1F5 for the latter). In some such conditions, the expression or activity level of the receptor or agonist(s) thereof is too high; in other cases the expression or activity level of an antagonist(s) thereof is too low. Treatment comprises administering an IL-1Rrp2 antagonist as described herein.

Conditions that fall within this category often exhibit an inflammatory skin phenotype with characteristics common to those seen in human psoriatic skin. Such characteristic include acanthosis, hyperkeratosis, dermal infiltrate, increased expression of keratin 6, increased expression of keratin 14, increased expression of ICAM-1 in dermis, basal keratinocytes and blood vessels, increased expression of macrophage marker BM8 in dermis and decreased expression in epidermis, and decreased expression of T cell marker CD3 in epidermis.

Specific medical conditions and diseases that are treatable or preventable with the IL-1Rrp2 antagonists of this invention include those associated with inflammatory skin diseases including, but not limited to psoriasis, seborrheic dermatitis, atopic dermatitis (including chronic atopic dermatitis or CAD), allergic contact dermatitis, lichen simplex chronicus, pityriasis rubra pilaris and nummular dermatitis.

Moreover, normal airway epithelium has relatively high expression of IL-1 family members F5, F6, F8 and F9, as well as the receptor IL-1Rrp2, and intranasal instillation of F8 or F9 leads to an influx of neutrophils into the lung. Accordingly IL-1Rrp2 antagonists may be indicated for inflammatory conditions of the airway, for example asthma and allergic rhinitis. IL-1F9 and IL-1Rrp2 are highly expressed in the esophagus, and the interaction between this cytokine/receptor pair may play a role in gastro-esophageal reflux disease (GERD), which may accordingly be ameliorated by IL-1Rrp2 antagonists.

IL-1 F8 and IL-1 Rrp2 are also expressed in synovial fibroblasts and chondrocytes, and are induced to higher levels in those cells by IL-1 and TNF. Moreover, these cells respond to exogenous IL-1 F8 by synthesizing IL-6, IL-8 and nitric oxide. Accordingly, the IL-1Rrp2 antagonists of the invention may have use in arthritic conditions mediated by the induced polypeptides (i.e., rheumatoid arthritis, psoriatic arthritis, other arthritic conditions in which TNF and/or IL-1 play a role, and osteoarthritis and related conditions in which nitric oxide plays a role)

The methods described herein can be treated with the IL-1 Rrp2 antagonists of this invention in combination with other cytokines, cytokine inhibitors and reagents (also referred to herein as immunomodulators). For example, IL-18 antagonists; including soluble IL-18 receptor, antibodies to IL-18 or the IL-18 receptor, IL-18 binding protein; TNF inhibitors, including ENBREL®; IL-1 inhibitors, including soluble forms of type II IL-1R, type II IL-1R, antibodies to IL-1, antibodies to type I IL-1R; and or other active agents that are effective in treating the disclosed medical conditions and diseases.

The compositions and/or methods of the present invention also can be used, for example, in cosmetic treatments, in veterinary treatments, to increase longevity, to treat reproductive defects, and to treat a variety of IL-1Rrp2 related disorders. In addition, in certain such conditions, the expression or activity level of IL-1Rrp2 agonists is too low, and the treatment comprises administering an IL-1Rrp2 agonist such as IL-1F6, F8 and/or F9; such treatments are also comprehended herein.

Therapeutic Methods and Administration of IL-1Rrp2 Antagonists

Certain methods provided herein comprise administering an IL-1 Rrp2 antagonist to a subject, thereby reducing an IL-1 family member-induced biological response that plays a role in a particular condition. In particular embodiments, methods of the invention involve contacting endogenous IL-1Rrp2-expressing cells with an IL-1Rrp2 antagonist, e.g., via administration to a subject or in an ex vivo procedure.

The term "treatment" encompasses alleviation or prevention of at least one symptom or other aspect of a disorder, or reduction of disease severity, and the like. An IL-1 Rrp2 antagonist need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an IL-1Rrp2 antagonist in an amount and for a time sufficient to induce a sustained improvement over baseline of an indicator that reflects the severity of the particular disorder.

As is understood in the pertinent field, pharmaceutical compositions comprising the molecules of the invention are administered to a subject in a manner appropriate to the indication. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of IL-1Rrp2 antagonist s thereto in ex vivo procedures also is contemplated. For example, a patient's blood or other bodily fluid may be contacted with an IL-1Rrp2 requiring polypeptides that binds an enzyme such as a protease ex vivo. The IL-1Rrp2 requiring polypeptides may be bound to a suitable insoluble matrix or solid support material.

Advantageously, IL-1Rrp2 antagonist are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to an IL-1Rrp2 antagonist.

In one embodiment, the pharmaceutical composition comprise an IL-1Rrp2 antagonist of the invention together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, 16$^{th}$ Ed. (1980) and 20$^{th}$ Ed. (2000), Mack Publishing Company, Easton, Pa.

Kits for use by medical practitioners include an IL-1Rrp2-inhibiting substance of the invention and a label or other instructions for use in treating any of the conditions discussed herein. In one embodiment, the kit includes a sterile preparation of one or more IL-1Rrp2 antagonist s thereto, which may be in the form of a composition as disclosed above, and may be in one or more vials.

Dosages and the frequency of administration may vary according to such factors as the route of administration, the particular IL-1Rrp2 antagonists employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

A IL-1Rrp2-inhibiting substance of the invention may be administered, for example, once or more than once, e.g., at regular intervals over a period of time. In particular embodiments, an IL-1Rrp2 antagonist is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the IL-1Rrp2 antagonist is administered until the patient manifests a medically relevant degree of improvement over baseline for the chosen indicator or indicators.

Particular embodiments of the present invention involve administering an IL-1Rrp2 antagonist at a dosage of from about 1 ng of protein per kg of subject's weight per day ("1 ng/kg/day") to about 10 mg/kg/day, more preferably from about 500 ng/kg/day to about 5 mg/kg/day, and most preferably from about 5 micrograms/kg/day to about 2 mg/kg/day, to a subject. In additional embodiments, an IL-1Rrp2 antagonist is administered to adults one time per week, two times per week, or three or more times per week, to treat an IL-1Rrp2-mediated disease, condition or disorder, e.g., a medical disorder disclosed herein. If injected, the effective amount of IL-1Rrp2 antagonist per adult dose may range from 1-20 mg/m$^2$, and preferably is about 5-12 mg/m$^2$. Alternatively, a flat dose may be administered; the amount may range from 5-100 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of IL-1Rrp2 antagonist to one to three times per week over a period of at least three weeks, though treatment for longer periods may be necessary to induce the desired degree of improvement. For pediatric subjects (age 4-17), one exemplary suitable regimen involves the subcutaneous injection of 0.4 mg/kg, up to a maximum dose of 25 mg of IL-1Rrp2 antagonist administered two or three times per week.

Particular embodiments of the methods provided herein involve subcutaneous injection of from 0.5 mg to 10 mg, preferably from 3 to 5 mg, of an IL-1Rrp2 antagonist, once or twice per week. Another embodiment is directed to pulmonary administration (e.g., by nebulizer) of 3 or more mg of IL-1Rrp2 antagonist once a week.

Examples of therapeutic regimens provided herein comprise subcutaneous injection of an IL-1Rrp2 antagonist once a week, at a dose of 1.5 to 3 mg, to treat a condition in which IL-1Rrp2 signaling plays a role. Examples of such conditions are provided herein and include, for example, inflammatory conditions of the skin, including, but not limited to psoriasis, seborrheic dermatitis, atopic dermatitis (including chronic atopic dermatitis or CAD), allergic contact dermatitis, lichen simplex chronicus, pityriasis rubra pilaris and nummular dermatitis. Weekly administration of IL-1Rrp2 antagonist is continued until a desired result is achieved, e.g., the subject's symptoms subside. Treatment may resume as needed, or, alternatively, maintenance doses may be administered.

Other examples of therapeutic regimens provided herein comprise subcutaneous or intravenous administration of a dose of 1, 3, 5, 6, 7, 8, 9, 10, 11, 12, 15, or 20 milligrams of an IL-1Rrp2 inhibitor of the present invention per kilogram body mass of the subject (mg/kg). The dose can be administered once to the subject, or more than once at a certain interval, for example, once a day, three times a week, twice a week, once a week, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

In another embodiment, an IL-1Rrp2 antagonist is administered to the subject in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionnaires that are administered to the subject, such as quality-of-life questionnaires developed for a given disease.

Elevated levels of IL-1Rrp2, IL-1F6, IL-1F8 and/or IL-1F9 and/or activation of thereof, and/or decreased levels and/or activation of IL-1F5, are associated with a number of disorders, including, for example, inflammatory conditions of the skin, including, but not limited to psoriasis, seborrheic dermatitis, atopic dermatitis (including chronic atopic dermatitis or CAD), allergic contact dermatitis, lichen simplex chronicus, pityriasis rubra pilaris and nummular dermatitis. Other such conditions include inflammatory conditions of the airway, of the esophagus, and the joints.

Subjects with a given disorder may be screened, to identify those individuals who have elevated IL-1Rrp2, IL-1F6, IL-1F8 and/or IL-1F9 activation (or decreased IL-1F5 activation), thereby identifying the subjects who may benefit most from treatment with an IL-1Rrp2 antagonist. Thus, treatment methods provided herein optionally comprise a first step of measuring a subject's IL-1Rrp2, IL-1F6, IL-1F8 and/or IL-1F9 (or IL-1F5) activation levels. An IL-1Rrp2 antagonist may be administered to a subject in whom IL-1Rrp2, IL-1F6, IL-1F8 and/or IL-1F9 activation is elevated above normal, and/or whose IL-1F5 activity is below normal.

A subject's levels of IL-1Rrp2, IL-1F6, IL-1F8, IL-1F9 and/or IL-1F5 activity may be monitored before, during and/or after treatment with an IL-1Rrp2 antagonist, to detect changes, if any, in IL-1Rrp2, IL-1F6, IL-1F8, IL-1F9 and/or IL-1F5 activity. For some disorders, the incidence of elevated IL-1Rrp2, IL-1F6, IL-1F8 and/or IL-1F9 activity, or decreased IL-1F5 activity, may vary according to such factors as the stage of the disease or the particular form of the disease. Known techniques may be employed for measuring IL-1Rrp2, IL-1F6, IL-1F8, IL-1F9 and/or IL-1F5 activity, e.g., in a subject's serum, blood or tissue samples. IL-1Rrp2, IL-1F6, IL-1F8, IL-1F9 and/or IL-1F5 activity may be measured using any suitable technique.

Particular embodiments of methods and compositions of the invention involve the use of an IL-1Rrp2 antagonist and one or more additional IL-1Rrp2 antagonists, for example, two or more IL-1Rrp2 requiring proteins of the invention, two or more antigen binding proteins of the invention, or combinations of IL-1Rrp2 requiring proteins and antigen binding proteins. In further embodiments, IL-1Rrp2 antagonists are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an IL-1Rrp2 antagonist is administered at least once during a course of treatment that involves administering at least one other therapeutic agent to the patient.

Examples of other agents that may be co-administered with an IL-1 Rrp2 antagonist are other IL-1Rrp2 requiring proteins or antigen binding proteins, or therapeutic polypeptides that are chosen according to the particular condition to be treated. Alternatively, non-proteinaceous drugs that are useful in treating one of the particular conditions discussed above may be co-administered with IL-1Rrp2 antagonist.

Combination Therapy

In another aspect, the present invention provides a method of treating a subject with an IL-1Rrp2 antagonist, and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In another embodiment, a combination therapy method comprises administering to the subject two, three, four, five, six, or more of the agonists or antagonists described herein. In another embodiment, the method comprises administering to the subject two or more treatments that together inhibit or activate (directly or indirectly) IL-1Rrp2-mediated signal transduction. Examples of such methods include using combinations of two or more IL-1Rrp2 requiring proteins and/or antigen binding proteins, an IL-1Rrp2 requiring polypeptide or antigen binding protein and one or more other therapeutic moiety having anti-inflammatory properties (for example, non-steroidal anti-inflammatory agents, steroids, and/or immunomodulators), or an IL-1Rrp2 requiring polypeptide or antigen binding protein and one or more other treatments (e.g., surgery, ultrasound, or treatment effective to reduce inflammation). Furthermore, one or more IL-1Rrp2 antagonist can be used in combination with one or more molecules or other treatments, wherein the other molecule(s) and/or treatment(s) do not directly bind to or affect IL-1Rrp2, but which combination is effective for treating or preventing the condition being treated. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the IL-1Rrp2 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

The specification is most thoroughly understood in light of the teachings of the references cited within the specification, which are hereby incorporated by reference. The following examples, both actual and prophetic, are provided for the purpose of illustrating specific embodiments or features of the instant invention and do not limit its scope.

EXAMPLE 1

Example 1A

Preparation of IL-1F6 Variants

This example describes the preparation of various N-terminal variants of IL-1F6. The various N-terminal deletion variants are shown in Table 1 below:

TABLE 1

Amino Acid Sequence of IL-1F6 Variants

| N-Terminal amino acid sequence of IL-1F6 Variants SEQ (. . . indicates intervening amino acids of human IL-1F6 (SEQ ID NO ID 2; FLAG indicates the amino acid sequence DYKDDDDK; polyHis NO: indicates a chain of multiple histidines, typically about 6) | IL-1F6 Variant Polypeptides: (Hu indicates human; WT indicates full length wild type polypeptide, FpH indicates a FLAG poly His tag., the bold, italicized, upper case letter and number refers to the indicated amino acid and its position in SEQ ID NO 2 where the position is relative to the N-Terminal amino acid at position one of SEQ ID NO 2.) |
|---|---|
| 22 MEKALKIDTPQQGSIQDI . . . FGLTMLF-FLAG-polyHis | HuIL-1F6WT/FpH |
| 23 MKIDTPQQGSIQDI . . . FGLTMLF-FLAG-polyHis | HuIL-1F6*K6*/FpH |
| 24 MIDTPQQGSIQDI . . . FGLTMLF-FLAG-polyHis | HuIL-1F6*I7*/FpH |
| 25 MDTPQQGSIQDI . . . FGLTMLF-FLAG-polyHis | HuIL-1F6*D8*/FpH |
| 26 KIDTPQQGSIQDI . . . FGLTMLF | HuIL-1F6*K6* |

Note: The IL1-F6 polypeptide occurs in 2 isotypes. One isotype comprises a Q at amino acid 12, relative to the M a position one of the wild type IL-1F6 indicated in Table 1 as SEQ ID NO 22 and another that encodes R at position 12. Variants of both isotypes are provided by the compositions and methods of the invention.

The N-terminal variants that comprise a FLAG-polyHis C-terminal tag were prepared as described immediately below. N-terminal variants were amplified via PCR using as a template a cDNA clone encoding huIL-1F6 (AF201831). An N-terminal methionine was placed directly before the desired starting amino acid of each variant for proper translational initiation. FLAG® (Sigma-Aldrich, St. Louis, Mo.) and poly-His tags were added to the C-terminus for purification/detection. NdeI and XhoI sites were added to the 5' and 3' ends, respectively. The resulting amplicons were digested with NdeI and XhoI and subcloned into the *E. coli* expression vector, pAMG21 (ATCC # 98113). The resulting constructs were introduced into *E. coli* DH10B and expression was induced by the addition of [N-(3-oxo-hexanoyl)homoserine lactone]. The expressed polypeptides were then purified from bacterial lysates (soluble fraction) by affinity chromatography using Ni-NTA columns (Qiagen, Germantown, Md. Cat #30600) as per manufacturer's protocol, and tested for activity in a reporter assay substantially as described in Example 2. Results are shown in Table 5 below.

The N-terminal variant, HuIL-1F6K6, was prepared by PCR amplifying a template cDNA clone encoding huIL-1F6K6 variant. The primers used in PCR allowed the PCR products to be placed using the In-Fusion™ PCR cloning system (Clontech, Mountain View, Calif., cat# 631774), in accordance with manufacturer's protocol, into a pET-SUMO vector (Invitrogen, Carlsbad, Calif., cat K300-01). This procedure put a pH-SUMO tag 5' to the desired starting amino acid of the IL-1F6 variant in the vector resulting in the following nucleic acid sequence where the pH SUMO tag runs from the 5' end to the underlined nucleotide in bold which indicates the start of the nucleic acid sequence encoding HuIL-1F6K6:

(SEQ ID NO 78)
ATGGGCAGCAGCCATCATCATCATCATCACGGCAGCGGCCTGGTGCCGCG

CGGCAGCGCTAGCATGTCGGACTCAGAAGTCAATCAAGAAGCTAAGCCAG

AGGTCAAGCCAGAAGTCAAGCCTGAGACTCACATCAATTTAAAGGTGTCC

GATGGATCTTCAGAGATCTTCTTCAAGATCAAAAAGACCACTCCTTTAAG

AAGGCTGATGGAAGCGTTCGCTAAAAGACAGGGTAAGGAAATGGACTCCT

TAAGATTCTTGTACGACGGTATTAGAATTCAAGCTGATCAGACCCCTGAA

GATTTGGACATGGAGGATAACGATATTATTGAGGCTCACAGAGAACAGAT

TGGTGGTAAAATTGACACACCTCAGCGGGGGAGCATTCAGGATATCAATC

ATCGGGTGTGGGTTCTTCAGGACCAGACGCTCATAGCAGTCCCGAGGAAG

GACCGTATGTCTCCAGTCACTATTGCCTTAATCTCATGCCGACATGTGGA

GACCCTTGAGAAAGACAGAGGGAACCCCATCTACCTGGGCCTGAATGGAC

TCAATCTCTGCCTGATGTGTGCTAAAGTCGGGGACCAGCCCACACTGCAG

CTGAAGGAAAAGGATATAATGGATTTGTACAACCAACCCGAGCCTGTGAA

GTCCTTTCTCTTCTACCACGCCAGAGTGGCAGGAACTCCACCTTCGAGT

CTGTGGCTTTCCCTGGCTGGTTCATCGCTGTCAGCTCTGAAGGAGGCTGT

CCTCTCATCCTTACCCAAGAACTGGGGAAAGCCAACACTACTGACTTTGG

GTTAACTATGCTGTTTTAA.

The resulting construct was introduced into *E. coli* DH10B. Expression was carried out using Overnight Express™ Autoinduction System (Novagen, Darmstadt, Germany, cat# 71300-3) per manufacturer's protocol. The *E. Coli* cells were centrifuged and frozen.

Frozen *E. coli* cell pellets were thawed in TBS made in Roche Complete EDTA free protease inhibitor cocktail. After thawing, benzonase was added. Cells were lysed via passage through a Microfluidics microfluidizer 110L device (MFIC Corporation, Newton, Mass.) and resulting lysates clarified via centrifugation. Supernatants were sterile filtered and loaded onto 5 mL HisTrap (GE Biosciences, Piscataway, N.J.) Ni-sepharose columns equilibrated in Tris, NaCl, imidazole pH 7.4. Columns were washed with imidazole in TBS.

Protein was eluted with a imidazole linear gradient. Eluted fractions were pooled and dialyzed into PBS using MWCO Slide-A-Lyzers (Pierce Biotechnology, Inc., Rockland, Ill.). LifeSensors SUMO Protease-1 was used to cleave the His-SUMO fusion partner from IL-1F6 variant. Cleavage reaction products were dialyzed into TBS containing EDTA, pH 7.4 using MWCO Slide-A-Lyzers. Dialyzed pools were then passed back over HisTrap Ni-Sepharose columns and flow-through fractions containing pure liberated IL-1F6 variant were retained. and tested for activity as described in Example 2B below. Results are shown in Table 7 below.

Example 1B

Preparation of IL-1F8 Variants

Variants of IL-1F8 comprising a FLAG-polyHis tag were prepared in a substantially similar manner as for IL-F6 FLAG-polyHis tag variants described in Example 1A above, using as a template a cDNA clone encoding huIL-1F8 (AF201833). Likewise, HuIL-1F8R5 (lacking a FLAG-polyHis tag), using as a template a cDNA clone encoding huIL-1F8 (AF201833), was prepared and purified in a substantially similar manner to HuIL-1F6K6 described in Example 1A above. The various N-terminal deletion variants are shown in Table 2 below:

TABLE 2

Amino Acid Sequence of IL-1F8 Variants

| SEQ ID NO: | N-Terminal amino acid sequence of IL-1F8 Variants ( . . . indicates intervening amino acids of human IL-1F8 (SEQ ID NO 3); ( ) indicates that the enclosed amino acid is removed; FLAG indicates the amino acid sequence DYKDDDDK; polyHis indicates a chain of multiple histidines, typically 6) | IL-1F8 Variant Polypeptide: (Hu indicates human; WT indicates full length wild type polypeptide, FpH indicates a FLAG poly His tag., he bold, italicized, upper case letter and number refers to the indicated amino acid and its position in SEQ ID NO 3 where the position is relative to the N-Terminal amino acid at position one of SEQ ID NO 3.) |
|---|---|---|
| 27 | MNPQREAAPKSYAIR . . . FYLDSVE-FLAG-polyHis | HuIL-1F8WT/FpH |
| 28 | MQREAAPKSYAIR . . . FYLDSVE-FLAG-polyHis | HuIL-1F8 *Q4*/FpH |
| 29 | MREAAPKSYAIR . . . FYLDSVE-FLAG-polyHis | HuIL-1F8 *R5*/FpH |
| 30 | MEAAPKSYAIR . . . FYLDSVE-FLAG-polyHis | HuIL-1F8 *E6*/FpH |
| 31 | (M)AAPKSYAIR . . . FYLDSVE-FLAG-polyHis | HuIL-1F8 *A7*/FpH |
| 32 | REAAPKSYAIR . . . FYLDSVE | HuIL-1F8R5 |

The FLAG-polyHis constructs were expressed in *E. coli*, and the expressed polypeptides purified from bacterial lysates (soluble fraction) by affinity chromatography using Ni-NTA columns (Qiagen Cat #30600) as per manufacturer's protocol. N-terminal sequencing indicated that, for one construct (HuIL-1F8A7/FpH), the N-terminal Met was removed (designated parenthetically in Table 2). Purified polypeptides were tested for activity in a reporter assay substantially as described in Example 2; results are shown in Table 5 below.

The pH-SUMO construct, encoding HuIL-1F8R5 was introduced into *E. coli* DH10B. Expression was carried out using Overnight Express™ Autoinduction System (Novagen, Darmstadt, Germany, cat# 71300-3) per manufacturer's protocol. The *E. coli* cells were centrifuged and frozen. Frozen *E. coli* cell pellets were thawed in TBS made in Roche Complete EDTA free protease inhibitor cocktail. After thawing, benzonase was added. Cells were lysed via passage through a Microfluidics microfluidizer 110L device (MFIC Corporation, Newton, Mass.) and resulting lysates clarified via centrifugation. Supernatants were sterile filtered and loaded onto 5 mL HisTrap (GE Biosciences, Piscataway, N.J.) Ni-sepharose columns equilibrated in Tris, NaCl, imidazole pH 7.4. Columns were washed with imidazole in TBS. Protein was eluted with a imidazole linear gradient. Eluted fractions were pooled and dialyzed into PBS using MWCO Slide-A-Lyzers (Pierce Biotechnology, Inc., Rockland, Ill.). LifeSensors SUMO Protease-1 was used to cleave theHis-SUMO fusion partner from IL-1F6 variant. Cleavage reaction products were dialyzed into TBS containing EDTA, pH 7.4 using MWCO Slide-A-Lyzers. Dialyzed pools were then passed back over HisTrap Ni-Sepharose columns and flow-through fractions containing pure liberated IL-1F6 variant were retained. and tested for activity as described in Example 2B below. Results are shown in Table 7 below.

Example 1C

Preparation of IL-1F9 Variants

Variants of IL-1F9 comprising a C-terminal FLAG-polyHis tag were prepared in a substantially similar manner as described in Example 1A above, using as a template a cDNA clone encoding huIL-1F9 (AF200492). HuIL-1F9S18 (lacking a C-Terminal FLAG-polyHis tag), using as a template a cDNA clone encoding huIL-1F9 (AF200492), was prepared and purified in a substantially similar manner to HuIL-1F6K6 described in Example 1A above except that an extra thymine base pair was removed using a site directed mutagenesis kit according to the manufacturer's instructions (Stratagene, LaJolla, Calif., cat# 200523). The resulting clone was cut with restriction enzymes Nde1 and Hind III and subcloned back into the pET-SUMO vector (Invitrogen, Carlsbad, Calif.). The various N-terminal deletion variants are shown in Table 3 below:

TABLE 3

Amino Acid Sequence of IL-1F9 Variants

| N-Terminal amino acid sequence of IL-1F9 Variants (. . . indicates intervening amino acids of human IL-1F9 (SEQ ID NO 4); SEQ ( ) indicate that the enclosed amino acid is removed; FLAG indicates the ID amino acid sequence DYKDDDDK; polyHis indicates a chain of multiple NO: histidines, typically 6.) | IL-1F9 Variant Polypeptide: (Hu indicates human; WT indicates full length wild type polypeptide, FpH indicates a FLAG poly His tag., the bold, italicized, upper case letter and number refers to the indicated amino acid and its position in SEQ ID NO 4 where the position is relative to the N-Terminal amino acid at position one of SEQ ID NO 4.) |
|---|---|
| 33 MRGTPGDADGGGRAVYQSMCKPITGT . . . FELNIND-FLAG-polyHis | HuIL-1F9WT/FpH |
| 34 (M) SMCKPITGT . . . FELNIND-FLAG-polyHis | HuIL-1F9*S18*/FpH |
| 35 MMCKPITGT . . . FELNIND-FLAG-polyHis | HuIL-1F9*M19*/FpH |
| 36 (M) CKPITGT . . . FELNIND-FLAG-polyHis | HuIL-1F9*C20*/FpH |
| 37 SMCKPITGT . . . FELNIND | HuIL-1F9*S18* |

The constructs were expressed in *E. coli*, and the expressed polypeptides purified from bacterial lysates (soluble fraction) as described previously. Similar to observations for HuIL-1F8, N-terminal sequencing indicated that, for one construct HuIL-1F9C20/FpH), the N-terminal Met was removed from the polypeptide. Purified polypeptides were also tested for activity in a reporter assay substantially as described in Example 2. Results are shown in Table 5 below.

The pH-SUMO construct, encoding HuIL-1F9S18 was introduced into *E. coli* DH10B. Expression was carried out using Overnight Express™ Autoinduction System (Novagen, Darmstadt, Germany, cat# 71300-3) per manufacturer's protocol. The *E. Coli* cells were centrifuged and frozen. Frozen *E. coli* cell pellets were thawed in TBS made in Roche Complete EDTA free protease inhibitor cocktail. After thawing, benzonase was added. Cells were lysed via passage through a Microfluidics microfluidizer 110L device (MFIC Corporation, Newton, Mass.) and resulting lysates clarified via centrifugation. Supernatants were sterile filtered and loaded onto 5 mL HisTrap (GE Biosciences, Piscataway, N.J.) Ni-sepharose columns equilibrated in Tris, NaCl, imidazole pH 7.4. Columns were washed with imidazole in TBS. Protein was eluted with a imidazole linear gradient. Eluted fractions were pooled and dialyzed into PBS using MWCO Slide-A-Lyzers (Pierce Biotechnology, Inc., Rockland, Ill.). LifeSensors SUMO Protease-1 was used to cleave theHis-SUMO fusion partner from IL-1F6 variant. Cleavage reaction products were dialyzed into TBS containing EDTA, pH 7.4 using MWCO Slide-A-Lyzers. Dialyzed pools were then passed back over HisTrap Ni-Sepharose columns and flow-through fractions containing pure liberated IL-1F6 variant were retained. and tested for activity as described in Example 2B below. Results are shown in Table 7 below.

Example 1D

Preparation of IL-1F5 Variants

Variants of IL-1F5 comprising a C-terminal FLAG-poly-His tag were prepared in a substantially similar manner as described in Example 1A above, using as a template a cDNA clone encoding huIL-1F5 (AF201830). HuIL-1F5V2, using as a template a cDNA clone encoding huIL-1F5 (AF201830), was prepared and purified in a substantially similar manner to HuIL-1F6K6 described in Example 1A The various N-terminal deletion variants are shown in Table 4 below:

TABLE 4

Amino Acid Sequence of IL-1F5 Variants

| N-Terminal amino acid sequence of IL-1F5 Variants (. . . indicates intervening amino acids of human IL-1F5 (SEQ ID NO SEQ1); ( ) indicated that the enclosed amino acid is removed; FLAG ID indicates the amino acid sequence DYKDDDDK; polyHis indicates a NO:chain of multiple histidines, typically 6.) | IL-1F5 Variant Polypeptide: (Hu indicates human; WT indicates full length wild type polypeptide, FpH indicates a FLAG poly His tag; the bold, italicized, upper case letter and number refers to the indicated amino acid and its position in SEQ ID NO 1, where the position is relative to the N-Terminal amino acid at position one of SEQ ID NO 1.) |
|---|---|
| 38 MVLSGALCFRMKDSA . . . FYFQQCD-FLAG-polyHis | HuIL-1F5*M1*/FpH |
| 39 (M) VLSGALCFRMKDSA . . . FYFQQCD-FLAG-polyHis | HuIL-1F5*V2*/FpH |
| 40 MLSGALCFRMKDSA . . . FYFQQCD-FLAG-polyHis | HuIL-1F5*L3*/FpH |
| 41 (M) SGALCFRMKDSA . . . FYFQQCD-FLAG-polyHis | HuIL-1F5*S4*/FpH |
| 42 (M) GALCFRMKDSA . . . FYFQQCD-FLAG-polyHis | HuIL-1F5*G5*/FpH |
| 43 VLSGALCFRMKDSA . . . FYFQQCD | HuIL-1F5*V2* |

HuIL-1F5M1/FpH was expressed in *E. coli* as a Glutathione-S-transferase (hereinafter "GST") fusion. The GST domain was cleaved off by digestion with Factor Xa. HuIL-1F5V2/FpH was expressed in COS-1 cells. The remaining constructs were expressed as described above. A full-length form was also expressed in *E. coli*, and found to have the same N-terminal sequence as HuIL-1F5V2FpH; this form was referred to as HuIL-1F5WT/FpH. The polypeptides were purified and tested for their ability to inhibit the activation of IL-1Rrp2 by IL-1F8 in a reporter assay substantially as described in Example 2. In this assay, each purified variant of IL-1F5 was added to IL-1Rrp2 transfected Jurkat cells at 5000, 500, or 50 ng/mL, and the cells were pre-incubated for 15 minutes. At that time, IL-1F8 (untagged, full-length—expressed in *E. coli*; HuIL-1F8WT/FpH) was added at a concentration of 150 ng/mL. The cells were then incubated with the F8/F5 mixtures for five hours at 37° C. Cell lysates were assayed for luciferase activity as previously reported (Towne et al. 2004 *J Biol Chem* 279(14):13677)). Ratios of F5:F8 tested were 33.3:1, 3.3:1, and 0.33:1. Results are shown in Table 5 below.

The pH-SUMO construct, encoding HuIL-1FV2 was introduced into *E. coli* DH10B. Expression was carried out using Overnight Express™ Autoinduction System (Novagen, Darmstadt, Germany, cat# 71300-3) per manufacturer's protocol. The *E. Coli* cells were centrifuged and frozen. Frozen *E. coli* cell pellets were thawed in TBS made in Roche Complete EDTA free protease inhibitor cocktail. After thawing, benzonase was added. Cells were lysed via passage through a Microfluidics microfluidizer 110L device (MFIC Corporation, Newton, Mass.) and resulting lysates clarified via centrifugation. Supernatants were sterile filtered and loaded onto 5 mL HisTrap (GE Biosciences, Piscataway, N.J.) Ni-sepharose columns equilibrated in Tris, NaCl, imidazole pH 7.4. Columns were washed with imidazole in TBS. Protein was eluted with a imidazole linear gradient. Eluted fractions were pooled and dialyzed into PBS using MWCO Slide-A-Lyzers (Pierce Biotechnology, Inc., Rockland, Ill.). LifeSensors SUMO Protease-1 was used to cleave the His-SUMO fusion partner from IL-1F6 variant. Cleavage reaction products were dialyzed into TBS containing EDTA, pH 7.4 using MWCO Slide-A-Lyzers. Dialyzed pools were then passed back over HisTrap Ni-Sepharose columns and flow-through fractions containing pure liberated IL-1F6 variant were retained. and tested for activity as described in Example 2B below. Results are shown in Table 7 below.

EXAMPLE 2

Example 2A

Luciferase Assay of IL-1F Variants

This Example describes a reporter assay used to evaluate the activity of IL-1 family member variants, substantially as described in Towne et al., *J Biol Chem*. 279(14):13677 (2004) herein incorporated by reference in its entirety. Briefly, Jurkat E6.1 cells ($7 \times 10^5$) are transiently transfected via FuGENE 6 (Roche Diagnostics, Basel, Switzerland) as per manufacturer's protocol (i.e., cells are transfected with 200 ng reporter plasmid and 400 ng of either IL-1Rrp2-encoding or empty vector plasmids with a 1:3 DNA/FuGENE 6 ratio). Seventeen hours after transfection, cells are stimulated with the indicated cytokines or cytokine variants for five hours. Cells are lysed and luciferase activity is assessed using reporter lysis buffer (Promega) and Luciferase Assay Reagent (Promega). The results reported herein represent duplicate samples.

TABLE 5

| HuIL-1F Variant | N-Terminal Sequence | SEQ ID NO: | Biological Activity* | Variant start Position** |
|---|---|---|---|---|
| HuIL-1F5 M1/FpH | ~~~~~~~~MVLSGALCFR[M]KDSALKVLYLHNN | 44 | none | −10 |
| HuIL-1F5 V2/FpH | ~~~~~~~~~VLSGALCFR[M]KDSALKVLYLHNN | 45 | >FL | −9 |
| HuIL-1F5 L3/FpH | ~~~~~~~~~MLSGALCFR[M]KDSALKVLYLHNN | 46 | >FL | −9 |
| HuIL-1F5 S4/FpH | ~~~~~~~~~~~SGALCFR[M]KDSALKVLYLHNN | 47 | none | −7 |
| HuIL-1F5 G5/FpH | ~~~~~~~~~~~~GALCFR[M]KDSALKVLYLHNN | 48 | none | −6 |
| HuIL-1F6 K6/FpH | ~~~~~~~~MKIDTPQRGS[I]QDINHRVWVLQDQ | 49 | =FL | −10 |
| HuIL-1F6 I7/FpH | ~~~~~~~~~MIDTPQRGS[I]QDINHRVWVLQDQ | 50 | >>FL | −9 |
| HuIL-1F6 D8/FpH | ~~~~~~~~~~MDTPQRGS[I]QDINHRVWVLQDQ | 51 | =FL | −8 |
| HuIL-1F8 Q4/FpH | ~~~~~~~MQREAAPKSYA[I]RDSRQMVWVLSGN | 52 | =FL | −11 |
| HuIL-1F8 R5/FpH | ~~~~~~~~MREAAPKSYA[I]RDSRQMVWVLSGN | 53 | =FL | −10 |
| HuIL-1F8 E6/FpH | ~~~~~~~~~MEAAPKSYA[I]RDSRQMVWVLSGN | 54 | >>FL | −9 |
| HuIL-1F8 A7/FpH | ~~~~~~~~~~~AAPKSYA[I]RDSRQMVWVLSGN | 55 | <FL | −7 |
| HuIL-1F9 S18/FpH | ~~~~~~~~~SMCKPITGT[I]NDLNQQVWTLQGQ | 56 | >>FL | −9 |
| HuIL-1F9 M19/FpH | ~~~~~~~~~MMCKPITGT[I]NDLNQQVWTLQGQ | 57 | >>FL | −9 |
| HuIL-1F9 C20/FpH | ~~~~~~~~~~~CKPITGT[I]NDLNQQVWTLQGQ | 58 | <FL | −7 |

*Bi

These results demonstrated that the length of the N-terminus is important for biological activity of both agonistic and antagonistic IL-1 family members that signal via IL-1Rrp2.

Example 2B

IL-8 ELISA Assay of IL-1F Variants

A stable cell line expressing human IL-1Rrp2 off an inducible promoter was generated in Jurkat T-REx™ cells (Invitrogen). T-REx™ cell lines stably express the tetracycline repressor protein and, therefore, allow for inducible expression of the gene of interest (IL-1Rrp2) with doxycycline.

In order to access the activity of the IL-1F ligands IL-1Rrp2 expressing Jurkat T-REx™ cells were induced with doxycycline 24 hrs. prior to use. Cells were seeded at 200,000 cells/well in a 96-well round bottom tissue culture plate. The IL-1F ligands (full length (WT) untagged, full length (WT) tagged, truncated tagged or SUMO generated truncated untagged protein) were added to the wells as follows: full length IL-1F6, F8 and F9 were added at 50 μg/mL with an 8 point dilution series at 1:5 dilutions and truncated ligands were started at 2 μg/mL with 1:5 dilutions for 8 points. The cells were incubated with the ligands at 37° C., 5% CO2 for 24 hrs. Following incubation, cells were spun down and the supernatants were collected for analysis using QuantiGlo Human IL-8 ELISA Kit (R&D Systems) per the manfacture's instructions The results for the tested polypeptides and variants are given as indicated in Table 7 below.

EXAMPLE 3

Preparation of Monoclonal Antibodies

IL-1 family member polypeptides may be employed as immunogens in generating monoclonal antibodies by conventional techniques, e.g., techniques described in U.S. Pat. No. 5,599,905, hereby incorporated by reference. It is recognized that polypeptides in various forms may be employed as immunogens, e.g., full length proteins, fragments thereof, fusion proteins thereof such as Fc fusions, cells expressing the recombinant protein on the cell surface, etc. Examples of useful peptides include those shown in FIG. 1.

To summarize an example of such a procedure, an N-terminal peptide of an IL-1Rrp2 requiring IL-1 family member, optionally having an additional C-terminal cysteine residue to facilitate conjugation, is conjugated to maleiimide-activated keyhole limpet hemocyanin (KLH; obtainable for example from Pierce Biotechnology Inc., Rockford, Ill.) to yield an immunogen. For a first immunization, 100 micrograms of immunogen (containing 50 micrograms of peptide) is emulsified in complete Freund's adjuvant (CFA) at 1:1 ratio by volume and injected subcutaneously in a final volume of 200 microliters for each mouse.

Immunized animals are boosted three to four more times with additional immunogen to increase the antigen-specific response, at intervals of two to four weeks (although longer intervals may be employed. For example, a second injection of 50 micrograms of immunogen (containing 25 micrograms of peptide) mixed with incomplete Freund's adjuvant in a final volume of 200 ul is injected subcutaneously into each mouse about four weeks after the primary immunization. A

TABLE 7

IL-8 Elisa Assay Results

| SEQ ID NO: | Polypeptide Assayed: | N-terminal polypeptide sequence<br>A box frames the aliphatic amino acid which is indicated as<br>@ of the consensus sequence: @XD where @ may be M or I,<br>and X is one amino acid. | $EC_{50}$ (μg/mL) |
|---|---|---|---|
| 59 | HuIL-1F6 WT | MEKALKIDTPQQGS☐QDINHRVWVLQDQ | 12.94 |
| 50 | HuIL-1F6 *I7*/FpH | ~~~~~MIDTPQRGS☐QDINHRVWVLQDQ | 0.060 |
| 60 | HuIL-1F6K6 | ~~~~~KIDTPQQGS☐QDINHRVWVLQDQ | 0.000164 |
| 61 | HuIL-1F8WT | MNPQREAAPKSYA☐RDSRQMVWVLSGN | 10.47 |
| 54 | HuIL-1F8 *E6*/FpH | ~~~~~MEAAPKSYA☐RDSRQMVWVLSGN | 0.002 |
| 62 | HuIL-1F8R5 | ~~~~~REAAPKSYA☐RDSRQMVWVLSGN | 0.000129 |
| 63 | HuIL-1F9WT | MRGTPGDADGGGRAVYQSMCKPITGT☐NDLNQQVWTLQGQ | 4.072 |
| 56 | HuIL-1F9 *S18*/FpH | ~~~~~~~~~~~~~~~SMCKPITGT☐NDLNQQVWTLQGQ | 0.017 |
| 56 | HuIL-1F9*S18* | ~~~~~~~~~~~~~~~SMCKPITGT☐NDLNQQVWTLQGQ | 0.001 |

These results demonstrated that the length of the N-terminus is important for biological activity of both agonistic and antagonistic IL-1 family members that signal via IL-1Rrp2 and that the particular N-terminal amino acid is not important. Further, these results demonstrate that polypeptides that do not comprise a C-terminal tag are more active than corresponding polypeptides comprising a C-terminal tag.

third injection (20 micrograms of immunogen containing 10 micrograms of peptide mixed with an adjuvant such as Ribi adjuvant) may be given by subcutaneous and/or intraperitoneal route from about 10 to 30 days after the second injection. If desired, a fourth injection (20 micrograms of immunogen containing 10 micrograms of peptide mixed with incomplete Freund's adjuvant) may be given by subcutaneous and/or intraperitoneal route from about 14 to about 28 days after the third injection. A final injection is given, usually about five days prior to fusion, utilizing 50 micrograms of immunogen containing 25 micrograms of peptide in PBS, by intraperitoneal injection.

Serum samples may be periodically taken by retro-orbital bleeding or tail-tip excision for testing by peptide ELISA (enzyme-linked immunosorbent assay), or another suitable assay, to evaluate antibody titer. At the time of fusion, the animals are sacrificed, splenocytes harvested, and fused to the murine myeloma cell line SP2/O (ATCC CRL 1581). The resulting hybridoma cell lines are plated in multiple microtiter plates in a HAT selective medium (hypoxanthine, aminopterin, and thymidine) to facilitate proliferation of spleen cell-myeloma hybrid cells.

Hybridoma clones thus generated are screened for reactivity with the N-terminal portion of the relevant IL-1 family member. Initial screening of hybridoma supernatants may utilize a peptide ELISA, a whole cell ELISA and/or a cell-based assay suitable for high-throughput screening (fluorometric microvolume assay technology or FMAT, substantially as described by Fiscella, et al., Nature Biotechnology 21:302-307 (2003). Hybridomas that are positive in this screening method may be further cultured to provide larger amounts of antibody, which can then be purified as described below and screened by additional cell-based assay(s) (for example, a reporter assay, or another assay for biological activity of an IL-1 family member).

Selected hybridomas can be further cloned and tested to ensure stable production monoclonal antibody. Hybridomas can be cultured in vitro, or passaged as ascites fluid in suitable host mammals. The resulting monoclonal antibodies may be purified by ammonium sulfate precipitation followed by gel exclusion chromatography, and/or affinity chromatography based on binding of antibody to Protein G, for example.

EXAMPLE 4

Purification of Hybridoma Antibodies for Screening

Hybridoma cells are cultured for a time and under conditions to yield a sample of about 35 ml of hybridoma supernatant fluid. To each sample is added 12 ml of 4×-Protein A Binding Buffer (1.6 M citric acid, 100 mM tris, pH 9.15) and about 300 μl of a 67% slurry of MabSelect™ Media (GE Healthcare, Piscataway, N.J.). The resulting slurry is rotated gently over night at 4° C.

After overnight incubation, the samples are centrifuged to sediment the resin and the monoclonal antibodies bound thereto, for example at 2,000 RPM in a G3.8 centrifuge rotor (Beckman Coulter, Fullerton, Calif.) for 5 minutes at 4° C. with no brake. All but about 300 μl of the supernatant fluid is removed and the resin is resuspended to form a concentrated slurry.

The concentrated slurry is transferred to a microcentrifuge tube and sufficient 1×-Protein A Binding Buffer (400 mM citric acid, 25 mM tris, pH 8.9) is added to bring the total volume up to about 1 ml. The slurry is resuspended, then centrifuged at about 14,000 g for 5 seconds. The supernatant fluid is removed from the resulting pellet, which is washed a total of three times in a similar manner (i.e. by resuspending in about 1 ml of 1×-Protein A Binding Buffer, centrifuging, removing supernatant and resuspending in fresh buffer).

After three washes, the pellet is resuspended in 400 μl Elution Buffer (200 mM formic acid) and agitated for 10 min at room temperature, then centrifuged at 14,000 g for 5 seconds. The supernatant is carefully removed as eluate, and the pellet is eluted again in a manner similar to that described above for a total of three elution cycles. The eluates from the three elution cycles are combined, centrifuge at 14,000 g for 5 min room temperature and transferred to a fresh tube. The pH is adjusted to 7.8-8.2 by adding 2 M tris base (235 mM$_f$) and mixing quickly. The samples are again centrifuged at 14,000 g for 5 min at room temperature, and designated as pH Shift Soluble. A spectral scan of each sample (diluted by adding 20 μl of the sample to 700 μl water) is run from 250 to 350 nm, and protein concentration is verified by loading 0.5 μg each antibody-containing sample on a reducing 4-20% SDS-PAGE gel with an appropriate antibody standards.

Each reference cited herein is incorporated by reference in its entirety for all that it teaches and for all purposes.

What is claimed is:

1. An isolated IL-1F5 polypeptide that antagonizes signal transduction through IL-1Rrp2, comprising the amino acid sequence set forth in SEQ ID NO: 8, wherein the N-terminus of said IL-1F5 polypeptide starts at amino acid position one of the amino acid sequence set forth in SEQ ID NO: 8.

2. The isolated IL-1F5 polypeptide of claim 1 consisting of the amino acid sequence set forth in SEQ ID NO: 7 or SEQ ID NO: 8.

3. A composition comprising the polypeptide of claim 1 and a physiologically acceptable diluent, excipient or carrier.

\* \* \* \* \*